US008748577B2

(12) United States Patent
Besman et al.

(10) Patent No.: US 8,748,577 B2
(45) Date of Patent: Jun. 10, 2014

(54) CONJUGATES OF BIOLOGICALLY ACTIVE POLYPEPTIDES HAVING AN INCREASED IN VIVO HALF-LIFE

(75) Inventors: Marc Besman, Seattle, WA (US); Stewart Chipman, Bainbridge Island, WA (US); David Leung, Mercer Island, WA (US); Jack Singer, Seattle, WA (US)

(73) Assignee: Cell Therapeutics, Inc., Seattle, WA (US)

( * ) Notice: Subject to any disclaimer, the term of this patent is extended or adjusted under 35 U.S.C. 154(b) by 0 days.

(21) Appl. No.: 13/363,278

(22) Filed: Jan. 31, 2012

(65) Prior Publication Data

US 2012/0252717 A1 Oct. 4, 2012

Related U.S. Application Data

(63) Continuation of application No. 12/251,324, filed on Oct. 14, 2008, now Pat. No. 8,129,348, which is a continuation of application No. 11/880,377, filed on Jul. 20, 2007, now abandoned, which is a continuation of application No. PCT/US2006/002501, filed on Jan. 25, 2006.

(60) Provisional application No. 60/712,585, filed on Aug. 30, 2005, provisional application No. 60/647,119, filed on Jan. 25, 2005.

(51) Int. Cl.

| | |
|---|---|
| ***C07K 14/00*** | (2006.01) |
| ***A61K 38/16*** | (2006.01) |
| ***A61K 38/14*** | (2006.01) |

(52) U.S. Cl.
USPC .......... 530/350; 530/395; 514/21.2; 514/20.9

(58) Field of Classification Search
None
See application file for complete search history.

(56) References Cited

U.S. PATENT DOCUMENTS

| | | | | |
|---|---|---|---|---|
| 4,810,643 | A | 3/1989 | Souza | |
| 5,985,265 | A | 11/1999 | Kinstler | |
| 6,583,272 | B1 | 6/2003 | Bailon | |
| 6,831,158 | B2 | 12/2004 | Nissen | |
| 8,129,348 | B2 * | 3/2012 | Besman et al. | 514/21.2 |

FOREIGN PATENT DOCUMENTS

| | | | |
|---|---|---|---|
| JP | 4-503606 | A | 7/1992 |
| JP | 2002-516610 | A | 6/2002 |
| WO | 90/09800 | A1 | 9/1990 |
| WO | 98/49198 | A1 | 11/1998 |
| WO | 02/02597 | A2 | 1/2002 |

OTHER PUBLICATIONS

Egrie, J.C., et al., "Characterization and Biological Effects of Recombinant Human Erythropoietin," Immunobiology 172(3-5):213-224, Sep. 1986.

Elliott, S , et al., "Enhancement of Therapeutic Protein in Vivo Activities Through Glycoengineering," Nature Biotechnology 21(4):414-421, Apr. 2003.

Krantz, S.B., "Erythropoietin," Blood 77(3):419-434, Feb. 1991.

Lord, B.I., et al., "Kinetics of Neutrophil Production in Normal and Neutropenic Animals During the Response to Filgrastim (r-metHu G-CSF) or Filgrastim SD/01 (PEG-r-metHu G-CSF)," Clinical Cancer Research 7(7)2085-2090, Jul. 2001.

Perlman, S., et al., "Glycosylation of an N-Terminal Extension Prolongs the Half-Life and Increases the In Vivo Activity of Follicle Stimulating Hormone," Journal of Clinical Endocrinology & Metabolism 88(7):3227-3235, Jul. 2003.

Sasaki, H., et al., "Carbohydrate Structure of Erythropoietin Expressed in Chinese Hamster Ovary Cells by a Human Erythropoietin cDNA," Journal of Biological Chemistry 262(25):12059-12076, Sep. 1987.

Van Der Auwera, P., et al,, "Pharmacodynamics and Pharmacokinetics of Single Doses of Subcutaneous Pegylated Human G-CSF Mutant (Ro 25-8315) in Healthy Volunteers: Comparison With Single and Multiple Daily Doses of Filgrastim," American Journal of Hematology 66(4):245-251, Apr. 2001.

International Search Report and Written Opinion mailed Sep. 15, 2006, issued in corresponding International Application No. PCT/US2006/002501, filed Jan. 25, 2006, 11 pages.

* cited by examiner

*Primary Examiner* — Christine J Saoud
*Assistant Examiner* — Jegatheesan Seharaseyon
(74) *Attorney, Agent, or Firm* — Christensen O'Connor Johnson Kindness PLLC

(57) ABSTRACT

Disclosed are biologically active protein conjugates that comprise a biologically active polypeptide coupled via a peptide bond to a polypeptide comprising from 2 to about 500 units of a repeating peptide motif, wherein the biologically active protein conjugate exhibits a modified plasma half-life compared to the intrinsic half-life of the unconjugated biologically active polypeptide or protein. Also disclosed are methods of making and using the conjugated proteins, as well as methods for determining whether a given conjugate exhibits a modified half life relative to the intrinsic half life of the unconjugated polypeptide.

8 Claims, 6 Drawing Sheets

CONJUGATES OF BIOLOGICALLY ACTIVE POLYPEPTIDES HAVING AN INCREASED IN VIVO HALF-LIFE

CROSS-REFERENCE TO RELATED APPLICATIONS

The present application is a continuation of U.S. application Ser. No. 12/251,324, filed Oct. 14, 2008, which is a continuation of U.S. application Ser. No. 11/880,377, filed Jul. 20, 2007, which is a continuation of International Application No. PCT/US2006/002501, filed Jan. 25, 2006, published in English, which claims priority under 35 U.S.C. 119 (e) from U.S. Provisional Application No. 60/712,585, filed Aug. 30, 2005 and U.S. Provisional Application No. 60/647,119, filed Jan. 25, 2005, all of which are incorporated by reference herein.

TECHNICAL FIELD

This invention relates generally to biologically active proteins, and more specifically to altering the haft-life of biologically active proteins.

SEQUENCE LISTING

The sequence listing associated with this application is provided in text format in lieu of a paper copy and is hereby incorporated by reference into the specification. The name of the text file containing the sequence listing is 38616_Sequence_Substitute_2012-05-01.txt. The text file is 2.08 MB; was created on May 1, 2012; and has been submitted via EFS-Web.

BACKGROUND OF THE INVENTION

Biologically active proteins often have undesirable half-lives when administered as human therapeutics. Their intrinsic half-lives impose administration schedules and dosing regimens that often result in less than optimal therapeutic efficacy, compliance problems and patient inconvenience.

In the manufacture of biologically active proteins for human therapeutics, the extension of the half-life of biologically active proteins has been attempted through physical means (e.g., altered route of administration, nanoparticle encapsulation and liposomal entrapment), chemical modification (e.g., emulsions, pegylation and hyperglycosylation) and genetic modification (e.g., modification of primary protein structure, polymer tags, human serum albumin fusion, incorporation of post-translational modification). See, for example, Lord, et al., Clin. Cancer Res. 7:2085-2090 (2001), and van Der Auwera, et al., Am. J. Hematol. 66:245-251 (2001). However, such approaches have resulted in other problems. Extension of biologically active protein half-life through physical means often introduces increased drug substance complexity with costly and time-consuming additional downstream processes during manufacturing. Chemical modification may alter the biological activity or safety profile of the biologically active protein. Where biologically active proteins are made via recombinant DNA synthesis methodology, the effect of the genetic modification on protein yield and purity in the particular cellular expression systems issues needs to be assessed for its intended use.

Accordingly, there is a need for other approaches for modifying the intrinsic half-life of biologically active proteins.

SUMMARY OF THE INVENTION

One aspect of the present invention is directed to a protein conjugate comprising a biologically active polypeptide coupled via a peptide bond to a polypeptide (amino acid extension) that comprises from 2 to about 500 repeating units of a peptide motif. The motif comprises a major constituent and a minor constituent, in which the major constituent is two or more residues of one amino acid selected from Gly (G), Asn (N) and Gln (Q), and the minor constituent is one or more residues of one amino acid selected from Ala (A), Ser (S), Thr (T), Asp (D), Gln (Q), Glu (E), His (H) and Asn (N), with the proviso that none of the amino acids is present in both the major constituent and said minor constituent, wherein the plasma half-life of the conjugate is modified relative to the intrinsic half-life of the unconjugated biologically active polypeptide. The term "modified", as used herein, refers to an increased or a decreased half-life relative to the plasma half-life of the unconjugated biologically active polypeptide or protein itself (i.e., the intrinsic half life). By the phrase "intrinsic half-life" it is meant the half-life of the native biologically active polypeptide or the half-life of the polypeptide in unconjugated form (thus including recombinant forms of the native polypeptide).

In some embodiments, the peptide motif comprises 3-6 amino acid residues (i.e., 3, 4, 5 or 6). In some embodiments, wherein the peptide motif contains 5 or 6 amino acid residues, the minor constituent comprises 1 amino acid residue of said peptide. In some embodiments, the peptide motif has a sequence consisting of N and T amino acid residues, N and E amino acid residues, Q and S amino acid residues, or N and Q amino acid residues. In some embodiments, the amino acid extension is N-terminal with respect to said biologically active polypeptide; in some embodiments, it is C-terminal with respect to said biologically active polypeptide; and in other embodiments, it is situated at both the N and C-terminus with respect to said biologically active polypeptide. In some embodiments, the biologically active polypeptide is a cytokine (e.g., granulocyte colony stimulating factor (G-CSF), human growth hormone (SEQ ID NO:2472), or an interferon such as a beta-interferon (SEQ ID NO:2468) or a gamma-interferon (SEQ ID NO:2470)), an antibody, antibody fragment, proteolytic antibody fragment or domain, single chain antibody, genetically or chemically optimized antibody or fragment thereof, a soluble gp 120 or gp 160 glycoprotein, a coagulation factor, a soluble receptor such as a tumor necrosis factor (TNF)-$\alpha$ type II receptor (SEQ ID NO:2464), a therapeutic enzyme or erythropoietin (EPO; SEQ ID NOs:2452, 2480 and 2481). In some embodiments, the protein conjugate has a modified half-life that is decreased relative to the intrinsic half-life of the unconjugated biologically active polypeptide, e.g., wherein said biologically active polypeptide comprises a recombinant activated protein C or a recombinant Factor VII.

Another aspect of the present invention is directed to a composition comprising the protein conjugate and a carrier. In some embodiments, the composition is a pharmaceutical composition and the carrier is a pharmaceutically acceptable carrier.

Another aspect of the present invention is directed to a chimeric DNA molecule that encodes the protein conjugate described above, as well as a vector, together comprising the chimeric DNA molecule, and a cell transformed with the chimeric DNA molecule or a vector containing it. In some embodiments, the vector is a plasmid, e.g., pCE2. In some embodiments, the cell is a mammalian cell e.g., a Chinese hamster ovary (CHO) cell, or a bacterium e.g., *E. coli*, or yeast.

Yet another aspect of the present invention is directed to a method of making a biologically active protein conjugate comprising a biologically active polypeptide coupled via peptide bond to a polypeptide comprising from 2 to about 500 units of a peptide comprising as a major constituent, two or more residues of one amino acid selected from Gly (G), Asn (N) and Gln (Q), and as a minor constituent, one or more residues of one amino acid selected from Ala (A), Ser (S), Thr (T), Asp (D), Gln (Q), Glu (E), His (H) and Asn (N), provided that none of said amino acids is present in said major constituent and said minor constituent, such that said biologically active protein has a modified plasma half-life compared to intrinsic half-life of the unconjugated biologically active polypeptide, said method comprising: culturing a cell transformed with a chimeric DNA molecule encoding said protein conjugate under conditions whereby said DNA is expressed, thereby producing said protein conjugate; and extracting an expression product of said chimeric DNA molecule from said cell.

A further aspect of the present invention is directed to a method of determining whether a given protein conjugate exhibits a modified plasma half-life compared to the intrinsic half-life of the unconjugated biologically active polypeptide, comprising: a) preparing a protein conjugate comprising a biologically active polypeptide coupled via a peptide bond to a polypeptide that comprises from 2 to about 500 repeating units of a peptide motif, wherein the motif comprises a major constituent and a minor constituent, in which the major constituent comprises or consists of two or more residues of one amino acid selected from the group consisting of Gly (G), Asn (N) and Gln (Q), and the minor constituent comprises or consists of one or more residues of one amino acid selected from the group consisting of Ala (A), See (S), Thr (T), Asp (D), Gln (Q), Glu (E), His (H) and Asn (N), wherein none of the amino acids is present in both the major constituent and said minor constituent, and b) testing the protein conjugate to determine whether the protein conjugate has a modified plasma half-life compared to the intrinsic half-life of the unconjugated biologically active polypeptide.

DETAILED DESCRIPTION

Figure 1:
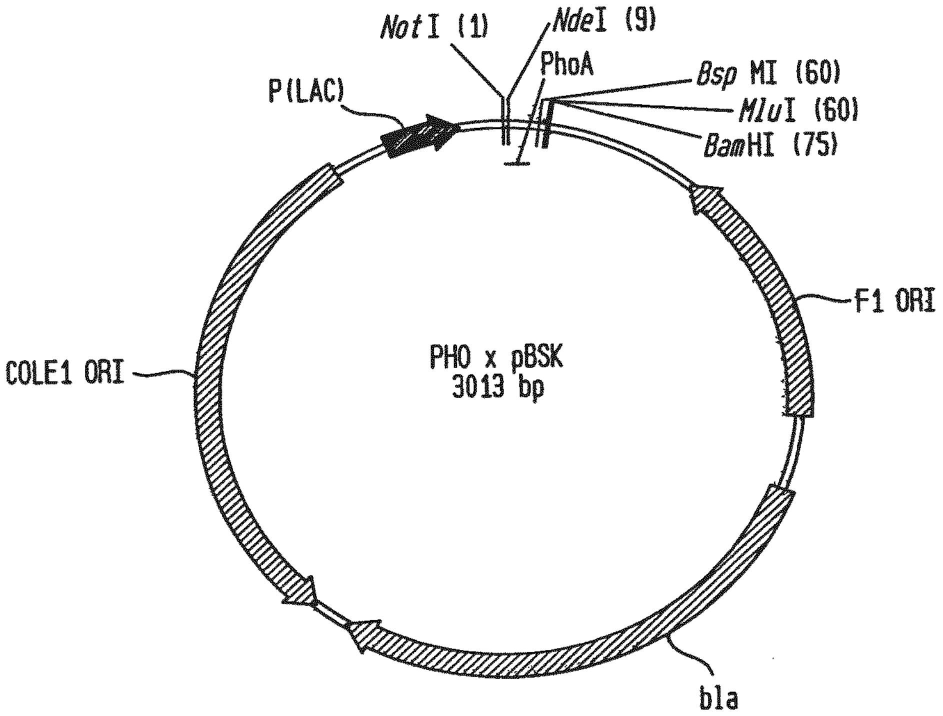
FIG. 1 is a schematic representation of the PHO×pBSK vector.

As used herein, the term "polypeptide" means a polymer of amino acids having no specific length, unless otherwise specified. Thus, peptides and proteins are included in the definition of "polypeptide" and these terms are used interchangeably throughout the specification, as well as in the claims. The term "polypeptide" does not exclude post-translational modifications, such as polypeptides having covalent attachment of glycosyl groups, acetyl groups, phosphate groups, lipid groups, hydroxylation of proline or lysine, and the like. Also encompassed by this definition of "polypeptide" are homologs thereof.

The term "purified" as used herein means that the biologically active protein conjugate has been purified to a level adequate for its intended use.

The present invention is directed, in a general aspect, to a protein conjugate comprising a biologically active polypeptide coupled via peptide bond to a polypeptide that comprises from 2 to about 500 units of a peptide motif that contains a major constituent of two or more residues of one amino acid selected from Gly (G), Asn (N) and Gln (Q), and a minor constituent of one or more residues of one amino acid selected from Ala (A), Ser (S), Thr (T), Asp (D), Gln (Q), Glu (E), His (H) and Asn (N), provided that none of the amino acids is present as both a major constituent and minor constituent. The protein conjugates of the present invention have a plasma half-life greater than the corresponding unconjugated biologically active polypeptide or protein.

The repeating unit of the motif generally contains 3-7 (3, 4, 5, 6 or 7) amino acid residues. Representative peptide motifs having N (Asn) as the major constituent are described in Table 1.

Representative peptide motifs having G (Gly) as the major constituent are described in Table 2.

Representative peptide motifs having Q (Gln) as the major constituent are described in Table 3.

The number of the peptide motifs ranges from 2 to about 500. Thus, the motifs including the specific peptide motifs set forth herein, may be present in the polypeptide in the following number of units: 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400

401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499 and 500 (thus including any subrange thereof).

As described above, the polypeptide conjugated to the biologically active polypeptide may also be referred to as an amino acid or polyamino extension (hereinafter “amino acid extension”) of the biologically active polypeptide. The amino acid extension may be situated at the N-terminus, at the C-terminus or at both the N and C-termini, with respect to the biologically active polypeptide sequence.

Without intending to be bound by theory, Applicants believe that the amino acid extensions do not adopt stable conformations and as such, do not interfere with or otherwise influence the activity of the protein. Also, limiting the amino acid extension to two different amino acids is believed to reduce the chemical complexity of the amino acid extension, which helps minimize the potential for immunogenicity, as well as allowing for the modulation of physicochemical properties far more extensively than is possible through the use of just one type or kind of amino acid.

Broadly, the biologically active polypeptide includes any protein (including native polypeptides (i.e., as they exist in vivo)) or polypeptides produced recombinantly, such as recombinant human G-CSF (rh-G-CSF; SEQ ID NO:2450) for which a modified plasma half-life would be desirable from some standpoint, particularly from a therapeutic standpoint, meaning that when delivered to a vertebrate organism, treats, e.g., cures, ameliorates, or lessens the symptoms of, a given disease in that vertebrate, or alternatively, prolongs the life of the vertebrate by slowing the progress of a terminal disease. Types of biologically active proteins include cytokines, chemokines, lymphokines, ligands, receptors, hormones, apoptosis-inducing polypeptides, enzymes, antibodies and antibody fragments, and growth factors. Examples of receptors include TNF type I receptor, SEQ ID NO:2466, IL-1 receptor type II, IL-1 receptor antagonist, IL-4 receptor and any chemically or genetically modified soluble receptors. Examples of enzymes include activated protein C, factor VII, collagenase (e.g., marketed by Advance Biofactures Corporation under the name SANTYL®); agalsidase-beta (e.g., marketed by Genzyme under the name FABRAZYME®); dornase-alpha (e.g., marketed by Genentech under the name PULMOZYME®); alteplase (e.g., marketed by Genentech under the name ACTIVASE®); pegylated-asparaginase (e.g., marketed by Enzon under the name ONCASPAR®); asparaginase (e.g., marketed by Merck under the name ELSPAR®); and imiglucerase (e.g., marketed by Genzyme under the name CEREDASE®). Examples of specific polypeptides or proteins include, but are not limited to granulocyte macrophage colony stimulating factor (GM-CSF; SEQ ID NO:2462), granulocyte colony stimulating factor (G-CSF; SEQ ID NO:2450), macrophage colony stimulating factor (M-CSF; SEQ ID NOs: 2454, 2456, 2458, and 2460), colony stimulating factor (CSF), interferon beta (IFN-β, SEQ ID NO:2468), interferon gamma (IFNγ, SEQ ID NO:2472), interferon gamma inducing factor I (IGIF), transforming growth factor beta (TGF-β), RANTES (regulated upon activation, normal T-cell expressed and presumably secreted), macrophage inflammatory proteins (e.g., MIP-1-α and MIP-1-β), Leishmania elongation initiating factor (LEIF), platelet derived growth factor (PDGF), tumor necrosis factor (TNF), growth factors, e.g., epidermal growth factor (EGF), vascular endothelial growth factor (VEGF), fibroblast growth factor, (FGF), nerve growth factor (NGF), brain derived neurotrophic factor (BDNF), neurotrophin-2 (NT-2), neurotrophin-3 (NT-3), neurotrophin-4 (NT-4), neurotrophin-5 (NT-5), glial cell line-derived neurotrophic factor (GDNF), ciliary neurotrophic factor (CNTF), TNF α type II receptor (SEQ ID NO:2464), erythropoietin (EPO; SEQ ID NOs:2452, 2480 and 2481), insulin and soluble glycoproteins e.g., gp120 and gp160 glycoproteins. The gp120 glycoprotein is a human immunodeficiency virus (HIV) envelope protein, and the gp160 glycoprotein is a known precursor to the gp 120 glycoprotein.

In some embodiments, it is desirable to modify the half-life of a biologically active polypeptide such that it is decreased relative to the intrinsic half life, is desirable. Such embodiments include recombinant activated protein C (e.g., marketed by Eli Lilly under the name XIGRIS®) and Recombinant Factor VII (marketed by Novo Nordisk under the name NOVOSEVEN®).

Biologically active polypeptides may be used to treat diseases such as Parkinson’s disease, cancer, and heart disease. In addition, therapeutic polypeptides may be used to treat autoimmune disorders such as multiple sclerosis; Sjogren’s syndrome; sarcoidosis; insulin dependent diabetes mellitus; autoimmune thyroiditis; arthritis (e.g., osteoarthritis, rheumatoid arthritis, reactive arthritis, and psoriatic arthritis); ankylosing spondylitis; and scleroderma. Also, therapeutic polypeptides of the present invention can be used to treat acute and chronic inflammatory disorders, to promote increase in stature, to promote wound healing, and to prevent rejection after transplantation of cells, tissues, or organs.

In some preferred embodiments, the polypeptide is G-CSF. G-CSF induces rapid proliferation and release of neutrophilic granulocytes to the bloodstream, thereby providing a therapeutic effect in fighting infection. As explained in U.S. Pat. No. 6,831,158, recombinant human (rh)-G-CSF is generally used for treating various forms of leukopenia (a reduced level of white blood cells) and neutropenia (a reduced level of neutrophils). Leukopenia and neutropenia result in an increased susceptibility to various infections.

Commercial preparations of rh-G-CSF are available under the names filgrastim (GRAN® and NEUPOGEN®), lenograstim (NEUTROGIN® and GRANOCYTE®) and nartograstim (NEU-UP®). GRAN® and NEUPOGEN® are non-glycosylated and produced in recombinant *E. coli* cells. NEUTROGIN® and GRANOCYTE® are glycosylated and produced in recombinant CHO cells, NEU-UP® is non-glycosylated with five amino acids substituted at the N-terminal region of intact rh-G-CSF produced in recombinant *E. coli* cells.

Aside from G-CSF, per se, G-CSF analogs that are biologically functional or have biological activity are also useful. Methods of preparing rh-G-CSF are disclosed in U.S. Pat. No. 4,810,643. Various G-CSF analogs are also reported in U.S. Pat. No. 4,810,643. The polynucleotide encoding rh-G-CSF and the amino acid structure of rh-G-CSF are both provided in U.S. Pat. No. 5,985,265.

A representative example of an amino acid sequence (SEQ ID NO: 2450) (and the corresponding polynucleotide sequence (SEQ ID NO: 2451)) of a protein conjugate of the present invention is shown in Table 4. The PHO leader sequence is included.

In the amino acid sequence, the PHO leader sequence is from amino acids 1 to 18, G-CSF is from amino acids 19 to 192, and the NNT155 amino acid extension (NNT155 disclosed as SEQ ID NO: 2) is from amino acids 193 to 347. The stop codon is denoted by the “*” symbol.

As depicted in the polynucleotide sequence (SEQ ID NO: 2451), nucleic acids 1 to 54 encode the PHO leader sequence, nucleic acids 55 to 576 encode G-CSF, and nucleic acids 577 to 1041 encode the NNT155 amino acid extension (NNT155 disclosed as SEQ ID NO: 2). Nucleic acids 1042 to 1044 (TAG) constitute the stop codon.

In some embodiments, the number of repeating peptide units is between 75 and 225. Thus, in the case of a protein conjugate containing G-CSF linked to a polypeptide containing repeating units of peptide motif having the sequence NNT, embodiments of the present invention may include any of the following protein conjugates ($(NNT)_{75}$-$(NNT)_{225}$ disclosed as SEQ ID NOS: 4-83, 4748 and 84-153, respectively, in order of appearance): G-CSF-$(NNT)_{75}$, G-CSF-$(NNT)_{76}$, G-CSF-$(NNT)_{77}$, G-CSF-$(NNT)_{78}$, G-CSF-$(NNT)_{79}$, G-CSF-$(NNT)_{80}$, G-CSF-$(NNT)_{81}$, G-CSF-$(NNT)_{82}$, G-CSF-$(NNT)_{83}$, G-CSF-$(NNT)_{84}$, G-CSF-$(NNT)_{85}$, G-CSF-$(NNT)_{86}$, G-CSF-$(NNT)_{87}$, G-CSF-$(NNT)_{88}$, G-CSF-$(NNT)_{89}$, G-CSF-$(NNT)_{90}$, G-CSF-$(NNT)_{91}$, G-CSF-$(NNT)_{92}$, G-CSF-$(NNT)_{93}$, G-CSF-$(NNT)_{94}$, G-CSF-$(NNT)_{95}$, G-CSF-$(NNT)_{96}$, G-CSF-$(NNT)_{97}$, G-CSF-$(NNT)_{98}$, G-CSF-$(NNT)_{99}$, G-CSF-$(NNT)_{100}$, G-CSF-$(NNT)_{101}$, G-CSF-$(NNT)_{102}$, G-CSF-$(NNT)_{103}$, G-CSF-$(NNT)_{104}$, G-CSF-$(NNT)_{105}$, G-CSF-$(NNT)_{106}$, G-CSF-$(NNT)_{107}$, G-CSF-$(NNT)_{108}$, G-CSF-$(NNT)_{109}$, G-CSF-$(NNT)_{110}$, G-CSF-$(NNT)_{111}$, G-CSF-$(NNT)_{112}$, G-CSF-$(NNT)_{113}$, G-CSF-$(NNT)_{114}$, G-CSF-$(NNT)_{115}$, G-CSF-$(NNT)_{116}$, G-CSF-$(NNT)_{117}$, G-CSF-$(NNT)_{118}$, G-CSF-$(NNT)_{119}$, G-CSF-$(NNT)_{120}$, G-CSF-$(NNT)_{121}$, G-CSF-$(NNT)_{122}$, G-CSF-$(NNT)_{123}$, G-CSF-$(NNT)_{124}$, G-CSF-$(NNT)_{125}$, G-CSF-$(NNT)_{126}$, G-CSF-$(NNT)_{127}$, G-CSF-$(NTT)_{128}$, G-CSF-$(NNT)_{129}$, G-CSF-$(NNT)_{130}$, G-CSF-$(NNT)_{131}$, G-CSF-$(NNT)_{132}$, G-CSF-$(NNT)_{133}$, G-CSF-$(NNT)_{134}$, G-CSF-$(NNT)_{135}$, G-CSF-$(NNT)_{136}$, G-CSF-$(NNT)_{137}$, G-CSF-$(NNT)_{138}$, G-CSF-$(NNT)_{139}$, G-CSF-$(NNT)_{140}$, G-CSF-$(NNT)_{141}$, G-CSF-$(NNT)_{142}$, G-CSF-$(NNT)_{143}$, G-CSF-$(NNT)_{144}$, G-CSF-$(NNT)_{145}$, G-CSF-$(NNT)_{146}$, G-CSF-$(NNT)_{147}$, G-CSF-$(NNT)_{148}$, G-CSF-$(NNT)_{149}$, G-CSF-$(NNT)_{150}$, G-CSF-$(NNT)_{151}$, G-CSF-$(NNT)_{152}$, G-CSF-$(NNT)_{153}$, G-CSF-$(NNT)_{154}$, G-CSF-$(NNT)_{155}$, G-CSF-$(NNT)_{156}$, G-CSF-$(NNT)_{157}$, G-CSF-$(NNT)_{158}$, G-CSF-$(NNT)_{159}$, G-CSF-$(NNT)_{160}$, G-CSF-$(NNT)_{161}$, G-CSF-$(NNT)_{162}$, G-CSF-$(NNT)_{163}$, G-CSF-$(NNT)_{164}$, G-CSF-$(NNT)_{165}$, G-CSF-$(NNT)_{166}$, G-CSF-$(NNT)_{167}$, G-CSF-$(NNT)_{168}$, G-CSF-$(NNT)_{169}$, G-CSF-$(NNT)_{170}$, G-CSF-$(NNT)_{171}$, G-CSF-$(NNT)_{172}$, G-CSF-$(NNT)_{173}$, G-CSF-$(NNT)_{174}$, G-CSF-$(NNT)_{175}$, G-CSF-$(NNT)_{176}$, G-CSF-$(NNT)_{177}$, G-CSF-$(NNT)_{178}$, G-CSF-$(NNT)_{179}$, G-CSF-$(NNT)_{180}$, G-CSF-$(NNT)_{181}$, G-CSF-$(NNT)_{182}$, G-CSF-$(NNT)_{183}$, G-CSF-$(NNT)_{184}$, G-CSF-$(NNT)_{185}$, G-CSF-$(NNT)_{186}$, G-CSF-$(NNT)_{187}$, G-CSF-$(NNT)_{188}$, G-CSF-$(NNT)_{189}$, G-CSF-$(NNT)_{190}$, G-CSF-$(NNT)_{191}$, G-CSF-$(NNT)_{192}$, G-CSF-$(NNT)_{193}$, G-CSF-$(NNT)_{194}$, G-CSF-$(NNT)_{195}$, G-CSF-$(NNT)_{196}$, G-CSF-$(NNT)_{197}$, G-CSF-$(NNT)_{198}$, G-CSF-$(NNT)_{199}$, G-CSF-$(NNT)_{200}$, G-CSF-$(NNT)_{201}$, G-CSF-$(NNT)_{202}$, G-CSF-$(NNT)_{203}$, G-CSF-$(NNT)_{204}$, G-CSF-$(NNT)_{205}$, G-CSF-$(NNT)_{206}$, G-CSF-$(NNT)_{207}$, G-CSF-$(NNT)_{208}$, G-CSF-$(NNT)_{209}$, G-CSF-$(NNT)_{210}$, G-CSF-$(NNT)_{211}$, G-CSF-$(NNT)_{212}$, G-CSF-$(NNT)_{213}$, G-CSF-$(NNT)_{214}$, G-CSF-$(NNT)_{215}$, G-CSF-$(NNT)_{216}$, G-CSF-$(NNT)_{217}$, G-CSF-$(NNT)_{218}$, G-CSF-$(NNT)_{219}$, G-CSF-$(NNT)_{220}$, G-CSF-$(NNT)_{221}$, G-CSF-$(NNT)_{222}$, G-CSF-$(NNT)_{223}$, G-CSF-$(NNT)_{224}$ and G-CSF-$(NNT)_{225}$.

In other preferred embodiments, the polypeptide is EPO. As explained in Krantz, Blood 77:419 (1991), naturally occurring EPO stimulates the division and differentiation of committed erythoid progenitors in the bone marrow and exerts its biological activity by binding to receptors and erythroid precursors. EPO has been manufactured biosynthetically using recombinant technology as the product of a cloned human EPO (hEPO) gene inserted into and expressed in Chinese hamster ovary (CHO) cells. See Egrie, et al., Immunobiol. 72:213-224 (1986). The primary structure (i.e., amino acid sequence) of the predominant, fully processed form of hEPO is illustrated in U.S. Pat. No. 6,583,272. In EPO, there are two disulfide bridges between $Cys^7$-$Cys^{161}$ and $Cys^{29}$-$Cys^{33}$. The molecular weight of the polypeptide chain of EPO without the sugar moieties is 18,236 DA. In the intact EPO molecule, approximately 40% of the molecular weight is accounted for by carbohydrate groups that glycosylate the protein at glycosylation sites on the protein. See Sasaki, et al., J. Biol. Chem. 262:12059 (1987).

Because hEPO is essential in red blood formation, the hormone is useful in the treatment of blood disorders characterized by low or defective red blood cell production. Clinically, EPO is used in the treatment of anemia in chronic renal failure (CRF) patients. See Eschbach, et al., NEJM 316:73-78 (1987); Eschbach, et al., Ann. Intern. Med. 111:992 (1989); Egrie, et al., Kidney Intl. 33:262 (1988); and Lim et al., Ann. Intern. Med. 110:108-114 (1989). EPO has also been used for the treatment of anemia in Acquired Immune Deficiency Syndrome (AIDS) and cancer patients undergoing chemotherapy. See R. P. Datum, et al., Erythropoietin In Clinical Applications—An International Perspective 301-324 (M. B. Garnick, ed., Marcel Dekker 1990).

Amino acid and corresponding nucleotide sequences of EPO, as well as other biologically active polypeptides useful in the present invention, are set forth in Table 5. Two other amino acid sequences of EPO are set forth in Table 6.

The protein conjugate may further comprise one or more affinity tags. Generally, an affinity tag is a polypeptide segment that facilitates isolation, purification or detection of the fusion protein containing the affinity tag. In principle, any peptide or protein for which an antibody or other specific binding agent is available can be used as an affinity tag. Representative affinity tags include a poly-histidine tract, protein A (Nilsson, et al., EMBO J. 4:1075, (1985); Nilsson, et al., Methods Enzymol. 198:3, (1991)), glutathione S transferase (Smith et al., Gene 67:31 (1988)), maltose binding protein (Kellerman et al., Methods Enzymol, 90:459-463 (1982); Guan, et al., Gene 67:21-30 (1987)), Glu-Glu affinity tag (Grussenmeyer, et al., Proc. Natl. Acad. Sci. USA 82:7952-4 (1985); see oNDEPHO-1R), substance P, Flag™ peptide (Hopp, et al., Biotechnology 6:1204-10 (1988)), streptavidin binding peptide, thioredoxin, ubiquitin, cellulose binding protein, T7 polymerase, or other antigenic epitope or binding domain. See, in general, Ford, et al., Protein Expression and Purification 2:95-107 (1991). DNAs encoding affinity tags are available from commercial suppliers (e.g., Pharmacia Biotech, Piscataway, N.J.; New England Biolabs, Beverly, Mass.; and Eastman Kodak, New Haven, Conn.).

As in the case of the amino acid extension, the affinity tag may be situated at the N-terminal, C-terminal, or both N-terminal and C-terminal with respect to the biologically active polypeptide sequence.

The present invention is also directed to a method of making the protein conjugates. The method involves culturing a cell transformed with a chimeric DNA molecule encoding the protein conjugate under conditions whereby the DNA is expressed, thereby producing the protein conjugate; and extracting an expression product of the chimeric DNA molecule from the cell or culture medium (or a milieu from the cell culture). In contrast to protein conjugates formed by chemical means, e.g., the commercial product NEULASTA (PEG-G-CSF, which is a covalent conjugate of recombinant methionyl human G-CSF and monomethionyl polyethylene glycol), the conjugation in the present invention is performed recombinantly as opposed to through physical or chemical means, resulting in the production of the biologically active protein and the polypeptide as components of a continuous protein. A linker, e.g., about 10-20 amino acids in length, may be used to join. the protein with the amino acid extension.

The chimeric DNA molecule includes a gene or polynucleotide fragment that encodes a protein portion and one or more gene fragments e.g., oligonucleotides that together encode the polypeptide or amino acid extension. Oligonucleotides encoding the peptide motifs contained in the amino acid extension (and which encode the peptide motifs specifically disclosed herein) are set forth in Table 7, (The one-letter symbols used in Table 7 are explained in Table 8.) The DNA molecules may further contain fragments that encode affinity tags, linkers, as well as 5' and 3' regulatory elements. The gene or polynucleotide that encodes a protein portion may be any gene or polynucleotide known to encode the desired protein or polypeptide of the protein portion. Such genes and polynucleotides, and the printers used to generate them, are protein or polypeptide specific and well known in the art. The ligated oligonucleotides encoding the polypeptide portion may be produced according to procedures set forth above and described in Example 1. The oligonucleotides may be of any length, but are preferably designed to avoid the use of repetitive DNA sequences that are known to inhibit transcription. For instance, ligated oligonucleotides containing combinations of two glutamate codons are less likely to adopt a structural configuration that impedes gene expression than a polynucleotide made up of only one glutamate codon. The chimeric DNA molecule encoding the protein conjugate of the present invention may be engineered to contain codons encoding methionine (M) and/or proline (P) amino acid at its 5' end to facilitate expression.

The conjugates of the present invention are made via standard recombinant techniques in molecular biology, in some embodiments, a gene or polynucleotide encoding the biologically active protein is first cloned into a construct, e.g., a plasmid or other vector. Then, the oligonucleotides that encode the repeating units of the polypeptide portion are cloned into the construct through a ligation or multimetization scheme, in which the oligonucleotides are ligated together to form a polynucleotide that encodes the polypeptide portion. In this manner, the oligonucleotides are added to the gene or polynucleotide that encodes the protein portion, thereby producing the chimeric DNA molecule within the construct. As an option, the chimeric DNA molecule may be transferred or cloned into another construct that is a more appropriate expression vector. At this point, a host cell capable of expressing the chimeric DNA molecule is transformed with the chimeric DNA molecule. The transformation may occur with or without the utilization of a carrier, such as an expression vector. Then, the transformed host cell is cultured under conditions suitable for expression of the chimeric DNA molecule, resulting in the encoding of the protein conjugate.

Methods of ligation or multimerization useful in the present invention are well known. See, Joseph Sambrook, et al., Molecular Cloning: A Laboratory Manual, $2^{nd}$ ed., 1.53 (Cold Spring Harbor Laboratory Press 1989).

The cloning process may take place through "directional cloning", which is well known in the art. Directional cloning refers to the insertion of a polynucleotide into a plasmid or vector in a specific and predefined orientation. Once cloned into a vector, a polynucleotide sequence can be lengthened at its 3' end or other polynucleotides inserted at its 5' and/or 3' ends. Such a design provides an efficient and relatively easy way to create large polymers without having to perform multiple rounds of ligation. The vector preferably contains restriction sites upstream of a cloned polynucleotide, but downstream of regulatory elements required for expression to facilitate the insertion of the second polynucleotide.

To facilitate directional cloning, "adapter oligonucleotides" may be ligated to the 5' and 3' ends of the chimeric DNA molecule encoding the protein conjugate. Preferably, the adapters contain restriction sites that are compatible with those present in the expression vector. The 3' adapter oligonucleotide may also comprise a stop codon to designate the end of the encoding sequence to which it is ligated. The oligonucleotides encoding the polypeptide portion are preferably added in excess of the adapter oligonucleotides to increase the likelihood that a long polynucleotide is generated after ligation.

The methodology is not limited to any particular cloning strategy. The skilled artisan may use any variety of cloning strategies to produce a construct that comprises a chimeric DNA molecule of the present invention.

The chimeric DNA molecule can be introduced into the host cells in accordance with known techniques well known to those skilled in the art. These techniques include, but are not limited to, transformation using calcium phosphate coprecipitated chimeric DNA molecules, lipidic reagent cotransfection (i.e., Lipofectamine™), electroporation, transduction by contacting the cells with a virus, or microinjection of the chimeric DNA molecules into the cells. The host cell can be a higher eukaryotic cell, such as a mammalian cell, or a lower eukaryotic cell, such as a yeast cell, or the host cell can be a prokaryotic cell, such as a bacterial cell. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

A wide variety of host/expression vector combinations are employed in expressing the protein conjugates of the present invention. Generally, recombinant expression vectors will include origins of replication and selectable markers permitting transformation of the host cell dihydrofolate reductase or neomycin resistance for eukaryotic cell culture, or such as tetracycline or ampicillin resistance in *E. coli*, or the *S. cerevisiae* TRP1 gene), and a promoter derived from a highly-expressed gene to direct transcription of a downstream structural sequence. Such promoters can be derived from operons encoding glycolytic enzymes such as 3-phosphoglycerate kinase (PGK), A-factor, acid phosphatase, or heat shock proteins, among others. The heterologous structural sequence is assembled in appropriate phase with translation initiation and termination sequences, and in some embodiments, a leader sequence capable of directing secretion of translated protein conjugate. The vector will further comprise an origin of replication to ensure maintenance of the vector and to, if desirable, provide amplification within the host.

Useful expression vectors that can be used include, for example, segments of chromosomal, non-chromosomal and synthetic DNA sequences. Suitable vectors include, but are not limited to, derivatives of SV40 and pcDNA. and known bacterial plasmids such as col EI, pCR1, pBR322, pMal-C2, pET, pGEX as described by Smith, et al., Gene 67:31-40 (1988), pMB9 and derivatives thereof, plasmids such as RP4, phage DNAs such as the numerous derivatives of phage I such as NM989, as well as other phage DNA such as M13 and filamentous single stranded phage DNA; yeast plasmids such as the 2 micron plasmid or derivatives of the 2 m plasmid, as well as centomeric and integrative yeast shuttle vectors; vectors useful in eukaryotic cells such as vectors useful in insect or mammalian cells; vectors derived from combinations of plasmids and phage DNAs, such as plasmids that have been modified to employ phage DNA or the expression control sequences; and the like. The requirements are that the vectors are replicable and viable in the host cell of choice. Low- or high-copy number vectors may be used as desired.

For example in a baculovirus expression system, both non-fusion transfer vectors, such as, but not limited to pVL941 (BamHI cloning site, available from Summers, et al., Virology 84:390-402 (1978)), pVL1393 (BamHI, SmaI, XbaI, EcoRI, NotI, XmaIII, BglII and PstI cloning sites; Invitrogen), pVL1392 (BglII, PstI, NotI, XmaIII, EcoRI, XbalI, SmaI and BamHI cloning site; Summers, et al., Virology 84:390-402 (1978) and Invitrogen) and pBlueBacIII (BamHI, BglII, PstI, NcoI and HindIII cloning site, with blue/white recombinant screening, Invitrogen), and fusion transfer vectors such as, but not limited to, pAc700 (BamHI and KpnI cloning sites, in which the BamHI recognition site begins with the initiation codon; Summers, et al., Virology 84:390-402 (1978)), pAc701 and pAc70-2 (same as pAc700, with different reading frames), pAc360 (BamHI cloning site 36 base pairs downstream of a polyhedrin initiation codon; Invitrogen (1995)) and pBlueBacHisA, B, C (three different reading frames with BamHI, BglII, PstI, NcoI and HindIII cloning site, an N-terminal peptide for ProBond™ purification and blue/white recombinant screening of plaques; Invitrogen (220) can be used.

Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements. Mammalian expression vectors contemplated for use in the invention include vectors with inducible promoters, such as the dihydrofolate reductase promoters, any expression vector with a DHFR expression cassette or a DHFR/methotrexate co-amplification vector such as pED (PstI, SalI, SbaI, Sinai and EcoRI cloning sites, with the vector expressing both the cloned gene and DHFR; Randal J. Kaufman, 1991, Randal J. Kaufman, Current Protocols in Molecular Biology, 16, 12 (1991)). Alternatively a glutamine synthetase/methionine sulfoximine co-amplification vector, such as pEE14 (HindIII, XbalI, SmaI, SbaI, EcoRI and BclI cloning sites in which the vector expresses glutamine synthetase and the cloned gene; Celltech). A vector that directs episomal expression under the control of the Epstein Barr Virus (EBV) or nuclear antigen (EBNA) can be used such as pREP4 (BamHI, SfiI, XhoI, NotI, NheI, HindIII, NheI, PvuII and KpnI cloning sites, constitutive RSV-LTR promoter, hygromycin selectable marker; Invitrogen), pCEP4 (BamHI, XhoI, NotI, NheI, HindIII, NheI, PvuII and KpnI cloning sites, constitutive hCMV immediate early gene promoter, hygromycin selectable marker; Invitrogen), pMEP4 (KpnI, PvuI, NheI, HindIII, NotI, XhoI, SfiI, BamHI cloning sites, inducible methallothionein IIa gene promoter, hygromycin selectable marker, Invitrogen), pREP8 (BamHI, XhoI, NotI, HindIII, NheI and KpnI cloning sites, RSV-LTR promoter, histidinol selectable marker; Invitrogen), pREP9 (KpnI, NheI, HindIII, NotI, XhoI, SfiI, BamHI cloning sites, RSV-LTR promoter, G418 selectable marker; Invitrogen), and pEBVHis (RSV-LTR promoter, hygromycin selectable marker, N-terminal peptide purifiable via ProBond™ resin and cleaved by enterokinase; Invitrogen).

Selectable mammalian expression vectors for use in the invention include, but are not limited to, pRc/CMV (HindIII, BstXI, NotI, SbaI and ApaI cloning sites, G418 selection, Invitrogen), pRc/RSV (HindII, SpeI, BstXI, NotI, XbaI cloning sites, G418 selection, Invitrogen) and the like. Vaccinia virus mammalian expression vectors (see, for example, Randall J. Kaufman, Current Protocols in Molecular Biology 1612 (Frederick M. Ausubel, et al., eds. Wiley 1991) that can be used in the present invention include, but are not limited to, pSC11 (SmaI cloning site, TK- and β-gal selection), pMJ601 (SalI, SmaI, AflI, NarI, BspMII, BamHI, ApaI, NheI, SacII, KpnI and HindIII cloning sites; TK- and β-gal selection), pTKgptF1S (EcoRI, PstI, SalII, AccI, HindII, SbaI, BamHI and Hpa cloning sites, TK or XPRT selection) and the like.

Yeast expression systems that can also be used in the present include, but are not limited to, the non-fusion pYES2 vector (XbaI, SphI, ShoI, NotI, GstXI, EcoRI, BstXI, BamHI, SacI, KpnI and HindIII cloning sites, Invitrogen), the fusion pYESHisA, B, C (XbalI, SphI, ShoI, NotI, BstXI, EcoRI, BamHI, SacI, KpnI and HindIII cloning sites, N-terminal peptide purified with ProBond™ resin and cleaved with enterokinase; Invitrogen), pRS vectors and the like.

One particularly preferred vector for use in the present invention is the plasmid pCE2. The pCE2 plasmid may be obtained by any method known in the art. One such method, which was utilized in Example 2.A., is described in Leung, et al., Proc. Natl. Acad. Sci. USA 92:4813-4817 (1995).

In a preferred embodiment, the chimeric DNA molecules can be inserted into an expression vector that already contains the necessary elements for the transcription and translation of the inserted chimeric DNA molecule.

In addition, the expression vector containing the chimeric DNA molecule may include drug selection markers. Such markers aid in cloning and in the selection or identification of vectors containing chimeric DNA molecules. For example, genes that confer resistance to neomycin, puromycin, hygromycin, dihydrofolate reductase (DHFR), guanine phosphoribosyl transferase (GPT), zeocin, and histidinol are useful selectable markers. Alternatively, enzymes such as herpes simplex virus thymidine kinase (tk) or chloramphenicol acetyltransferase (CAT) may be employed. Immunologic markers also can be employed. Any known selectable marker may be employed so long as it is capable of being expressed simultaneously with the nucleic acid encoding a gene product. Further examples of selectable markers are well known to one of skill in the art and include reporters such as enhanced green fluorescent protein (EGFP), beta-galactosidase (β-gal) or chloramphenicol acetyltransferase (CAT).

Consequently, mammalian and typically human cells, as well as bacterial, yeast, fungi, insect, nematode and plant cells can used in the present invention as host cells and may be transformed by the expression vector as defined herein. In some cellular hosts, such as mammalian cells, the cell containing the chimeric DNA molecule may be "isolated" in that it is removed from its original environment (e.g., the natural environment if it is naturally occurring). In other embodiments, such as plants, the cells do not have to be isolated in that the whole plant may be used rather than a culture of plant cells or parts.

Examples of suitable cells include, but are not limited to, VERO cells, HELA cells such as ATCC No. CCL2, CHO cell lines such as ATCC No. CCL61, COS cells such as COS-7 cells and ATCC No. CRL 1650 cells, W138, BHK, HepG2, 3T3 such as ATCC No. CRL6361, A549, PC12, K562 cells, 293 cells, Sf9 cells such as ATCC No. CRL1711 and Cv1 cells such as ATCC No. CCL70.

Other suitable cells that can be used in the present invention include, but are not limited to, prokaryotic host cells strains such as *Escherichia coli*, (e.g., strain DH5-α), *Bacillus subtilis, Salmonella typhimurium*, or strains of the genera of *Pseudomonas, Streptomyces* and *Staphylococcus*. Further suitable cells that can be used in the present invention include yeast cells such as those of *Saccharomyces* such as *Saccharomyces cerevisiae*.

Host cells containing the polynucleotides of interest can be cultured in conventional nutrient media (e.g., Ham's nutrient mixture) modified as appropriate for activating promoters, selecting transformants or amplifying genes. The culture conditions, such as temperature, pH and the like, are those previously used with the host cell selected for expression, and will be apparent to the ordinarily skilled artisan. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, all of which are well known to those skilled in the art. Embodiments that involve cell lysis may entail use of a buffer that contains protease inhibitors that limit degradation after expression of the chimeric DNA molecule. Suitable protease inhibitors include leupeptin, pepstatin or aprotinin. The supernatant then may be precipitated. in successively increasing concentrations of saturated ammonium sulfate.

The protein conjugates product may be purified via one or more techniques. Typically, purification entails combinations of individual procedures such as gel filtration, affinity purification, salt fractionation, ion exchange chromatography, size exclusion chromatography, hydroxylapatite adsorption chromatography, hydrophobic interaction chromatography and gel electrophoresis. Protein refolding steps can be used, as necessary, in completing configuration of the protein conjugate. High performance liquid chromatography (HPLC) is often useful for final purification steps. See, in general, Robert K. Scopes, Protein Purification: Principles and Practice (Charles R. Castor, ed., Springer-Verlag 1994) and Joseph Sambrook, Molecular Cloning: A Laboratory Manual, $2^{nd}$ edition (Cold Spring Harbor Laboratory Press 1989). Examples of multi-step purification separations are also described in Baron, et al., Crit. Rev. Biotechnol. 10:179-90 (1990) and Below, et al., J. Chromatogr. A. 679:67-83 (1994).

The conjugates are tested prior to use to determine whether they exhibit modified plasma half-life compared to the unconjugated protein. For example, in experiments conducted with G-CSF and various amino acid extensions such as (NNT), Applicants found that the half-life was increased in one case, and in other cases, was decreased. The tests may be conducted in accordance with standard techniques in pharmacokinetics, as shown in example 3. This procedure entails administration of a predetermined dose of the conjugate to an animal, preferably a laboratory animal such as a rodent, e.g., mouse, collect plasma from the animal at predetermined intervals, and analyze the plasma e.g., via Enzyme-Linked Immunosorbent Assay ("ELISA"), to determine concentration of the conjugate, until concentration was no longer measurable. The half-life may be calculated via a non compartmental pharmacokinetic analysis (e.g., using WINNonLin software version 4.1). In addition to the last time at which the conjugate concentration was measurable ($t_f$), the analysis includes observation or calculation of the following main parameters: $\lambda_z$, apparent terminal rate constant associated to the apparent terminal phase, estimated by linear regression analysis of the logarithm of the plasma concentrations versus time in the monoexponential terminal part of the curve, $t_{1/2,z}$, apparent terminal half-life, calculated according to the following equation: $t_{1/2,z}=\ln(2)/\lambda_z$; AUC, area under the plasma concentration-time curve from time zero to infinity; AUC/D, area under the plasma concentration-time curve per unit of dose; MRT, mean residence time calculated as the ratio between the area under the first moment curve, AUMC, and AUC; CL, systemic clearance, calculated as CL=D/AUC; and $V_{ss}$, steady state volume of distribution, calculated as $V_{ss}$=CL*MRT.

A further aspect of the present invention relates to a composition comprising the protein conjugate and a carrier. Broadly, the carrier may be a culture medium or a matrix (e.g., a purification matrix). In some embodiments, the carrier is a pharmaceutically acceptable carrier, in which case the composition is useful for preventing or treating disorders and/or diseases in a human or animal, most preferably in a mammal, or for diagnostic purposes. As an active ingredient of the composition, the protein conjugate is preferably in a soluble form.

Generally, the composition comprises a pharmaceutically effective amount of the protein conjugate which achieves the desired effect e.g., therapeutic or diagnostic. Pharmaceutically effective amounts can be estimated from cell culture assays. For example, a dose can be formulated in animal models to achieve a circulating concentration range that includes or encompasses a concentration point or range having the desired effect in an in vitro system. See, e.g., Molineux, et al., Exp. Hematol. 27:1724-34 (1999). This information can thus be used to accurately determine the doses in other mammals, including humans and animals. In general, dosage amounts range from about 1 ng/kg to about 10 mg/kg based on weight of the subject.

Toxicity and therapeutic efficacy of such compounds can be determined by standard pharmaceutical procedures in cell cultures or in experimental animals. See, e.g., Molineux, et al., Exp. Hematol. 27:1724-34 (1999). For example, the LD50 (the dose lethal to 50% of the population) as well as the ED50 (the dose therapeutically effective in 50% of the population) can be determined using methods known in the art. The dose ratio between toxic and therapeutic effects is the therapeutic index that can be expressed as the ratio between LD50 and ED50 compounds that exhibit high therapeutic indices.

The data obtained from the cell culture and animal studies can be used in formulating a range of dosage of such compounds which lies preferably within a range of circulating concentrations that include the ED50 with little or no toxicity.

The compositions can be administered via any suitable route such as locally, orally, systemically, intravenously, intramuscularly, mucosally, transdermally (e.g., via a patch). They may be encapsulated in liposomes, microparticles, microcapsules, nanoparticles and the like. Techniques for formulating and administering biologically active polypeptides are also disclosed in Remington: The Science and Practice of Pharmacy (Alfonso R. German), et al., eds. Philadelphia College of Pharmacy and Science 2000).

In order to fully illustrate the present invention and advantages thereof, the following specific examples are given, it being understood that the same are intended only as illustrative and in no way limitative.

Example 1

Cloning of Chimeric DNA Molecule

For ease of downstream protein purification, it was decided that the G-CSF-polymer proteins were secreted into the cell culture medium. Prior experience using bacterial (ST2) secretion signals with various cytokine-polymer constructs showed low secretion efficiency in both prokaryotic and eukaryotic systems. However, the use of the *Schizosaccharomycen pombe* secretion signal sequence of the pho1+ acid phosphatase (PHO) for the secretion of heterologous proteins (GIFT and HPV 16 E7) into a medium was known. Therefore, this secretion signal was tested with the G-CSF-polymer constructs described below in a CHO cell expression system. Also described below are the vectors that were synthesized for the production of G-CSF-polymer constructs and expression of G-CSF-polymers.

1A. Production of PHO×pBSK Construct

PRO×pBSK Construct

The first construct synthesized was simply the PRO leader sequence cloned into the bacterial cloning vector pBSK. The amino acid sequence of the PHO secretion signal is listed below,

```
                                      (SEQ ID NO: 154)
     M F L Q N L F L G F L A V V C A N A
```

The PHO secretion signal was synthesized by fusing two sets of complementary DNA oligonucleotides together and cloning them into pBSK. The most important consideration that went into the design of the oligonucleotides was that the fusion of the leader sequence to the N-terminus of the G-CSF-polymer be direct, without any intervening sequence. This ensured that the entire secretion signal was clipped from the molecule during processing, resulting in a secreted form of G-CSF with no amino-terminal modification when compared to naturally occurring and clinically available versions of G-CSF. By preparing the constructs in this manner, not only could direct comparisons to G-CSF and PEG-G-CSF be made, but this also limited any potential immunogenicity by introducing additional amino acids into the recombinant G-CSF protein. By incorporating restriction sites into the oligonucleotides for cloning the PHO leader into pBSK, as well as the subsequent cloning G-CSF into PHO×pBSK, these requirements were satisfied. The oligonucleotides that were used are listed below.

```
oNDEPHO-1F:
                                     (SEQ ID NO: 155)
5'-GGCCGCCATATGTTCTTGCAAAATTTATTCCTTGGCT-3'

oNDEPHO-1R:
                                     (SEQ ID NO: 156)
5'-CCAAAAAGCCAAGGAATAAATTTTGCAAGAACATATGGC-3'

oNDEPHO-2F:
                                     (SEQ ID NO: 157)
5'-TTTTGGCCGTTGTTTGCGCAAACGCGTCCCGCAGGTG-3'

oNDEPHO-2R:
                                     (SEQ ID NO: 158)
5'-GATCCACCTGCGGGACGCGTTTGCGCAAACAACGG-3'
```

A diagram of the PHO×pBSK vector is shown in FIG. 1. The PRO leader (PhoA) was cloned into pBSK using NotI and BamHI. The sequence for mature G-CSF was cloned into this construct utilizing the BspMI and BamHI sites. This vector confers ampicillin resistance (bla) when grown in bacteria.

Method of Construction

Complementary pairs of oligonucleotides (oNDEPHO-1F and oNDEPHO-1R) and (oNDEPHO-2F and oNDEPHO-2R) were phosphorylated using T4 Polynucleotide Kinase (PNK). The T4 PNK was heat-inactivated and the oligonucleotide pairs were allowed to slowly anneal on ice. The reactions were diluted in TE and used in a ligation with pBSK. previously digested using NotI and BamHI. Ligation products were electroporated into Top10 competent cells and grown on LB-ampicillin plates. Minipreps were performed on ampicillin resistant colonies to isolate DNA and diagnostic digests identified putative clones. Sequence analysis determined which of the putative clones were correct.

1.B. Production of PRO-G-CSF-NN×pBSK Construct

PHO-G-CSF-NN×pBSK Construct

This construct resulted from the cloning of PCR amplified material corresponding to the coding sequence of mature G-CSF into the PHO×pBSK vector using BspMI and BamHI. As stated previously, the oligonucleotides used for this purpose were designed to ensure that the junction between PRO and G-CSF had no intervening sequence by utilizing the restriction enzyme BspMI. Furthermore, the C-terminus of G-CSF had a direct fusion of two asparagine residues (NN) and restriction sites for the enzymes BbsI and BamHI. BbsI was subsequently utilized to directly add the NNT polymer to the C-terminus of G-CSF, while BamHI was used to clone GCSF-NN into the vector.

The oligonucleotides that were synthesized to amplify G-CSF are as follows:

```
oBspMIGCSF:
                                     (SEQ ID NO: 159)
5'-CGATCGACCTGCAAGTCGCGACTCCGCTGGGTCCAGCTA-3'

oGCSFBbsBam:
                                     (SEQ ID NO: 160)
5'-CGGGATCCGAAGACGTGTTGTTAGGCTGGGCAAGGTGGC-3' 3'
```

Figure 2:
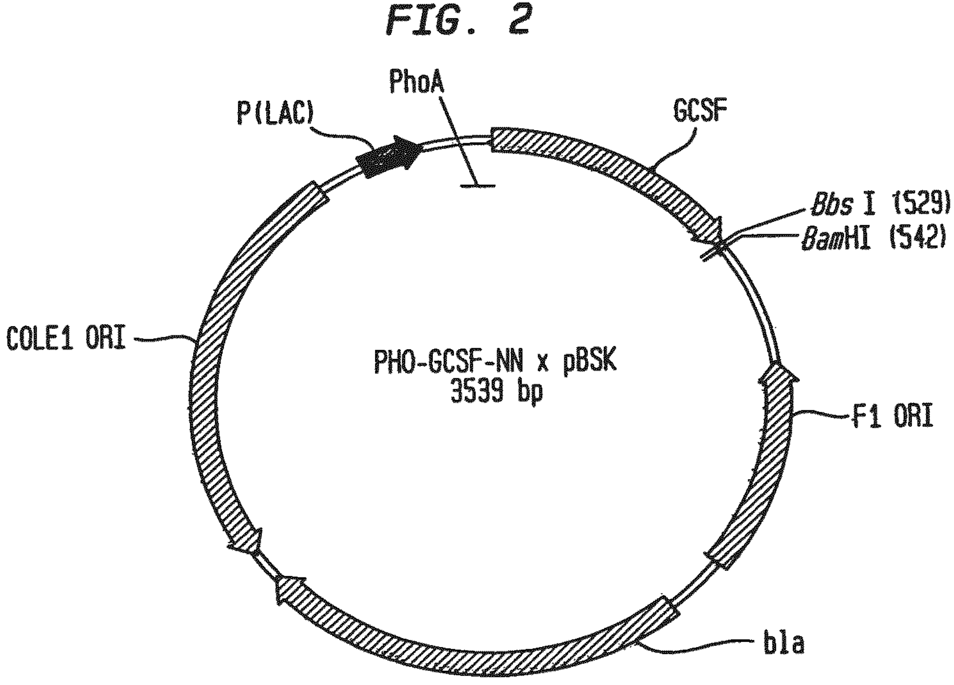
FIG. 2 is a schematic representation of the RHO-G-CSF-NN×pBSK vector.

A diagram of the PHO-G-CSF-NN×pBSK vector is shown in FIG. 2. The sequence for mature G-CSF-NN was cloned into PHO×pBSK using BspMI (destroyed) and BamHI. The subsequent addition of an NNT polymer utilized the BbsI and BamHI sites indicated on the plasmid map. This vector confers ampicillin resistance (bla) when grown in bacteria.

Method of Construction

G-CSF was amplified by PCR using oBspMIGCSF and oGCSFBbsBam oligonucleotides. The ≈520 bp band corresponding to mature G-CSF was excised from an agarose gel and purified. The purified fragment was digested with BspMI and BamHI, purified and ligated into PHO×pBSK cut with the same enzymes. The ligation products were electroporated into Top10 competent cells and grown on LB-ampicillin plates. Minipreps were performed on ampicillin resistant colonies to isolate DNA and diagnostic digests identified putative clones. Sequence analysis determined which of the putative clones were correct.

1.C. Production of PHO-G-CSF-NNT65×pBSK Construct (NNT65 Disclosed as SEQ ID NO: 1)

PHO-G-CSF-NNT65×pBSK Construct (NNT65 Disclosed as SEQ ID NO: 1)

The amino acid composition of this polymer encodes for the consensus mammalian N-linked glycosylation site, N-X-(S/T). Therefore, the polymer may be glycosylated on the threonine residues of the polymer extension when this construct is expressed in CHO cells. The expectation was that the polymeric increase in translated product size and posttranslational modification would modulate the pK parameters of G-CSF, conferring upon the protein-enhanced half-life in serum without decreasing its biological activity.

The construction of this polymer was achieved using an oligonucleotide ligation/multimerization scheme. By cutting the PHO-G-CSF-NN×pBSK construct with BbsI, a four base underhang (GTTG) was created in the two asparagines residues added to the C-terminus of G-CSF. By designing complementary sets of oligonucleotides that code for repeating NNT triplets as well as anneal to the GTTG underhang, it was possible to multimerize the oligonucleotides that code for 9 amino acids into longer chains. Short adaptors containing a stop codon, a BbsI site for future extension of the polymer and a BamHI site were added in low ratios to terminate the multimerization and allow for coning of the BbsI-BamHI polymer fragment into PHO-G-CSF-NN×pBSK.

The oligonucleotides used to synthesize the NNT65 polymer (NNT65 disclosed as SEQ ID NO: 1) are listed below:

Polymer Backbone Oligonucleotides

```
o3NNTF:
                                  (SEQ ID NO: 161)
5'-CAACACCAACAATACCAACAATACAAA-3'

o3NNTR:
                                  (SEQ ID NO: 162)
5'-GTTGTTTGTATTGTTGGTATTGTTGGT-3'
```

Adaptor Oligonucleotides

```
oDent3F:
                                  (SEQ ID NO: 163)
5'-CAACTAGTCTTCG-3'

oDent3R:
                                  (SEQ ID NO: 164)
5'-GATCCGAAGACTA-3'
```

The following sequence (NTNNTNNTN) (SEQ ID NO: 165) was the repeating unit of the NNT polymer that was produced using the polymer backbone oligonucleotides of o3NNTF and o3NNTR, which show a CAAC overhang and GTTG underhang respectively that were used to multimerize the polymer.

```
                                      (SEQ ID NO: 165)
   N   T   N   N   T   N   N   T   N

                             (o3NNTF)(SEQ ID NO: 166)
5'-C AAC ACC AAC AAT ACC AAC AAT ACA AA-3'

                             (o3NNTR)(SEQ ID NO: 167)
3'-TGG TTG TTA TGG TTG TTA TGT TTG TTG-5'
```

The following is the terminating adaptor molecule that completed the polymer and included a stop codon, BbsI site for future extension of the polymer and a BamHI site that is necessary for cloning.

Terminating Adaptor Molecule

```
         N   *
                            (oDent3F)(SEQ ID NO: 168)
5'-C AAC TAG TCT TCG-3'

                            (oDent3R)(SEQ ID NO: 169)
3'-ATC AGA AGC CTA G-5'
BbsI BamHI
```

BbsI BamHI

Figure 3:
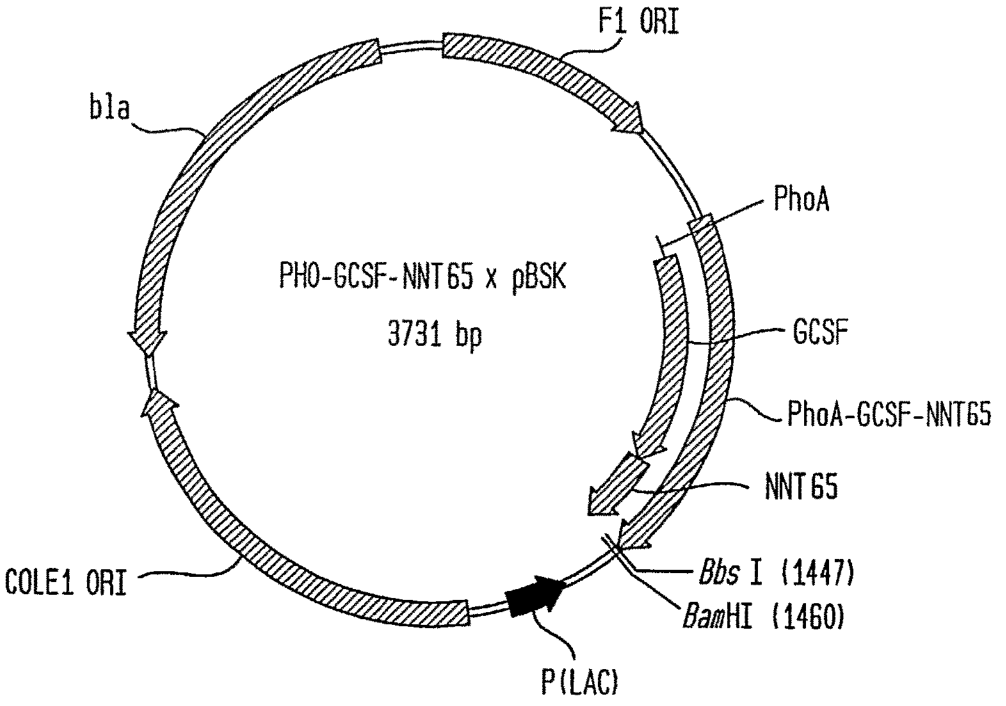
FIG. 3 is a schematic representation of the PHO-G-CSF-NNT65×pBSK, vector (NNT65 disclosed as SEQ ID NO: 1).

A diagram of the PHO-G-CSF-NNT65×pBSK vector (NNT65 disclosed as SEQ ID NO: 1) is shown in FIG. 3. The addition of NNT65 polymer (NNT65 disclosed as SEQ ID NO: 1) utilized the BbsI site (destroyed) that was located at the C-terminus of G-CSF and BamHI. As shown in FIG. 3, the BbsI site was regenerated at the end of the NNT65 polymer (NNT65 disclosed as SEQ ID NO: 1) for future extension of length. This vector confers ampicillin resistance (bla) when grown in bacteria.

Method of Construction

Complementary pairs of polymer backbone oligonucleotides (o3NNTF and o3NNTR) and adaptor oligonucleotides (oDent3F and oDent3R) were phosphorylated using T4 PNK. The T4 PNK was heat-inactivated and the oligonucleotide pairs were allowed to slowly anneal on ice. Polymer multimerization was performed by mixing polymer and adaptor duplexes at 20:1 and 40:1 ratios with T4 Ligase. The T4 ligase was heat-inactivated and the entire ligation reactions were digested with BamHI overnight. Both reactions were precipitated and ran on an acrylamide gel. Material between 250 bp-800 bp was excised and gel purified.

This material was used in a ligation with PHO-G-CSF-NN×pBSK that had been digested with BbsI and BamHI Chemically competent Stb12 cells were transformed with the ligation products and grown on LB-ampicillin plates. Minipreps were performed to isolate DNA and diagnostic digests identified putative Clones. Sequence analysis determined which of the putative clones were correct.

The longest clone isolated from this strategy was PHO-G-CSF-NNT65×pBSK (NNT65 disclosed as SEQ ID NO: 1).

1.D. Production of PHO-G-CSF-NNT155×pBSK Construct (NNT155 Disclosed as SEQ ID NO: 2)

PHO-G-CSF-NNT155×pBSK Construct (NNT155 Disclosed as SEQ ID NO: 2)

The construction of this clone required the addition of additional NNT residues to the PHO-G-CSF-NNT65×pBSK construct (NNT65 disclosed as SEQ ID NO: 1) using the same oligomerization scheme. The nucleotide composition of the oligonucleotides used in this extension was altered to identify the junction between the original polymer and the extension. These alterations maintained the original NNT composition of the polymer and utilized the same GTTG underhang and CAAC overhang strategy. By digesting PHO-GCSF-NNT65 (NNT65 disclosed as SEQ ID NO: 1) with BbsI and BamHI, it was possible to extend the length of the polymer using the same oligonucleotide multimerization strategy as before.

The oligonucleotides used to extend the NNT65 polymer (NNT65 disclosed as SEQ ID NO: 1) to NNT155 (NNT155 disclosed as SEQ ID NO: 2) are listed below:

Polymer Backbone Oligonucleotides

```
o3NNTextF:
                                  (SEQ ID NO: 170)
5'-CAACACCAATAATACCAACAATACAAA-3'

o3NNTextR:
                                  (SEQ ID NO: 171)
5'-GTTGTTTGTATTGTTGGTATTATTGGT-3'
```

Adaptor Oligonucleotides

```
oDent3F:
                                  (SEQ ID NO: 172)
5'-CAACTAGTCTTCG-3'

oDent3R:
                                  (SEQ ID NO: 173)
5'-GATCCGAAGACTA-3'
```

As with the production of the PHO-G-CSF-NNT65×pBSK Construct (NNT65 disclosed as SEQ ID NO: 1), NTNNTNNTN (SEQ ID NO: 165) was the repeating unit of the NNT polymer extension that was produced using the polymer backbone oligonucleotides of o3NNTextF and o3NNTextR, in which the CAAC overhang and GTTG underhang were still used to multimerize the polymer and the amino acid composition was unchanged from the original NNT65 polymer (NNT65 disclosed as SEQ ID NO: 1).

```
                                   (SEQ ID NO: 165)
    N   T   N   N   T   N   N   T   N

                      (o3NNTextF)(SEQ ID NO: 174)
5'-C AAC ACC AAT AAT ACC AAC AAT ACA AA-3'

                      (o3NNTextR)(SEQ ID NO: 175)
3'-TGG TTA TTA TGG TTG TTA TGT TTG TTG-5'
```

The above underlined nucleotides of o3NNTextF and o3NNTextR differed from the nucleotides in the same position in o3NNTF and o3NNTR respectively.

The following is the terminating adaptor molecule that completed the NNT155 polymer (NNT155 disclosed as SEQ ID NO: 2) and included the BamHI site necessary for cloning. oDent3F and oDent3R are the same oligonucleotides that were used for the initial NNT65 polymer (NNT65 disclosed as SEQ ID NO: 1).

Terminating Adaptor Molecule

```
          N   *
                (oDent3F)(SEQ ID NO: 176)
5'-C AAC TAG TCT TCG-3'

                (oDent3R)(SEQ ID NO: 177)
3'-ATC AGA AGC CTA G-5'
        BbsI BamHI
```

BbsI BamHI

Figure 4:
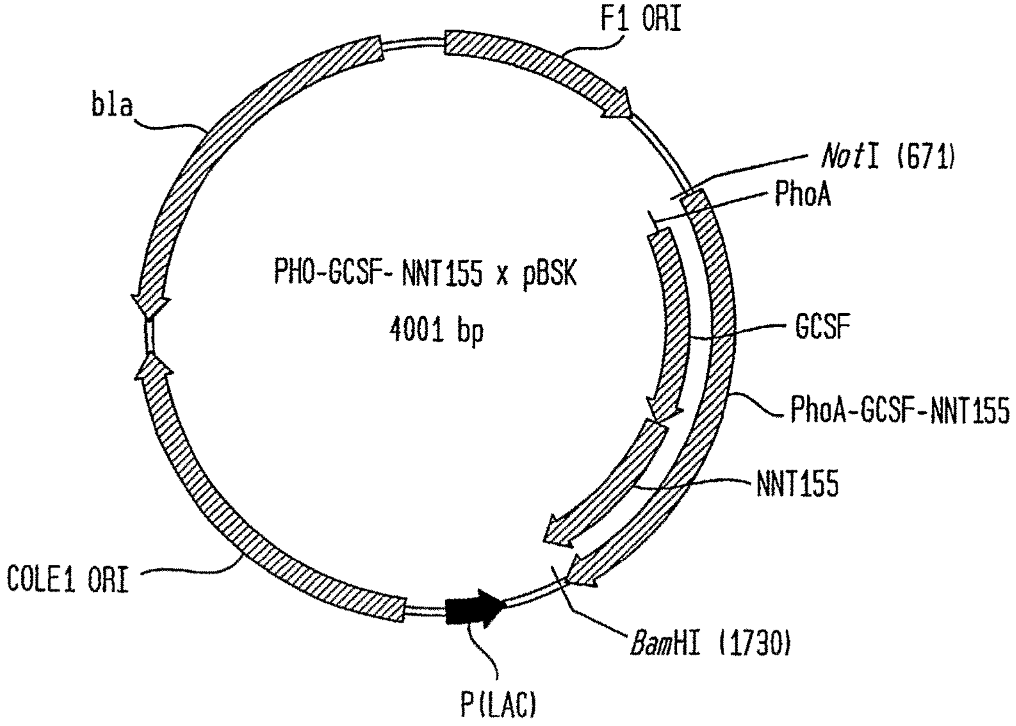
FIG. 4 is a schematic representation of the PHO-G-CSF-NNT155×pBSK vector (NNT155 disclosed as SEQ ID NO: 2).

A diagram of the PHO-G-CSF-NNT155×pBSK vector (NNT155 disclosed as SEQ ID NO: 2) is shown in FIG. 4. The extension of the NNT65 polymer (NNT65 disclosed as SEQ ID NO: 1) by 90AA utilized the BbsI site (destroyed) that was located at the C-terminus of PHO-G-CSF-NNT65×pBSK (NNT65 disclosed as SEQ ID NO: 1) and BamHI. It was noted that the BbsI site was regenerated at the end of the NNT155 (NNT155 disclosed as SEQ ID NO: 2) polymer for future extension of length. This vector confers ampicillin resistance (bla) when grown in bacteria.

Method of Construction

Complementary pairs of polymer backbone oligonucleotides o3NNTextF and o3NNTextR, and adaptor oligonucleotides oDent3F and oDent3R were phosphorylated using T4 PNK. The T4 PNK was heat-inactivated and the oligonucleotide pairs were allowed to slowly anneal on ice. Polymer oligomerization was performed by mixing polymer and adaptor duplexes at 20:1 and 40:1 ratios with T4 Ligase. The T4 Ligase was heat-inactivated and the entire ligation reactions were digested with BamHI overnight. Both reactions were precipitated and ran on an acrylamide gel. Material between 250 bp to 800 bp was excised and gel purified. This material ligated into PHO-G-CSF-NNT65×pBSK (NNT65 disclosed as SEQ ID NO: 1) digested with BbsI and BamHI. Chemically competent Stb12 cells were transformed with the ligation products and grown on LB-ampicillin plates. Minipreps were performed to isolate DNA and diagnostic digests identified putative clones. Sequence analysis determined which of the putative clones were correct.

The longest clone isolated from this strategy was PHO-G-CSF-NNT155×pBSK (NNT155 disclosed as SEQ ID NO: 2).

Example 2

Transformation of Host Cell and Expression of Chimeric DNA Molecule

2.A. Production of PHO-G-CSF-NNT155×pCE2 Construct (NNT155 Disclosed as SEQ ID NO: 2)

Preparation of Vector pCE2

The plasmid pCE2 was derived from the plasmid pREP7b, through the following manipulations. First, the 2000 bp EBNA coding region was deleted. Next, pBR322ori was replaced with pKS-ori. Then, the RSV promoter region was replaced by the CMV enhancer and the elongation factor-1a (EF-1a) promoter and intron.

The CMV enhancer was derived from a 380 bp XbaI-SphI fragment produced by the polymerase chain reaction (PCR) from pCEP4 (Invitrogen, San Diego, Calif.) using the following primers:

```
                                 (SEQ ID NO: 178)
5'-GGCTCTAGATATTAATAGTAATCAATTAC-3';
and

                                 (SEQ ID NO: 179)
5'-CCTCACGCATGCACCATGGTAATAGC-3'.
```

The EF-1a promoter and intron (Uetsuki, et al., J. Biol. Chem. 264:5791-5798 (1989)) were derived from a 1200 bp SphI-Asp718I fragment produced by PCR from human genomic DNA using the following primers:

```
                                 (SEQ ID NO: 180)
5'-GGTGCATGCGTGAGGCTCCGGTGC-3';
and

                                 (SEQ ID NO: 181)
5'-GTAGTTTTCACGGTACCTGAAATGGAAG-3'.
```

The two fragments were ligated into a XbaI/Asp718I digested vector derived from pREP7b to generate pCE2.

PHO-G-CSF-NNT155×pCE2 Construct (NNT155 Disclosed as SEQ ID NO: 2)

In order to express PHO-G-CSF-NNT155 (NNT155 disclosed as SEQ ID NO: 2) in mammalian cells, it was necessary to move the construct into the vector pCE2. This vector contained the minimal promoter and the first intron for the human elongation factor-1-α flanked by the immediate-early CMV enhancer. The vector also contained the hygromycin B resistance marker for mammalian selection.

Figure 5:
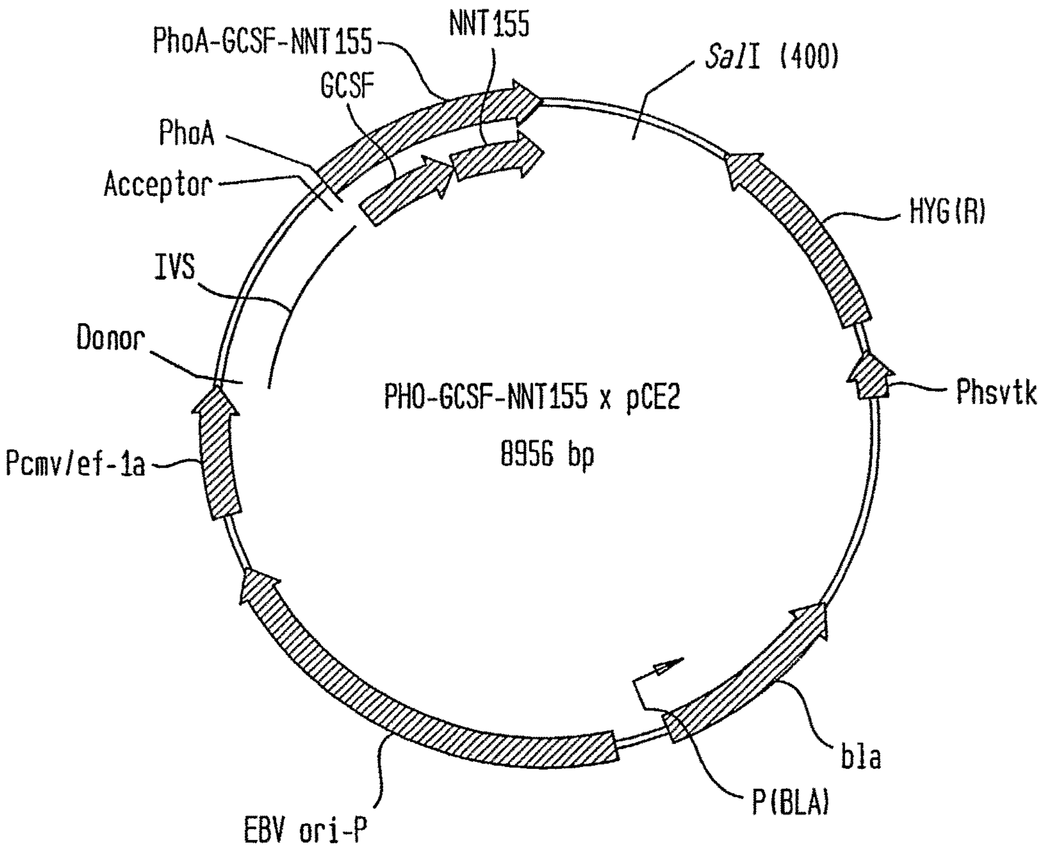
FIG. 5 is a schematic representation of the PHO-G-CSF-NNT155×pCE2 vector (NNT155 disclosed as SEQ ID NO: 2).

A diagram of the PHO-G-CSF-NNT155×pCE2 vector (NNT155 disclosed as SEQ ID NO: 2) is shown in FIG. 5. The promoter that drives expression in CHO cells is Pcmv/ef-1a. The vector was linearized for electroporation into CHO cells using SalI. This vector confers resistance to hygromycin B in mammalian cells and ampicillin resistance (bla) when grown in bacteria.

Method of Construction

This construct was produced by isolating and gel purifying the 1100 bp NotI-BamHI fragment from PHO-G-CSF-NNT155×pBSK (NNT155 disclosed as SEQ ID NO: 2). This material was ligated into pCE2 that had been digested with NotI and BamHI. Chemically competent Stb12 cells were transformed with the ligation products and grown on LB-ampicillin plates. Minipreps were performed to isolate DNA and diagnostic digests identified putative clones. Large-scale maxipreps were performed to isolate microgram quantities of the plasmid for CHO cell transformation.

2.B. Production of Transfectant Cell Lines

In order to produce the polymers described above, mammalian cells were used as host cells for expression. In this instance, Chinese hamster ovary (CHO) cell lines were chosen. CHO cells are widely used in the pharmaceutical industry to express recombinant protein therapeutics including G-CSF and EPO. As described below, expression cultures of G-CSF-polymer constructs in CHO cells were established.

Establishment of Adherent Cultures

The PHO-G-CSF-NNT155xpCE2 vector (NNT155 disclosed as SEQ ID NO: 2) was linearized using the enzyme Sari. The digest was precipitated and re-suspended in 50 μL of TE. One (1) μg of this plasmid was used in an electroporation along with $5\times10^6$ CHO cells. Adherent CHO cells were grown in Ham's Nutrient Mixture F-12 (F-12 Ham's media) containing 10% FBS. The cells were allowed to recover overnight, and the next day media containing 700 μg/mL of hygromycin B was added to begin selection of resistant cells. The media was changed every 2-3 days as needed over the course of 2-3 weeks. Bulk pools of resistant cells were isolated and passaged two additional times in the presence of hygromycin B.

Figure 6:
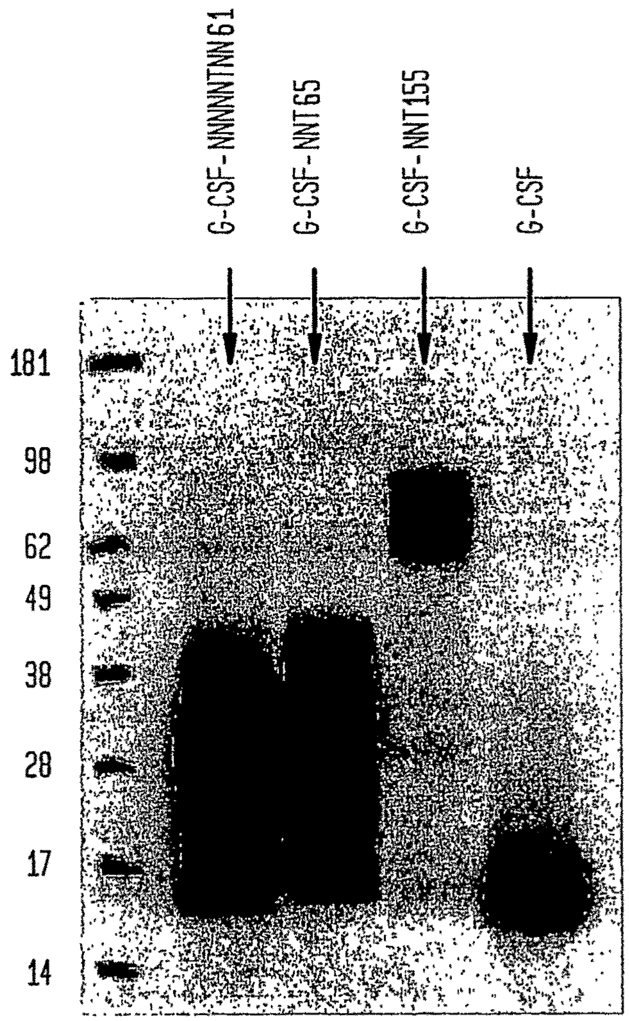
FIG. 6 is a Western blot of several different G-CSF-polypeptide conjugates and unconjugated G-CSF, NNT65, NNT155 and NNNNNTNN61 disclosed as SEQ ID NOS: 1-3, respectively.
Figure 7:
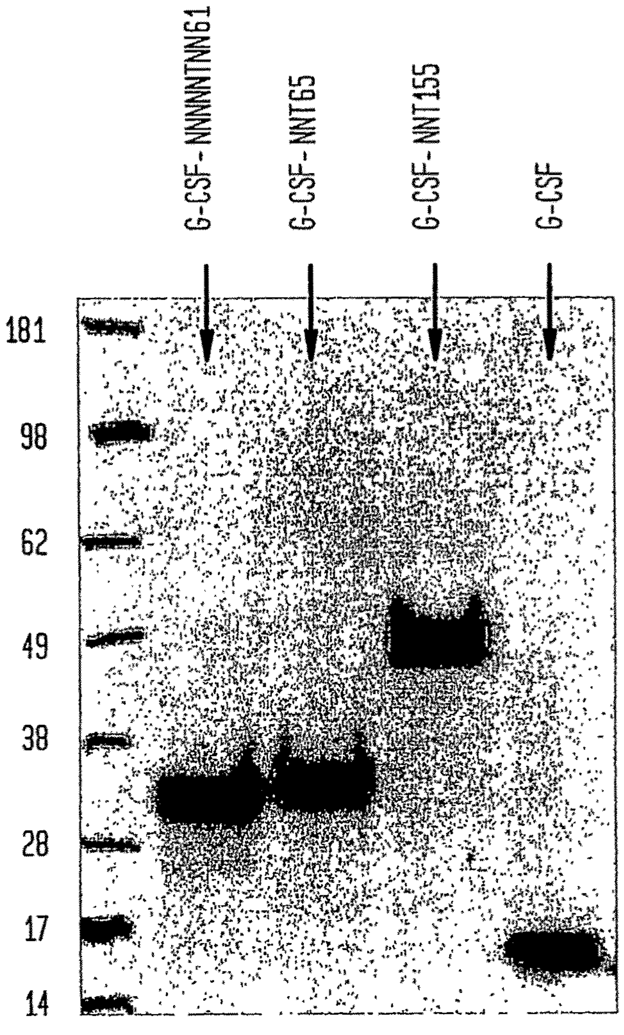
FIG. 7 is a Western blot of several different G-CSF-polypeptide conjugates and unconjugated G-CSF that were treated with PNGase F prior to electrophoresis. NNT65, NNT155 and NNNNNTNN61 disclosed as SEQ ID NOS: 1-3, respectively.

To test these cells for the secretion of PHO-G-CSF-NNT155 (NNT155 disclosed as SEQ ID NO: 2) into the media, the cells were grown in Ham's media containing low serum media (0.5%) for 3-5 days. The media was isolated and used in Western blots that were probed using a polyclonal antibody against G-CSF. The blots are reproduced in FIGS. 6 and 7. The difference between the blots is that the samples in FIG. 7 were additionally subjected to Peptide:N Glycosidase F (PNGase F) treatment. As shown in FIG. 6, the blots showed immunoreactive material migrating at apparent molecular weight≈95 kDa. As shown in FIG. 7, digestion of these same samples with PNGase F, a glycosidase that removes N-linked glycosylation chains, reduced the immunoreactive material to apparent molecular weight≈49 kDa. This corresponded approximately to the theoretical size of unmodified G-CSF-NNT155 protein (NNT155 disclosed as SEQ ID NO; 2). Native G-CSF migrates electrophoretically at ≈18 kDa; the addition of the NNT polymer to the C-terminus adds substantial mass to the recombinant, polymeric molecule. The expression also appeared quite stable; no appreciable proteolytic degradation was observed for the unpurified protein present in conditioned medium. Further, as shown in FIG. 7, the decrease in size of the constructs after PNGase F treatment suggested the recombinant protein constructs were subject to a substantial amount of glycosylation.

Establishment of Suspension Cultures

To facilitate purification of G-CSF-NNT155 (NNT155 disclosed as SEQ ID NO: 2) found in the conditioned media of established CHO cultures, cells were grown in a chemically defined, low protein, serum-free media (PROCHO4-CDM, Cambrex). In the process of adapting the cells to this media, the cells adapted from adherent to suspension growth.

Cells were grown in F-12 Ham's+10% FBS to near confluency in T-185 flasks, trypsinized and suspended in PROCHO4-CDM media. 107 cells were added to 50 mL of PROCHO4-CDM and incubated in T-185 flasks. After 4-5 passages, approximately 90% of the cells were no longer adherent and grew as a mixture of single cell and aggregated cell clumps. For conditioned media collections, typically 60 mL of fresh PROCHO4-CDM media was incubated with 7-8 ml, of a high cell density culture for 5-6 days. Cells were removed from the media by centrifugation and the media was subsequently clarified using a 0.2 micron. filter. The media was quantitated for yield of G-CSF-NNT155 (NNT155 disclosed as SEQ ID NO: 2) by Western blot (typically 100-200 μg/L) and stored until needed.

2.C. Expression of G-CSF-NNT Constructs in PROCHO4-CDM

Figure 8:
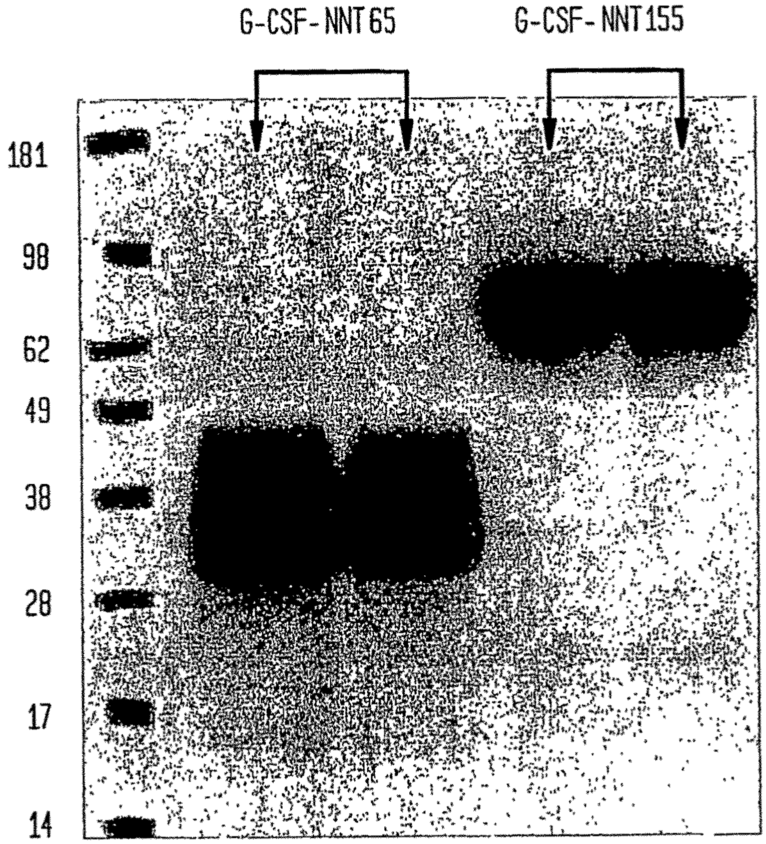
FIG. 8 is a Western blot of the G-CSF-NNT155 (NNT155 disclosed as SEQ ID NO: 2) and G-CSF-NNT65 (NNT65 disclosed as SEQ ID NO: 1) constructs (in duplicate) that were expressed in CHOK1 cells grow in PROCHO4-CDM media.

Samples were conditioned media from the foregoing bulk CHO cell lines grown for 6 days in PROCHO4-CDM. Western blots were probed using polyclonal antibody against G-CSF. As shown in FIG. 8, the size of both constructs were the same as was seen in Ham's media (as described above) and there was no degradation observed in the G-CSF-NNT155 (NNT155 disclosed as SEQ ID NO: 2) cell lines.

2.D. Optimization of Expression

Various chemical and nutrient additives as well as various environmental parameters were tested in an attempt to determine growth conditions necessary to maximize expression of the desired product. The following approaches resulted in an increase in protein accumulation.

Chemical Additives

Although it was known that not all chemical additives result in an increase in protein production, published literature indicated that the addition of adenosine or AMP to 2.5 mM leads to cell cycle arrest; effectively prolonging cell culture viability with a concomitant increase in protein accumulation. The effect of AMP was tested on CHO-mediated production of G-CSF-NNT155 (NNT155 disclosed as SEQ ID NO: 2) production in ProCHO4 chemically defined medium (CDM). AMP was added at a final concentration of 1 mM in ProCHO4 CDM. No decrease in cell viability compared to control was observed. The addition of AMP resulted in a slight increase in protein production, Environmental Parameters Temperature Changes Reduced incubation temperatures for CHO cultures can lead to markedly enhanced levels of protein production. As was found with other protein production enhancement methods, the observed effect is due to enhanced protein production during cell cycle arrest. The effect of reducing the incubation temperature of the recombinant CHO line from 37° C. to 28° C. was examined. Although cultures maintained at 28° C. remained viable considerably longer than those at 37° C., the lower temperature did not result in higher recombinant protein production.

Adaptation to Suspension Culture

The bulk CHO population was converted to spinner flask culture conditions. Adaptation to suspension culture was mediated by growth in ProCHO4 CDM. Following adaptation, cells were expanded in T-flasks and seeded into spinner flasks containing ProCHO5 CDM at various densities. A marked increase in protein production was observed. during adaptation to suspension culture in ProCHO5 CDM, regardless of Whether the cells were grown in static or spinner cultures.

Use of Different Cell Lines as Hosts

One approach to optimization of expression may be to use a new cell line for host cells. Accordingly, a new shipment of CHO-K1 from ATCC was obtained. The new population was propagated and banked at an early passage for future use. This defined culture was used to generate stable clonal cell lines expressing the recombinant protein of interest. Briefly, CHO-K1 cells were electroporated with the vector of interest and selected for stable expression of hygromycin. 92 colonies were isolated and evaluated for expression of the recombinant protein of interest. Many of these colonies exhibited expression levels that were markedly higher than that of the original transfected population, described above.

Results

A very slight enhancement of expression was observed when cultures were treated with 1 mM AMP. Reduced culture temperatures increased the longevity of the cultures, but there was no enhancement of protein expression. Adaptation to suspension culture conditions in ProCHO5 CDM dramatically enhanced expression of the recombinant protein. Also, isolated clones from an ATCC-defined CHO-K1 cell line expressed the desired protein at significantly higher levels than the originally isolated population.

Example 3

Pharmacokinetic Evaluation of G-CSF-NNT155 Conjugate (NNT155 Disclosed as SEQ ID NO: 2)

The pharmacokinetic parameters of the G-CSF-NNT155 protein conjugate (NNT155 disclosed as SEQ ID NO: 2) was evaluated. Three other compounds were included as positive controls. The controls were NEULASTA (PEG-G-CSF), NEUPOGEN (rh-G-CSF) and G-CSF compounds. The compounds were tested by single intravenous (i.v.) administration to mice and blood was collected up to 72 hours post-dosing. The plasma was analyzed by the ELISA method.

3.A. Analytical Method

The assay employed the quantitative sandwich enzyme immunoassay technique. A monoclonal antibody specific for G-CSF had been pre-coated onto a microplate. Standards and samples were pipetted into the wells. Any G-CSF present was bound by the immobilized antibody. After washing away any unbound substances, an enzyme-linked polyclonal antibody specific for G-CSF was added to the wells. Following a wash to remove any unbound antibody-enzyme reagent, a substrate solution was added to the wells and color developed in proportion to the amount of G-CSF bound in the initial step. The color development was stopped and the intensity of the color was measured.

Reagents

The following reagents and material were used:

G-CSF Microplate: 96 well polystyrene microplate (12 strips of 8 wells) coated with a murine monoclonal antibody against G-CSF.

G-CSF conjugate: 21 mL of polyclonal antibody against G-CSF conjugated to horseradish peroxidase, with preservative.

G-CSF standard: 2 vials (25 ng/mL) of recombinant human G-CSF in a buffered protein base with preservative, lyophilized.

Assay Diluent RD1A: 11 mL of a buffered protein base with preservative.

Calibrator Diluent RD5: 21 mL of a buffered protein base with preservative. For cell culture supernate samples.

Calibrator Diluent RD6A: 21 mL of animal serum with preservative. For serum/plasma samples.

Wash Buffer Concentrate: 21 mL of a 25-fold concentrated solution of buffered surfactant with preservative.

Color Reagent A: 12.5 mL of stabilized hydrogen peroxide,

Color Reagent B: 12.5 mL of stabilized chromogen (tetramethylbenzidine).

Stop Solution: 6 mL of 2N sulfuric acid.

Plate Covers: 4 adhesive strips.

Reagent Preparation 20 mL of Wash Buffer Concentrate was diluted into deionized or distilled water to prepare 500 mL of Wash Buffer. The G-CSF Standard was reconstituted with 1 mL deionized or distilled water. This reconstitution produced a stock solution of 25000 pg/mL. The G-CSF standard was allowed to sit for a minimum of 15 minutes with gentle agitation prior to making dilutions. Nine hundred (900) μL of Calibrator Diluent RD6A was pipetted into a 2500 pg/mL tube. 600 μL of the same diluent was pipetted into the remaining 4 tubes. The stock solution was used to produce a dilution series: 25000 pg/mL (1:10)→2500 pg/mL and 25000 pg/mL (1:3)→833.3 pg/mL (1:3)→277.8 pg/mL (1:3)→92.6 pg/mL (1:3)→30.9 pg/mL. Each tube was mixed thoroughly before the next transfer. The 2500 pg/mL standard served as the high standard. The Calibrator Diluent RD6A served as the zero standard (0 pg/mL). The standard curve was performed with 6 point: 2500-833.3-277.8-92.6-30.9-0 pg/mL, double well for each point. For the substrate solution, Color Reagent A and B was mixed together in equal volumes within 15 minutes of use. The reagents were protected from light.

Assay Procedure

All reagents and samples were brought to room temperature before use. All reagents and working standards were prepared. One hundred (100) μL of Assay Diluent RD1A were added to each well, 100 μL of standard and an appropriate volume of sample were also added to each well. The wells were covered with an adhesive strip and incubated. for 2 h at room temperature. Each well was aspirated and washed with 400 μL of wash buffer, which was repeated twice for a total of three washes. After the last wash, any remaining wash buffer was removed by aspirating or decanting. The plate was inverted and blotted against clean paper towels. 200 μL of G-CSF conjugate was added to each well. The wells were covered with a new adhesive strip. The wells were incubated for 2 h at room temperature. The aspiration/wash described above was repeated. Two hundred (200) μL of Substrate Solution was added to each well. The wells were incubated for 20 min. at room temperature. The wells were protected from fight. Then, 50 μL of stop solution were added to each well. Finally, the optical density of each well within 30 min, was determined using a microplate reader (VersaMax-Molecular Device) set to 450 nm with correction to 570 nm (OD 450 nm-OD 570 nm).

Pharmacokinetic Analysis

A non-compartmental pharmacokinetic analysis (WIN-NonLin software version 4.1) was applied. The following main parameters were observed or calculated for each G-CSF construct: $t_f$, last time at which each compound concentration was measurable; $\lambda_z$, apparent terminal rate constant associated to the apparent terminal phase, estimated by linear regression analysis of the logarithm of the plasma concentrations versus time in the mono-exponential terminal part of the curve; $t_{1/2,z}$, apparent terminal half-life, calculated according to the following equation: $t_{1/2,z}=\ln(2)/\lambda_z$; AUC, area under the plasma concentration-time curve from time zero to infinity; AUC/D, area under the plasma concentration-time curve per unit of dose; MRT, mean residence time calculated as the ratio between the area under the first moment curve, AUMC, and AUC; CL, systemic clearance, calculated as CL=D/AUC; and $V_{ss}$, steady state volume of distribution, calculated as $V_{ss}$=CL*MRT, Results As shown in Table 9, pharmacokinetic studies in mice showed that G-CSF-NNT155 (NNT155 disclosed as SEQ ID NO: 2) possessed a longer half-life (6.2 h) than either the G-CSF Control (1.53 h), NEUPOGEN compound (1.13 h) or the NEULASTA compound (3.04 h). G-CSF-NNT155's (NNT155 disclosed as SEQ ID NO: 2) longer half-life corresponded to a more sustained duration of effect compared to all three controls. A corresponding substantial decrease of systemic clearance was Observed for G-CSF-NNT155 (NNT155 disclosed as SEQ ID NO: 2), accounting for the 9.5 mL/h/kg systemic clearance. Other conjugates containing amino acid extensions disclosed herein exhibited a decreased half-life relative to control.

Example 4

Bioavailability and Efficacy of G-CSF-NNT155 Conjugate (NNT155 Disclosed as SEQ ID NO: 2)

Neutropenia, a low absolute count of neutrophils, is a serious condition that can impede the fight against infections. To stimulate a peripheral increase in neutrophil counts, granulocyte colony stimulating factor (G-CSF) may be used as a therapy for neutropenia or in combination with other stimulating factors in collection of cells for transplant. The bioavailability of partially purified G-CSF-NNT155 (NNT155 disclosed as SEQ ID NO: 2), PEG-G-CSF (NEULASTA) and rh-G-CSF (NEUPOGEN) was determined and compared via i.v. (intravenous) and s.c. (subcutaneous) administration. The NEUPOGEN compound is a recombinant methionyl human G-CSF. The NEULASTA, compound is a covalent conjugate of recombinant methionyl human G-CSF and monomethoxypolyethylene glycol. As described above, G-CSF-NNT155 (NNT155 disclosed as SEQ ID NO: 2) is an amino acid lengthened and/or glycosylated form of G-CSF.

4.A. Testing for Bioavailability Through ELISA

To evaluate the bioavailability of G-CSF-NNT155 (NNT155 disclosed as SEQ ID NO: 2), an ELISA analysis was performed on plasma samples obtained from mice that were given doses of G-CSF-NNT155 (NNT155 disclosed as SEQ ID NO: 2), PEG-G-CSF and rh-G-CSF through i.v. and s.c. administration.

Test and control articles were as follows: partially purified G-CSF-NNT155 (NNT155 disclosed as SEQ ID NO: 2), PEG-G-CSF (NEULASTA), rh-G-CSF (NEUPOGEN) and the vehicle control (150 mM NaCl+20 mM NaOAc+0.004% Tween-20); each manufactured in a manner that was acceptable for use in animals via the designated routes of administration, i.v. and s.c.

Mice were given doses of G-CSF-NNT155 (NNT155 disclosed as SEQ ID NO: 2), PEG-G-CSF, rh-G-CSF (each in the amount of 125 μg/kg) and a vehicle control through i.v and s.c. administration. Mouse plasma samples were isolated. If required, the mouse plasma samples were diluted.

Then, the mouse samples were analyzed with G-CSF ELISA. The main purpose of analyzing the plasma samples via ELISA was for qualitative purposes only, and not for quantitative purposes (i.e., not to obtain extremely precise blood plasma level concentrations). The G-CSF ELISA results either provided a qualitative affirmation that the test article was present in the plasma or a qualitative repudiation that the test article was not in the plasma. The plasma samples were analyzed in triplicate, using two dilutions.

The results were that intravenously administered G-CSF-NNT155 (NNT155 disclosed as SEQ ID NO: 2) could be detected out to 72 hours, whereas PEG-G-CSF could only be detected out to 24 hours. In addition, both subcutaneously administered G-CSF-NNT155 (NNT155 disclosed as SEQ ID NO: 2) and PEG-G-CSF could be detected out to 72 hours. Subcutaneously administered rh-G-CSF could be detected at the 15-minute and 2-hour sampling time points.

4.B. A Single Dose Comparison of G-CSF-NNT155 (NNT155 Disclosed as SEQ ID NO: 2) and PEG-G-CSF on the Hematopoietic Effects in Mice In another evaluation of the bioavailability and efficacy of G-CSF-NNT155 (NNT155 disclosed as SEQ ID NO: 2), hematology analysis involving white blood cell and neutrophil count measurements was performed on plasma samples obtained from mice that were given doses of G-CSF-NNT155 (NNT155 disclosed as SEQ ID NO: 2), PEG-G-CSF and rh-G-CSF through i.v. and s.c. administration.

Test and control articles were the same as for the above G-CSF ELISA evaluation. The procedures for obtaining plasma samples were also the same as for the G-CSF ELISA evaluation. Hematology analysis results were as follows.

The white blood cell count mean data. for the vehicle control ranged from $0.76 \times 10^3$/μL to $4.35 \times 10^3$/μL and $1.27 \times 10^3$/μL to $4.25 \times 10^3$/μL for the i.v. and s.c. administration, respectively. The mean absolute neutrophil count data for the vehicle control ranged from $0.11 \times 10^3$/μL to $0.55 \times 10^3$/μL and $0.29 \times 10^3$/μL to $0.35 \times 10^3$/μL for i.v. and s.c. administration, respectively.

The mean white blood cell count for G-CSF-NNT155 (NNT155 disclosed as SEQ ID NO: 2) increased from $1.44 \times 10^3$/μL, 15 minutes post-dose to $11.45 \times 10^3$/μL, 72 hours post i.v. administration. The mean white blood cell count for G-CSF-NNT155 (NNT155 disclosed as SEQ ID NO: 2) increased from $3.15 \times 10^3$/μL, 15 minutes post-dose to $11.45 \times 10^3$/μL, 72 hours post s.c. administration. Similarly, mean absolute neutrophil count data for G-CSF-NNT155 (NNT155 disclosed as SEQ ID NO: 2) increased from $0.04 \times 10^3$/μL, 15 minutes post-dose to $4.24 \times 10^3$/μL, 72 hours post i.v. administration. The mean absolute neutrophil count for G-CSF-NNT155 (NNT155 disclosed as SEQ ID NO: 2) increased from $0.25 \times 10^3$/μL, at 15 minutes post-dose to $2.04 \times 10^3$/μL, at 72 hours post administration and decreasing to $0.14 \times 10^3$/μL for the s.c. route of administration at 120 hours post administration.

The mean white blood cell count for PEG-G-CSF (NEULASTA) increased from $1.36 \times 10^3$/μL, at 15 minutes post-dose to $6.03 \times 10^3$/μL, at 24 hours post administration, and then decreased to $3.01 \times 10^3$/μL, at 72 hour post i.v. administration. The mean white blood cell count for PEG-G-CSF (NEULASTA) increased from $1.47 \times 10^3$/μL, at 15 minutes post-dose to $4.58 \times 10^3$/μL, at 24 hours post administration, and then decreased to $2.47 \times 10^3$/μL, at 120 hours post s.c. administration. The mean absolute neutrophil count for PEG-G-CSF (NEULASTA) increased from $0.05 \times 10^3$/μL, at 15 minutes post-dose to $1.83 \times 10^3$/μL, at 24 hours post administration, and then decreased to $0.20 \times 10^3$/μL, at 72 hours post i.v. administration. The mean absolute neutrophil count for PEG-G-CSF (NEULASTA) increased from $0.18 \times 10^3$/μL, at 15 minutes post-dose to $1.04 \times 10^3$/μL, at 24 hours post administration and then decreased to $0.22 \times 10^3$/μL, 120 hours post s.c. administration.

The mean white blood cell count for rh-G-CSF (NEUPOGEN) decreased from $1.30 \times 10^3$/μL, at 15 minutes post-dose to $1.19 \times 10^3$/μL at 2 hours post s.c. administration. The mean absolute neutrophil count for rh-G-CSF (NEUPOGEN) increased from $0.11 \times 10^3$/μL, at 15 minutes post-dose to $0.49 \times 10^3$/μL at 2 hours post s.c. route of administration.

The result showed that intravenous administration of G-CSF-NNT155 (disclosed as SEQ ID NO: 2) demonstrated a substantial increase in white blood cell counts, through 72 hours post-dose, which correlated directly to an increase in absolute neutrophil counts. This mean increase exceeded the white blood cell count of the vehicle control by approximately 260%. Similarly, a mean increase in the white blood cell count for the s.c. administration of G-CSF-NNT1.55 (NNT155 disclosed as SEQ ID NO: 2) exceeded that of both the vehicle control and PEG-G-CSF by approximately 295%, 72 hours post-dose. However, both the mean white blood cell count and the mean absolute neutrophil count returned to that of both the vehicle control and PEG-G-CSF at 120 hours post-dose.

In some embodiments, the peptide contains the sequence NNT, NNNNT (SEQ ID NO: 182) or NNNNNT (SEQ ID NO: 183), and n is an integer of about 150 to about 160. In some of these embodiments, the biologically active protein is G-CSF.

All publications cited in the specification are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

TABLE 1

| Peptide Motifs having N(Asn) as the Major Constituent (SEQ ID NOS: 184-904, respectively, in order of appearance) |
|---|
| NNT, TNN, NTN, NNNT, TNNN, NTNN, NNTN, NNNNT, TNNNN, NTNNN, |
| NNTNN, NNNTN, NNNTT, TTNNN, TNTNN, TNNTN, TNNNT, NTTNN, |
| NTNTN, NTNNT, NNTTN, NNTNT, NNNNNT, TNNNNN, NTNNNN, NNTNNN, |
| NNNTNN, NNNNTN, NNNNTT, TTNNNN, TNTNNN, TNNTNN, TNNNTN, |
| TNNNNT, NTTNNN, NTNTNN, NTNNTN, NTNNNT, NNTTNN, NNTNTN, |
| NNTNNT, NNNTTN, NNNTNT, NNNNTTT, TTTNNNN, TNTTNNN, TNTNTNN, |
| TNTNNTN, TNTNNNT, TNNTTNN, TNNTNTN, TNNTNNT, TNNNTNT, |
| TNNNTTN, TNNNNTT, TTNTNNN, TTNNTNN, TTNNNTN, TTNNNNT, |
| NTTTNNN, NTTNTNN, NTTNNTN, NTTNNNT, NTNTTNN, NTNNTTN, |
| NTNNNTT, NTNTNTN, NTNTNNT, NTNNTNT, NNTTTNN, NNTTNTN, |
| NNTTNNT, NNTNTTN, NNTNTNT, NNTNNTT, NNNTTTN, NNNTTNT, |
| NNNTNTT, NNNNNTT, TTNNNNN, TNTNNNN, TNNTNNN, TNNNTNN, |
| TNNNNTN, TNNNNNT, NTTNNNN, NTNTNNN, NTNNTNN, NTNNNTN, |
| NTNNNNT, NNTTNNN, NNTNTNN, NNTNNTN, NNTNNNT, NNNTTNN, |
| NNNTNTN, NNNTNNT, NNNNTTN, NNNNTNT NNNNNNT, TNNNNNN, |
| NTNNNNN, NNTNNNN, NNNTNNN, NNNNTNN, NNNNNTN, NNA, ANN, |
| NAN, NNNA, ANNN, NANN, NNAN, NNNNA, ANNNN, NANNN, NNANN, |
| NNNAN, NNNAA, AANNN, ANANN, ANNAN, ANNNA, NAANN, NANAN, |
| NANNA, NNAAN, NNANA, NNNNNA, ANNNNN, NANNNN, NNANNN, |
| NNNANN, NNNNAN, NNNNAA, AANNNN, ANANNN, ANNANN, ANNNAN, |
| ANNNNA, NAANNN, NANANN, NANNAN, NANNNA, NNAANN, NNANAN, |
| NNANNA, NNNAAN, NNNANA, NNNNAAA, AAANNNN, ANAANNN, |
| ANANANN, ANANNAN, ANANNNA, ANNAANN, ANNANAN, ANNANNA, |
| ANNNANA, ANNNAAN, ANNNNAA, AANANNN, AANNANN, AANNNAN, |
| AANNNNA, NAAANNN, NAANANN, NAANNAN, NAANNNA, NANAANN, |
| NANNAAN, NANNNAA, NANANAN, NANANNA, NANNANA, NNAAANN, |
| NNAANAN, NNAANNA, NNANAAN, NNANANA, NNANNAA, NNNAAAN, |
| NNNAANA, NNNANAA, NNNNNAA, AANNNNN, ANANNNN, ANNANNN, |
| ANNNANN, ANNNNAN, ANNNNNA, NAANNNN, NANANNN, NANNANN, |
| NANNNAN, NANNNNA, NNAANNN, NNANANN, NNANNAN, NNANNNA, |
| NNNAANN, NNNANAN, NNNANNA, NNNNAAN, NNNNANA NNNNNNA, |
| ANNNNNN, NANNNNN, NNANNNN, NNNANNN, NNNNANN, NNNNNAN, |
| NNS, SNN, NSN, NNNS, SNNN, NSNN, NNSN, NNNNS, SNNNN, NSNNN, |
| NNSNN, NNNSN, NNNSS, SSNNN, SNSNN, SNNSN, SNNNS, NSSNN, NSNSN, |
| NSNNS, NNSSN, NNSNS, NNNNNS, SNNNNN, NSNNNN, NNSNNN, NNNSNN, |

TABLE 1-continued

| Peptide Motifs having N(Asn) as the Major Constituent (SEQ ID NOS: 184-904, respectively, in order of appearance) |
|---|
| NNNNSN, NNNNSS, SSNNNN, SNSNNN, SNNSNN, SNNNSN, SNNNNS, |
| NSSNNN, NSNSNN, NSNNSN, NSNNNS, NNSSNN, NNSNSN, NNSNNS, |
| NNNSSN, NNNSNS, NNNNSSS, SSSNNNN, SNSSNNN, SNSNSNN, SNSNNSN, |
| SNSNNNS, SNNSSNN, SNNSNSN, SNNSNNS, SNNNSNS, SNNNSSN, |
| SNNNNSS, SSNSNNN, SSNNSNN, SSNNNSN, SSNNNNS, NSSSNNN, |
| NSSNSNN, NSSNNSN, NSSNNNS, NSNSSNN, NSNNSSN, NSNNNSS, |
| NSNSNSN, NSNSNNS, NSNNSNS, NNSSSNN, NNSSNSN, NNSSNNS, |
| NNSNSSN, NNSNSNS, NNSNNSS, NNNSSSN, NNNSSNS, NNNSNSS, |
| NNNNNSS, SSNNNNN, SNSNNNN, SNNSNNN, SNNNSNN, SNNNNSN, |
| SNNNNNS, NSSNNNN, NSNSNNN, NSNNSNN, NSNNNSN, NSNNNNS, |
| NNSSNNN, NNSNSNN, NNSNNSN, NNSNNNS, NNNSSNN, NNNSNSN, |
| NNNSNNS, NNNNSSN, NNNNSNS NNNNNNS, SNNNNNN, NSNNNNN, |
| NNSNNNN, NNNSNNN, NNNNSNN, NNNNNSN, NNQ, QNN, NQN, NNNQ, |
| QNNN, NQNN, NNQN, NNNNQ, QNNNN, NQNNN, NNQNN, NNNQN, NNNQQ, |
| QQNNN, QNQNN, QNNQN, QNNNQ, NQQNN, NQNQN, NQNNQ, NNQQN, |
| NNQNQ, NNNNNQ, QNNNNN, NQNNNN, NNQNNN, NNNQNN, NNNNQN, |
| NNNNQQ, QQNNNN, QNQNNN, QNNQNN, QNNNQN, QNNNNQ, NQQNNN, |
| NQNQNN, NQNNQN, NQNNNQ, NNQQNN, NNQNQN, NNQNNQ, NNNQQN, |
| NNNQNQ, NNNNQQQ, QQQNNNN, QNQQNNN, QNQNQNN, QNQNNQN, |
| QNQNNNQ, QNNQQNN, QNNQNQN, QNNQNNQ, QNNNQNQ, QNNNQQN, |
| QNNNNQQ, QQNQNNN, QQNNQNN, QQNNNQN, QQNNNNQ, NQQQNNN, |
| NQQNQNN, NQQNNQN, NQQNNNQ, NQNQQNN, NQNNQQN, NQNNNQQ, |
| NQNQNQN, NQNQNNQ, NQNNQNQ, NNQQQNN, NNQQNQN, NNQQNNQ, |
| NNQNQQN, NNQNQNQ, NNQNNQQ, NNNQQQN, NNNQQNQ, NNNQNQQ, |
| NNNNNQQ, QQNNNNN, QNQNNNN, QNNQNNN, QNNNQNN, QNNNNQN, |
| QNNNNNQ, NQQNNNN, NQNQNNN, NQNNQNN, NQNNNQN, NQNNNNQ, |
| NNQQNNN, NNQNQNN, NNQNNQN, NNQNNNQ, NNNQQNN, NNNQNQN, |
| NNNQNNQ, NNNNQQN, NNNNQNQ NNNNNNQ, QNNNNNN, NQNNNNN, |
| NNQNNNN, NNNQNNN, NNNNQNN, NNNNNQN, NNE, ENN, NEN, NNNE, |
| ENNN, NENN, NNEN, NNNNE, ENNNN, NENNN, NNENN, NNNEN, NNNEE, |
| EENNN, ENENN, ENNEN, ENNNE, NEENN, NENEN, NENNE, NNEEN, |
| NNENE, NNNNNE, ENNNNN, NENNNN, NNENNN, NNNENN, NNNNEN, |
| NNNNEE, EENNNN, ENENNN, ENNENN, ENNNEN, ENNNNE, NEENNN, |
| NENENN, NENNEN, NENNNE, NNEENN, NNENEN, NNENNE, NNNEEN, |
| NNNENE, NNNNEEE, EEENNNN, ENEENNN, ENENENN, ENENNEN, |
| ENENNNE, ENNEENN, ENNENEN, ENNENNE, ENNNENE, ENNNEEN, |
| ENNNNEE, EENENNN, EENNENN, EENNNEN, EENNNNE, NEEENNN, |
| NEENENN, NEENNEN, NEENNNE, NENEENN, NENNEEN, NENNNEE, |
| NENENEN, NENENNE, NENNENE, NNEEENN, NNEENEN, NNEENNE, |

TABLE 1-continued

| Peptide Motifs having N(Asn) as the Major Constituent (SEQ ID NOS: 184-904, respectively, in order of appearance) |
|---|
| NNENEEN, NNENENE, NNENNEE, NNNEEEN, NNNEENE, NNNENEE, NNNNNEE, EENNNNN, ENENNNN, ENNENNN, ENNNENN, ENNNNEN, ENNNNNE, NEENNNN, NENENNN, NENNENN, NENNNEN, NENNNNE, NNEENNN, NNENENN, NNENNEN, NNENNNE, NNNEENN, NNNENEN, NNNENNE, NNNNEEN, NNNNENE NNNNNNE, ENNNNNN, NENNNNN, NNENNNN, NNNENNN, NNNNENN, NNNNNEN, NNH, HNN, NHN, NNNH, HNNN, NHNN, NNHN, NNNNH, HNNNN, NHNNN, NNHNN, NNNHN, NNNHH, HHNNN, HNHNN, HNNHN, HNNNH, NHHNN, NHNHN, NHNNH, NNHHN, NNHNH, NNNNNH, HNNNNN, NHNNNN, NNHNNN, NNNHNN, NNNNHN, NNNNHH, HHNNNN, HNHNNN, HNNHNN, HNNNHN, HNNNNH, NHHNNN, NHNHNN, NHNNHN, NHNNNH, NNHHNN, NNHNHN, NNHNNH, NNNHHN, NNNHNH, NNNNHHH, HHHNNNN, HNHHNNN, HNHNHNN, HNHNNHN, HNHNNNH, HNNHHNN, HNNHNHN, HNNHNNH, HNNNHNH, HNNNHHN, HNNNNHH, HHNHNNN, HHNNHNN, HHNNNHN, HHNNNNH, NHHHNNN, NHHNHNN, NHHNNHN, NHHNNNH, NHNHHNN, NHNNHHN, NHNNNHH, NHNHNHN, NHNHNNH, NHNNHNH, NNHHHNN, NNHHNHN, NNHHNNH, NNHNHHN, NNHNHNH, NNHNNHH, NNNHHHN, NNNHHNH, NNNHNHH, NNNNNHH, HHNNNNN, HNHNNNN, HNNHNNN, HNNNHNN, HNNNNHN, HNNNNNH, NHHNNNN, NHNHNNN, NHNNHNN, NHNNNHN, NHNNNNH, NNHHNNN, NNHNHNN, NNHNNHN, NNHNNNH, NNNHHNN, NNNHNHN, NNNHNNH, NNNNHHN, NNNNHNH NNNNNNH, HNNNNNN, NHNNNNN, NNHNNNN, NNNHNNN, NNNNHNN, NNNNNHN, NND, DNN, NDN, NNND, DNNN, NDNN, NNDN, NNNND, DNNNN, NDNNN, NNDNN, NNNDN, NNNDD, DDNNN, DNDNN, DNNDN, DNNND, NDDNN, NDNDN, NDNND, NNDDN, NNDND, NNNNND, DNNNNN, NDNNNN, NNDNNN, NNNDNN, NNNNDN, NNNNDD, DDNNNN, DNDNNN, DNNDNN, DNNNDN, DNNNND, NDDNNN, NDNDNN, NDNNDN, NDNNND, NNDDNN, NNDNDN, NNDNND, NNNDDN, NNNDND, NNNNDDD, DDDNNNN, DNDDNNN, DNDNDNN, DNDNNDN, DNDNNND, DNNDDNN, DNNDNDN, DNNDNND, DNNNDND, DNNNDDN, DNNNNDD, DDNDNNN, DDNNDNN, DDNNNDN, DDNNNND, NDDDNNN, NDDNDNN, NDDNNDN, NDDNNND, NDNDDNN, NDNNDDN, NDNNNDD, NDNDNDN, NDNDNND, NDNNDND, NNDDDNN, NNDDNDN, NNDDNND, NNDNDDN, NNDNDND, NNDNNDD, NNNDDDN, NNNDDND, NNNDNDD, NNNNNDD, DDNNNNN, DNDNNNN, DNNDNNN, DNNNDNN, DNNNNDN, DNNNNND, NDDNNNN, NDNDNNN, NDNNDNN, NDNNNDN, NDNNNND, NNDDNNN, NNDNDNN, NNDNNDN, NNDNNND, NNNDDNN, NNNDNDN, NNNDNND, NNNNDDN, NNNNDND NNNNNND, DNNNNNN, NDNNNNN, NNDNNNN, NNNDNNN, NNNNDNN, and NNNNNDN. |

TABLE 2

| Peptide Motifs having G (Gly) as the Major Constituent (SEQ ID NOS: 905-1728, respectively, in order of appearance) |
|---|
| GGT, TGG, GTG, GGGT, TGGG, GTGG, GGTG, GGGGT, TGGGG, GTGGG, GGTGG, GGGTG, GGGTT, TTGGG, TGTGG, TGGTG, TGGGT, GTTGG, GTGTG, GTGGT, GGTTG, GGTGT, GGGGGT, TGGGGG, GTGGGG, GGTGGG, GGGTGG, GGGGTG, GGGGTT, TTGGGG, TGTGGG, TGGTGG, TGGGTG, TGGGGT, GTTGGG, GTGTGG, GTGGTG, GTGGGT, GGTTGG, GGTGTG, GGTGGT, GGGTTG, GGGTGT, GGGGTTT, TTTGGGG, TGTTGGG, TGTGTGG, TGTGGTG, TGTGGGT, TGGTTGG, TGGTGTG, TGGTGGT, TGGGTGT, TGGGTTG, TGGGGTT, TTGTGGG, TTGGTGG, TTGGGTG, TTGGGGT, GTTTGGG, GTTGTGG, GTTGGTG, GTTGGGT, GTGTTGG, GTGGTTG, GTGGGTT, GTGTGTG, GTGTGGT, GTGGTGT, GGTTTGG, GGTTGTG, GGTTGGT, GGTGTTG, GGTGTGT, GGTGGTT, GGGTTTG, GGGTTGT, GGGTGTT, GGGGGTT, TTGGGGG, TGTGGGG, TGGTGGG, TGGGTGG, TGGGGTG, TGGGGGT, GTTGGGG, GTGTGGG, GTGGTGG, GTGGGTG, GTGGGGT, GGTTGGG, GGTGTGG, GGTGGTG, GGTGGGT, GGGTTGG, GGGTGTG, GGGTGGT, GGGGTTG, GGGGTGT GGGGGGT, TGGGGGG, GTGGGGG, GGTGGGG, GGGTGGG, GGGGTGG, GGGGGTG, GGA, AGG, GAG, GGGA, AGGG, GAGG, GGAG, GGGGA, AGGGG, GAGGG, GGAGG, GGGAG, GGGAA, AAGGG, AGAGG, AGGAG, AGGGA, GAAGG, GAGAG, GAGGA, GGAAG, GGAGA, GGGGGA, AGGGGG, GAGGGG, GGAGGG, GGGAGG, GGGGAG, GGGGAA, AAGGGG, AGAGGG, AGGAGG, AGGGAG, AGGGGA, GAAGGG, GAGAGG, GAGGAG, GAGGGA, GGAAGG, GGAGAG, GGAGGA, GGGAAG, GGGAGA, GGGGAAA, AAAGGGG, AGAAGGG, AGAGAGG, AGAGGAG, AGAGGGA, AGGAAGG, AGGAGAG, AGGAGGA, AGGGAGA, AGGGAAG, AGGGGAA, AAGAGGG, AAGGAGG, AAGGGAG, AAGGGGA, GAAAGGG, GAAGAGG, GAAGGAG, GAAGGGA, GAGAAGG, GAGGAAG, GAGGGAA, GAGAGAG, GAGAGGA, GAGGAGA, GGAAAGG, GGAAGAG, GGAAGGA, GGAGAAG, GGAGAGA, GGAGGAA, GGGAAAG, GGGAAGA, GGGAGAA, GGGGGAA, AAGGGGG, AGAGGGG, AGGAGGG, AGGGAGG, AGGGGAG, AGGGGGA, GAAGGGG, GAGAGGG, GAGGAGG, GAGGGAG, GAGGGGA, GGAAGGG, GGAGAGG, GGAGGAG, GGAGGGA, GGGAAGG, GGGAGAG, GGGAGGA, GGGGAAG, GGGGAGA GGGGGGA, AGGGGGG, GAGGGGG, GGAGGGG, GGGAGGG, GGGGAGG, GGGGGAG, GGS, SGG, GSG, GGGS, SGGG, GSGG, GGSG, GGGGS, SGGGG, GSGGG, GGSGG, GGGSG, GGGSS, SSGGG, SGSGG, SGGSG, SGGGS, GSSGG, GSGSG, GSGGS, GGSSG, GGSGS, GGGGGS, SGGGGG, GSGGGG, GGSGGG, GGGSGG, GGGGSG, GGGGSS, SSGGGG, SGSGGG, SGGSGG, SGGGSG, SGGGGS, GSSGGG, GSGSGG, GSGGSG, GSGGGS, GGSSGG, GGSGSG, GGSGGS, GGGSSG, GGGSGS, GGGGSSS, SSSGGGG, SGSSGGG, SGSGSGG, SGSGGSG, SGSGGGS, SGGSSGG, SGGSGSG, SGGSGGS, SGGGSGS, SGGGSSG, |

TABLE 2-continued

| Peptide Motifs having G (Gly) as the Major Constituent (SEQ ID NOS: 905-1728, respectively, in order of appearance) |
|---|
| SGGGGSS, SSGSGGG, SSGGSGG, SSGGGSG, SSGGGGS, GSSSGGG, GSSGSGG, GSSGGSG, GSSGGGS, GSGSSGG, GSGGSSG, GSGGGSS, GSGSGSG, GSGSGGS, GSGGSGS, GGSSSGG, GGSSGSG, GGSSGGS, GGSGSSG, GGSGSGS, GGSGGSS, GGGSSSG, GGGSSGS, GGGSGSS, GGGGGSS, SSGGGGG, SGSGGGG, SGGSGGG, SGGGSGG, SGGGGSG, SGGGGGS, GSSGGGG, GSGSGGG, GSGGSGG, GSGGGSG, GSGGGGS, GGSSGGG, GGSGSGG, GGSGGSG, GGSGGGS, GGGSSGG, GGGSGSG, GGGSGGS, GGGGSSG, GGGGSGS, GGGGGGS, SGGGGGG, GSGGGGG, GGSGGGG, GGGSGGG, GGGGSGG, GGGGGSG, GGQ, QGG, GQG, GGGQ, QGGG, GQGG, GGQG, GGGGQ, QGGGG, GQGGG, GGQGG, GGGQG, GGGQQ, QQGGG, QGQGG, QGGQG, QGGGQ, GQQGG, GQGQG, GQGGQ, GGQQG, GGQGQ, GGGGGQ, QGGGGG, GQGGGG, GGQGGG, GGGQGG, GGGGQG, GGGGQQ, QQGGGG, QGQGGG, QGGQGG, QGGGQG, QGGGGQ, GQQGGG, GQGQGG, GQGGQG, GQGGGQ, GGQQGG, GGQGQG, GGQGGQ, GGGQQG, GGGQGQ, GGGGQQQ, QQQGGGG, QGQQGGG, QGQGQGG, QGQGGQG, QGQGGGQ, QGGQQGG, QGGQGQG, QGGQGGQ, QGGGQGQ, QGGGQQG, QGGGGQQ, QQGQGGG, QQGGQGG, QQGGGQG, QQGGGGQ, GQQQGGG, GQQGQGG, GQQGGQG, GQQGGGQ, GQGQQGG, GQGGQQG, GQGGGQQ, GQGQGQG, GQGQGGQ, GQGGQGQ, GGQQQGG, GGQQGQG, GGQQGGQ, GGQGQQG, GGQGQGQ, GGQGGQQ, GGGQQQG, GGGQQGQ, GGGQGQQ, GGGGGQQ, QQGGGGG, QGQGGGG, QGGQGGG, QGGGQGG, QGGGGQG, QGGGGGQ, GQQGGGG, GQGQGGG, GQGGQGG, GQGGGQG, GQGGGGQ, GGQQGGG, GGQGQGG, GGQGGQG, GGQGGGQ, GGGQQGG, GGGQGQG, GGGQGGQ, GGGGQQG, GGGGQGQ GGGGGGQ, QGGGGGG, GQGGGGG, GGQGGGG, GGGQGGG, GGGGQGG, GGGGGQG, GGE, EGG, GEG, GGGE, EGGG, GEGG, GGEG, GGGGE, EGGGG, GEGGG, GGEGG, GGGEG, GGGEE, EEGGG, EGEGG, EGGEG, EGGGE, GEEGG, GEGEG, GEGGE, GGEEG, GGEGE, GGGGGE, EGGGGG, GEGGGG, GGEGGG, GGGEGG, GGGGEG, GGGGEE, EEGGGG, EGEGGG, EGGEGG, EGGGEG, EGGGGE, GEEGGG, GEGEGG, GEGGEG, GEGGGE, GGEEGG, GGEGEG, GGEGGE, GGGEEG, GGGEGE, GGGGEEE, EEEGGGG, EGEEGGG, EGEGEGG, EGEGGEG, EGEGGGE, EGGEEGG, EGGEGEG, EGGEGGE, EGGGEGE, EGGGEEG, EGGGGEE, EEGEGGG, EEGGEGG, EEGGGEG, EEGGGGE, GEEEGGG, GEEGEGG, GEEGGEG, GEEGGGE, GEGEEGG, GEGGEEG, GEGGGEE, GEGEGEG, GEGEGGE, GEGGEGE, GGEEEGG, GGEEGEG, GGEEGGE, GGEGEEG, GGEGEGE, GGEGGEE, GGGEEEG, GGGEEGE, GGGEGEE, GGGGGEE, EEGGGGG, EGEGGGG, EGGEGGG, EGGGEGG, EGGGGEG, EGGGGGE, GEEGGGG, GEGEGGG, GEGGEGG, GEGGGEG, GEGGGGE, |

TABLE 2-continued

| Peptide Motifs having G (Gly) as the Major Constituent (SEQ ID NOS: 905-1728, respectively, in order of appearance) |
|---|
| GGEEGGG, GGEGEGG, GGEGGEG, GGEGGGE, GGGEEGG, GGGEGEG, |
| GGGEGGE, GGGGEEG, GGGGEGE GGGGGGE, EGGGGGG, GEGGGGG, |
| GGEGGGG, GGGEGGG, GGGGEGG, GGGGGEG, GGH, HGG, GHG, GGGH, |
| HGGG, GHGG, GGHG, GGGGH, HGGGG, GHGGG, GGHGG, GGGHG, GGGHH, |
| HHGGG, HGHGG, HGGHG, HGGGH, GHHGG, GHGHG, GHGGH, GGHHG, |
| GGHGH, GGGGGH, HGGGGG, GHGGGG, GGHGGG, GGGHGG, GGGGHG, |
| GGGGHH, HHGGGG, HGHGGG, HGGHGG, HGGGHG, HGGGGH, GHHGGG, |
| GHGHGG, GHGGHG, GHGGGH, GGHHGG, GGHGHG, GGHGGH, GGGHHG, |
| GGGHGH, GGGGHHH, HHHGGGG, HGHHGGG, HGHGHGG, HGHGGHG, |
| HGHGGGH, HGGHHGG, HGGHGHG, HGGHGGH, HGGGHGH, HGGGHHG, |
| HGGGGHH, HHGHGGG, HHGGHGG, HHGGGHG, HHGGGGH, GHHHGGG, |
| GHHGHGG, GHHGGHG, GHHGGGH, GHGHHGG, GHGGHHG, GHGGGHH, |
| GHGHGHG, GHGHGGH, GHGGHGH, GGHHHGG, GGHHGHG, GGHHGGH, |
| GGHGHHG, GGHGHGH, GGHGGHH, GGGHHHG, GGGHHGH, GGGHGHH, |
| GGGGGHH, HHGGGGG, HGHGGGG, HGGHGGG, HGGGHGG, HGGGGHG, |
| HGGGGGH, GHHGGGG, GHGHGGG, GHGGHGG, GHGGGHG, GHGGGGH, |
| GGHHGGG, GGHGHGG, GGHGGHG, GGHGGGH, GGGHHGG, GGGHGHG, |
| GGGHGGH, GGGGHHG, GGGGHGH GGGGGGH, HGGGGGG, GHGGGGG, |
| GGHGGGG, GGGHGGG, GGGGHGG, GGGGGHG, GGN, NGG, GNG, GGGN, |
| NGGG, GNGG, GGNG, GGGGN, NGGGG, GNGGG, GGNGG, GGGNG, GGGNN, |
| NNGGG, NGNGG, NGGNG, NGGGN, GNNGG, GNGNG, GNGGN, GGNNG, |
| GGNGN, GGGGGN, NGGGGG, GNGGGG, GGNGGG, GGGNGG, GGGGNG, |
| GGGGNN, NNGGGG, NGNGGG, NGGNGG, NGGGNG, NGGGGN, GNNGGG, |
| GNGNGG, GNGGNG, GNGGGN, GGNNGG, GGNGNG, GGNGGN, GGGNNG, |
| GGGNGN, GGGGNNN, NNNGGGG, NGNNGGG, NGNGNGG, NGNGGNG, |
| NGNGGGN, NGGNNGG, NGGNGNG, NGGNGGN, NGGGNGN, NGGGNNG, |
| NGGGGNN, NNGNGGG, NNGGNGG, NNGGGNG, NNGGGGN, GNNNGGG, |
| GNNGNGG, GNNGGNG, GNNGGGN, GNGNNGG, GNGGNNG, GNGGGNN, |
| GNGNGNG, GNGNGGN, GNGGNGN, GGNNNGG, GGNNGNG, GGNNGGN, |
| GGNGNNG, GGNGNGN, GGNGGNN, GGGNNNG, GGGNNGN, GGGNGNN, |
| GGGGGNN, NNGGGGG, NGNGGGG, NGGNGGG, NGGGNGG, NGGGGNG, |
| NGGGGGN, GNNGGGG, GNGNGGG, GNGGNGG, GNGGGNG, GNGGGGN, |
| GGNNGGG, GGNGNGG, GGNGGNG, GGNGGGN, GGGNNGG, GGGNGNG, |
| GGGNGGN, GGGGNNG, GGGGNGN GGGGGGN, NGGGGGG, GNGGGGG, |
| GGNGGGG, GGGNGGG, GGGGNGG, GGGGGNG, GGD, DGG, GDG, GGGD, |
| DGGG, GDGG, GGDG, GGGGD, DGGGG, GDGGG, GGDGG, GGGDG, GGGDD, |
| DDGGG, DGDGG, DGGDG, DGGGD, GDDGG, GDGDG, GDGGD, GGDDG, |
| GGDGD, GGGGGD, DGGGGG, GDGGGG, GGDGGG, GGGDGG, GGGGDG, |
| GGGGDD, DDGGGG, DGDGGG, DGGDGG, DGGGDG, DGGGGD, GDDGGG, |

TABLE 2-continued

| Peptide Motifs having G (Gly) as the Major Constituent (SEQ ID NOS: 905-1728, respectively, in order of appearance) |
|---|
| GDGDGG, GDGGDG, GDGGGD, GGDDGG, GGDGDG, GGDGGD, GGGDDG, GGGDGD, GGGGDDD, DDDGGGG, DGDDGGG, DGDGDGG, DGDGGDG, DGDGGGD, DGGDDGG, DGGDGDG, DGGDGGD, DGGGDGD, DGGGDDG, DGGGGDD, DDGDGGG, DDGGDGG, DDGGGDG, DDGGGGD, GDDDGGG, GDDGDGG, GDDGGDG, GDDGGGD, GDGDDGG, GDGGDDG, GDGGGDD, GDGDGDG, GDGDGGD, GDGGDGD, GGDDDGG, GGDDGDG, GGDDGGD, GGDGDDG, GGDGDGD, GGDGGDD, GGGDDDG, GGGDDGD, GGGDGDD, GGGGGDD, DDGGGGG, DGDGGGG, DGGDGGG, DGGGDGG, DGGGGDG, DGGGGGD, GDDGGGG, GDGDGGG, GDGGDGG, GDGGGDG, GDGGGGD, GGDDGGG, GGDGDGG, GGDGGDG, GGDGGGD, GGGDDGG, GGGDGDG, GGGDGGD, GGGGDDG, GGGGDGD GGGGGGD, DGGGGGG, GDGGGGG, GGDGGGG, GGGDGGG, GGGGDGG, and GGGGGDG. |

TABLE 3

| Peptide Motifs having Q (Gln) as the Major Constituent (SEQ ID NOS: 1729-2449, respectively, in order of appearance) |
|---|
| QQT, TQQ, QTQ, QQQT, TQQQ, QTQQ, QQTQ, QQQQT, TQQQQ, QTQQQ, QQTQQ, QQQTQ, QQQTT, TTQQQ, TQTQQ, TQQTQ, TQQQT, QTTQQ, QTQTQ, QTQQT, QQTTQ, QQTQT, QQQQQT, TQQQQQ, QTQQQQ, QQTQQQ, QQQTQQ, QQQQTQ, QQQQTT, TTQQQQ, TQTQQQ, TQQTQQ, TQQQTQ, TQQQQT, QTTQQQ, QTQTQQ, QTQQTQ, QTQQQT, QQTTQQ, QQTQTQ, QQTQQT, QQQTTQ, QQQTQT, QQQQTTT, TTTQQQQ, TQTTQQQ, TQTQTQQ, TQTQQTQ, TQTQQQT, TQQTTQQ, TQQTQTQ, TQQTQQT, TQQQTQT, TQQQTTQ, TQQQQTT, TTQTQQQ, TTQQTQQ, TTQQQTQ, TTQQQQT, QTTTQQQ, QTTQTQQ, QTTQQTQ, QTTQQQT, QTQTTQQ, QTQQTTQ, QTQQQTT, QTQTQTQ, QTQTQQT, QTQQTQT, QQTTTQQ, QQTTQTQ, QQTTQQT, QQTQTTQ, QQTQTQT, QQTQQTT, QQQTTTQ, QQQTTQT, QQQTQTT, QQQQQTT, TTQQQQQ, TQTQQQQ, TQQTQQQ, TQQQTQQ, TQQQQTQ, TQQQQQT, QTTQQQQ, QTQTQQQ, QTQQTQQ, QTQQQTQ, QTQQQQT, QQTTQQQ, QQTQTQQ, QQTQQTQ, QQTQQQT, QQQTTQQ, QQQTQTQ, QQQTQQT, QQQQTTQ, QQQQTQT QQQQQQT, TQQQQQQ, QTQQQQQ, QQTQQQQ, QQQTQQQ, QQQQTQQ, QQQQQTQ, QQA, AQQ, QAQ, QQQA, AQQQ, QAQQ, QQAQ, QQQQA, AQQQQ, QAQQQ, QQAQQ, QQQAQ, QQQAA, AAQQQ, AQAQQ, AQQAQ, AQQQA, QAAQQ, QAQAQ, QAQQA, QQAAQ, QQAQA, QQQQQA, AQQQQQ, QAQQQQ, QQAQQQ, QQQAQQ, QQQQAQ, QQQQAA, AAQQQQ, AQAQQQ, AQQAQQ, AQQQAQ, AQQQQA, QAAQQQ, QAQAQQ, QAQQAQ, QAQQQA, QQAAQQ, QQAQAQ, QQAQQA, QQQAAQ, QQQAQA, QQQQAAA, AAAQQQQ, AQAAQQQ, |

TABLE 3-continued

| Peptide Motifs having Q (Gln) as the Major Constituent (SEQ ID NOS: 1729-2449, respectively, in order of appearance) |
|---|
| AQAQAQQ, AQAQQAQ, AQAQQQA, AQQAAQQ, AQQAQAQ, AQQAQQA, |
| AQQQAQA, AQQQAAQ, AQQQQAA, AAQAQQQ, AAQQAQQ, AAQQQAQ, |
| AAQQQQA, QAAAQQQ, QAAQAQQ, QAAQQAQ, QAAQQQA, QAQAAQQ, |
| QAQQAAQ, QAQQQAA, QAQAQAQ, QAQAQQA, QAQQAQA, QQAAAQQ, |
| QQAAQAQ, QQAAQQA, QQAQAAQ, QQAQAQA, QQAQQAA, QQQAAAQ, |
| QQQAAQA, QQQAQAA, QQQQQAA, AAQQQQQ, AQAQQQQ, AQQAQQQ, |
| AQQQAQQ, AQQQQAQ, AQQQQQA, QAAQQQQ, QAQAQQQ, QAQQAQQ, |
| QAQQQAQ, QAQQQQA, QQAAQQQ, QQAQAQQ, QQAQQAQ, QQAQQQA, |
| QQQAAQQ, QQQAQAQ, QQQAQQA, QQQQAAQ, QQQQAQA QQQQQQA, |
| AQQQQQQ, QAQQQQQ, QQAQQQQ, QQQAQQQ, QQQQAQQ, QQQQQAQ, |
| QQS, SQQ, QSQ, QQQS, SQQQ, QSQQ, QQSQ, QQQQS, SQQQQ, QSQQQ, |
| QQSQQ, QQQSQ, QQQSS, SSQQQ, SQSQQ, SQQSQ, SQQQS, QSSQQ, QSQSQ, |
| QSQQS, QQSSQ, QQSQS, QQQQQS, SQQQQQ, QSQQQQ, QQSQQQ, QQQSQQ, |
| QQQQSQ, QQQQSS, SSQQQQ, SQSQQQ, SQQSQQ, SQQQSQ, SQQQQS, |
| QSSQQQ, QSQSQQ, QSQQSQ, QSQQQS, QQSSQQ, QQSQSQ, QQSQQS, |
| QQQSSQ, QQQSQS, QQQQSSS, SSSQQQQ, SQSSQQQ, SQSQSQQ, SQSQQSQ, |
| SQSQQQS, SQQSSQQ, SQQSQSQ, SQQSQQS, SQQQSQS, SQQQSSQ, |
| SQQQQSS, SSQSQQQ, SSQQSQQ, SSQQQSQ, SSQQQQS, QSSSQQQ, |
| QSSQSQQ, QSSQQSQ, QSSQQQS, QSQSSQQ, QSQQSSQ, QSQQQSS, |
| QSQSQSQ, QSQSQQS, QSQQSQS, QQSSSQQ, QQSSQSQ, QQSSQQS, |
| QQSQSSQ, QQSQSQS, QQSQQSS, QQQSSSQ, QQQSSQS, QQQSQSS, |
| QQQQQSS, SSQQQQQ, SQSQQQQ, SQQSQQQ, SQQQSQQ, SQQQQSQ, |
| SQQQQQS, QSSQQQQ, QSQSQQQ, QSQQSQQ, QSQQQSQ, QSQQQQS, |
| QQSSQQQ, QQSQSQQ, QQSQQSQ, QQSQQQS, QQQSSQQ, QQQSQSQ, |
| QQQSQQS, QQQQSSQ, QQQQSQS QQQQQQS, SQQQQQQ, QSQQQQQ, |
| QQSQQQQ, QQQSQQQ, QQQQSQQ, QQQQQSQ, QQE, EQQ, QEQ, QQQE, |
| EQQQ, QEQQ, QQEQ, QQQQE, EQQQQ, QEQQQ, QQEQQ, QQQEQ, QQQEE, |
| EEQQQ, EQEQQ, EQQEQ, EQQQE, QEEQQ, QEQEQ, QEQQE, QQEEQ, |
| QQEQE, QQQQQE, EQQQQQ, QEQQQQ, QQEQQQ, QQQEQQ, QQQQEQ, |
| QQQQEE, EEQQQQ, EQEQQQ, EQQEQQ, EQQQEQ, EQQQQE, QEEQQQ, |
| QEQEQQ, QEQQEQ, QEQQQE, QQEEQQ, QQEQEQ, QQEQQE, QQQEEQ, |
| QQQEQE, QQQQEEE, EEEQQQQ, EQEEQQQ, EQEQEQQ, EQEQQEQ, |
| EQEQQQE, EQQEEQQ, EQQEQEQ, EQQEQQE, EQQQEQE, EQQQEEQ, |
| EQQQQEE, EEQEQQQ, EEQQEQQ, EEQQQEQ, EEQQQQE, QEEEQQQ, |
| QEEQEQQ, QEEQQEQ, QEEQQQE, QEQEEQQ, QEQQEEQ, QEQQQEE, |
| QEQEQEQ, QEQEQQE, QEQQEQE, QQEEEQQ, QQEEQEQ, QQEEQQE, |
| QQEQEEQ, QQEQEQE, QQEQQEE, QQQEEEQ, QQQEEQE, QQQEQEE, |
| QQQQQEE, EEQQQQQ, EQEQQQQ, EQQEQQQ, EQQQEQQ, EQQQQEQ, |
| EQQQQQE, QEEQQQQ, QEQEQQQ, QEQQEQQ, QEQQQEQ, QEQQQQE, |

TABLE 3-continued

| Peptide Motifs having Q (Gln) as the Major Constituent (SEQ ID NOS: 1729-2449, respectively, in order of appearance) |
|---|
| QQEEQQQ, QQEQEQQ, QQEQQEQ, QQEQQQE, QQQEEQQ, QQQEQEQ, |
| QQQEQQE, QQQQEEQ, QQQQEQE QQQQQQE, EQQQQQQ, QEQQQQQ, |
| QQEQQQQ, QQQEQQQ, QQQQEQQ, QQQQQEQ, QQH, HQQ, QHQ, QQQH, |
| HQQQ, QHQQ, QQHQ, QQQQH, HQQQQ, QHQQQ, QQHQQ, QQQHQ, QQQHH, |
| HHQQQ, HQHQQ, HQQHQ, HQQQH, QHHQQ, QHQHQ, QHQQH, QQHHQ, |
| QQHQH, QQQQQH, HQQQQQ, QHQQQQ, QQHQQQ, QQQHQQ, QQQQHQ, |
| QQQQHH, HHQQQQ, HQHQQQ, HQQHQQ, HQQQHQ, HQQQQH, QHHQQQ, |
| QHQHQQ, QHQQHQ, QHQQQH, QQHHQQ, QQHQHQ, QQHQQH, QQQHHQ, |
| QQQHQH, QQQQHHH, HHHQQQQ, HQHHQQQ, HQHQHQQ, HQHQQHQ, |
| HQHQQQH, HQQHHQQ, HQQHQHQ, HQQHQQH, HQQQHQH, HQQQHHQ, |
| HQQQQHH, HHQHQQQ, HHQQHQQ, HHQQQHQ, HHQQQQH, QHHHQQQ, |
| QHHQHQQ, QHHQQHQ, QHHQQQH, QHQHHQQ, QHQQHHQ, QHQQQHH, |
| QHQHQHQ, QHQHQQH, QHQQHQH, QQHHHQQ, QQHHQHQ, QQHHQQH, |
| QQHQHHQ, QQHQHQH, QQHQQHH, QQQHHHQ, QQQHHQH, QQQHQHH, |
| QQQQQHH, HHQQQQQ, HQHQQQQ, HQQHQQQ, HQQQHQQ, HQQQQHQ, |
| HQQQQQH, QHHQQQQ, QHQHQQQ, QHQQHQQ, QHQQQHQ, QHQQQQH, |
| QQHHQQQ, QQHQHQQ, QQHQQHQ, QQHQQQH, QQQHHQQ, QQQHQHQ, |
| QQQHQQH, QQQQHHQ, QQQQHQH QQQQQQH, HQQQQQQ, QHQQQQQ, |
| QQHQQQQ, QQQHQQQ, QQQQHQQ, QQQQQHQ, QQN, NQQ, QNQ, QQQN, |
| NQQQ, QNQQ, QQNQ, QQQQN, NQQQQ, QNQQQ, QQNQQ, QQQNQ, QQQNN, |
| NNQQQ, NQNQQ, NQQNQ, NQQQN, QNNQQ, QNQNQ, QNQQN, QQNNQ, |
| QQNQN, QQQQQN, NQQQQQ, QNQQQQ, QQNQQQ, QQQNQQ, QQQQNQ, |
| QQQQNN, NNQQQQ, NQNQQQ, NQQNQQ, NQQQNQ, NQQQQN, QNNQQQ, |
| QNQNQQ, QNQQNQ, QNQQQN, QQNNQQ, QQNQNQ, QQNQQN, QQQNNQ, |
| QQQNQN, QQQQNNN, NNNQQQQ, NQNNQQQ, NQNQNQQ, NQNQQNQ, |
| NQNQQQN, NQQNNQQ, NQQNQNQ, NQQNQQN, NQQQNQN, NQQQNNQ, |
| NQQQQNN, NNQNQQQ, NNQQNQQ, NNQQQNQ, NNQQQQN, QNNNQQQ, |
| QNNQNQQ, QNNQQNQ, QNNQQQN, QNQNNQQ, QNQQNNQ, QNQQQNN, |
| QNQNQNQ, QNQNQQN, QNQQNQN, QQNNNQQ, QQNNQNQ, QQNNQQN, |
| QQNQNNQ, QQNQNQN, QQNQQNN, QQQNNNQ, QQQNNQN, QQQNQNN, |
| QQQQQNN, NNQQQQQ, NQNQQQQ, NQQNQQQ, NQQQNQQ, NQQQQNQ, |
| NQQQQQN, QNNQQQQ, QNQNQQQ, QNQQNQQ, QNQQQNQ, QNQQQQN, |
| QQNNQQQ, QQNQNQQ, QQNQQNQ, QQNQQQN, QQQNNQQ, QQQNQNQ, |
| QQQNQQN, QQQQNNQ, QQQQNQN QQQQQQN, NQQQQQQ, QNQQQQQ, |
| QQNQQQQ, QQQNQQQ, QQQQNQQ, QQQQQNQ, QQD, DQQ, QDQ, QQQD, |
| DQQQ, QDQQ, QQDQ, QQQQD, DQQQQ, QDQQQ, QQDQQ, QQQDQ, QQQDD, |
| DDQQQ, DQDQQ, DQQDQ, DQQQD, QDDQQ, QDQDQ, QDQQD, QQDDQ, |
| QQDQD, QQQQQD, DQQQQQ, QDQQQQ, QQDQQQ, QQQDQQ, QQQQDQ, |

TABLE 3-continued

| Peptide Motifs having Q (Gln) as the Major Constituent (SEQ ID NOS: 1729-2449, respectively, in order of appearance) |
|---|
| QQQQDD, DDQQQQ, DQDQQQ, DQQDQQ, DQQQDQ, DQQQQD, QDDQQQ, |
| QDQDQQ, QDQQDQ, QDQQQD, QQDDQQ, QQDQDQ, QQDQQD, QQQDDQ, |
| QQQDQD, QQQQDDD, DDDQQQQ, DQDDQQQ, DQDQDQQ, DQDQQDQ, |
| DQDQQQD, DQQDDQQ, DQQDQDQ, DQQDQQD, DQQQDQD, DQQQDDQ, |
| DQQQQDD, DDQDQQQ, DDQQDQQ, DDQQQDQ, DDQQQQD, QDDDQQQ, |
| QDDQDQQ, QDDQQDQ, QDDQQQD, QDQDDQQ, QDQQDDQ, QDQQQDD, |
| QDQDQDQ, QDQDQQD, QDQQDQD, QQDDDQQ, QQDDQDQ, QQDDQQD, |
| QQDQDDQ, QQDQDQD, QQDQQDD, QQQDDDQ, QQQDDQD, QQQDQDD, |
| QQQQQDD, DDQQQQQ, DQDQQQQ, DQQDQQQ, DQQQDQQ, DQQQQDQ, |
| DQQQQQD, QDDQQQQ, QDQDQQQ, QDQQDQQ, QDQQQDQ, QDQQQQD, |
| QQDDQQQ, QQDQDQQ, QQDQQDQ, QQDQQQD, QQQDDQQ, QQQDQDQ, |
| QQQDQQD, QQQQDDQ, QQQQDQD QQQQQQD, DQQQQQQ, QDQQQQQ, |
| QQDQQQQ, QQQDQQQ, QQQQDQQ, and QQQQQDQ. |

TABLE 4

(SEQ ID NO: 2450)

```
        10         20         30         40         50         60
MFLQNLFLGF LAVVCANATP LGPASSLPQS FLLKCLEQVR KIQGDGAALQ EKLCATYKLC

        70         80         90        100        110        120
HPEELVLLGH SLGIPWAPLS SCPSQALQLA GCLSQLHSGL FLYQGLLQAL EGISPELGPT

       130        140        150        160        170        180
LDTLQLDVAD FATTIWQQME ELGMAPALQP TQGAMPAFAS AFQRRAGGVL VASHLQSFLE

       190        200        210        220        230        240
VSYRVLRHLA QPNNTNNTNN TNNTNNTNNT NNTNNTNNTN NTNNTNNTNN TNNTNNTNNT

       250        260        270        280        290        300
NNTNNTNNTN NTNNTNNTNN TNNTNNTNNT NNTNNTNNTN NTNNTNNTNN TNNTNNTNNT

       310        320        330        340        350         360
NNTNNTNNTN NTNNTNNTNN TNNTNNTNNT NNTNNTNNTN NTNNTNN*|.. ..........
```

(SEQ ID NO: 2451)

```
        10         20         30         40         50         60
atgttcttgc aaaatttatt ccttggcttt ttggccgttg tttgcgcaaa cgcgACTCCG

        70         80         90         100        110        120
CTGGGTCCAG CTAGCTCCCT GCCCCAGAGC TTCCTGCTCA AGTGCTTAGA GCAAGTGAGG

       130        140        150        160        170        180
AAGATCCAGG GCGATGGCGC AGCGCTCCAG GAGAAGCTGT GTGCCACCTA CAAGCTGTGC

       190        200        210        220        230        240
CACCCCGAGG AGCTGGTGCT GCTCGGACAC TCTCTGGGCA TCCCCTGGGC TCCCCTGAGC

       250        260        270        280        290        300
AGCTGCCCCA GCCAGGCCCT GCAGCTGGCA GGCTGCTTGA GCCAACTCCA TAGCGGCCTT

       310        320        330        340        350        360
TTCCTCTACC AGGGGCTCCT GCAGGCCCTG GAAGGGATCT CCCCCGAGTT GGGTCCCACC

       370        380        390        400        410        420
TTGGACACAC TGCAGCTGGA CGTCGCCGAC TTTGCCACCA CCATCTGGCA GCAGATGGAA

        430        440        450        460        470        480
|GAACTGGGAA TGGCCCCTGC CCTGCAGCCG ACCCAGGGTG CCATGCCGGC CTTCGCCTCT
```

TABLE 4-continued

| | | | | | |
|---|---|---|---|---|---|
| 490 | 500 | 510 | 520 | 530 | 540 |
| GCTTTCCAGC | GCCGGGCAGG | AGGGGTCCTA | GTTGCCTCCC | ATCTGCAGAG | CTTCCTGGAG |
| 550 | 560 | 570 | 580 | 590 | 600 |
| GTGTCGTACC | GCGTTCTACG | CCACCTTGCC | CAGCCTAACA | ACACCAACAA | TACCAACAAT |
| 610 | 620 | 630 | 640 | 650 | 660 |
| ACAAACAACA | CCAACAATAC | CAACAATACA | AACAACACCA | ACAATACCAA | CAATACAAAC |
| 670 | 680 | 690 | 700 | 710 | 720 |
| AACACCAACA | ATACCAACAA | TACAAACAAC | ACCAACAATA | CCAACAATAC | AAACAACACC |
| 730 | 740 | 750 | 760 | 770 | 780 |
| AACAATACCA | ACAATACAAA | CAACACCAAC | AATACCAACA | ATACAAACAA | CACCAATAAT |
| 790 | 800 | 810 | 820 | 830 | 840 |
| ACCAACAATA | CAAACAACAC | CAATAATACC | AACAATACAA | ACAACACCAA | TAATACCAAC |
| 850 | 860 | 870 | 880 | 890 | 900 |
| AATACAAACA | ACACCAATAA | TACCAACAAT | ACAAACAACA | CCAATAATAC | CAACAATACA |
| 910 | 920 | 930 | 940 | 950 | 960 |
| AACAACACCA | ATAATACCAA | CAATACAAAC | AACACCAATA | ATACCAACAA | TACAAACAAC |
| 970 | 980 | 990 | 1000 | 1010 | 1020 |
| ACCAATAATA | CCAACAATAC | AAACAACACC | AATAATACCA | ACAATACAAA | CAACACCAAT |
| 1030 | 1040 | 1050 | 1060 | 1070 | 1080 |
| AATACCAACA | ATACAAACAA | CTAG...... | .......... | .......... | .......... |

TABLE 5

EPO
*Homo sapiens* erythropoietin (EPO), mRNA.
ACCESSION NM_000799
VERSION NM_000799.2 GI: 62240996

MGVHECPAWLWLLLSLLSLPLGLPVLGAPPRLICDSRVLERYLLEAKEAENITT
GCAEHCSLNENITVPDTKVNFYAWKRMEVGQQAVEVWQGLALLSEAVLRG
QALLVNSSQPWEPLQLHVDKAVSGLRSLTTLLRALGAQKEAISPPDAASAAPL
RTITADTFRKLFRVYSNFLRGKLKLYTGEACRTGDR (SEQ ID NO: 2452)

1 cccggagccg gaccggggcc accgcgcccg ctctgctccg acaccgcgcc ccctggacag 61 ccgccctctc ctccaggccc gtggggctgg ccctgcaccg ccgagcttcc cgggatgagg 121 gcccccggtg tggtcacccg gcgcgcccca ggtcgctgag ggaccccggc caggcgcgga 181 gatgggggtg cacgaatgtc ctgcctggct gtggcttctc ctgtccctgc tgtcgctccc 241 tctgggcctc ccagtcctgg gcgccccacc acgcctcatc tgtgacagcc gagtcctgga 301 gaggtacctc ttggaggcca aggaggccga gaatatcacg acgggctgtg ctgaacactg 361 cagcttgaat gagaatatca ctgtcccaga caccaaagtt aatttctatg cctggaagag 421 gatggaggtc gggcagcagg ccgtagaagt ctggcagggc ctggccctgc tgtcggaagc 481 tgtcctgcgg ggccaggccc tgttggtcaa ctcttcccag ccgtgggagc ccctgcagct 541 gcatgtggat aaagccgtca gtggccttcg cagcctcacc actctgcttc gggctctggg 601 agcccagaag gaagccatct cccctccaga tgcggcctca gctgctccac tccgaacaat 661 cactgctgac actttccgca aactcttccg agtctactcc aatttcctcc ggggaaagct 721 gaagctgtac acaggggagg cctgcaggac aggggacaga tgaccaggtg tgtccacctg 781 ggcatatcca ccacctccct caccaacatt gcttgtgcca caccctcccc cgccactcct 841 gaaccccgtc gaggggctct cagctcagcg ccagcctgtc ccatggacac tccagtgcca 901 gcaatgacat ctcaggggcc agaggaactg tccagagagc aactctgaga tctaaggatg 961 tcacagggcc aacttgaggg cccagagcag gaagcattca gagagcagct ttaaactcag 1021 ggacagagcc atgctgggaa gacgcctgag ctcactcggc accctgcaaa atttgatgcc TABLE 5-continued 1081 aggacacgct ttggaggcga tttacctgtt ttcgcaccta ccatcaggga caggatgacc 1141 tggagaactt aggtggcaag ctgtgacttc tccaggtctc acgggcatgg gcactccctt 1201 ggtggcaaga gccccttga caccggggtg gtgggaacca tgaagacagg atgggggctg 1261 gcctctggct ctcatggggt ccaagttttg tgtattcttc aacctcattg acaagaactg 1321 aaaccaccaa aaaaaaaaaa (SEQ ID NO: 2453)

MCSF
*Homo sapiens* colony stimulating factor 1 (macrophage) (CSF1), transcript variant 4, mRNA.
ACCESSION NM_172212
VERSION NM_172212.1 GI: 27262666

MTAPGAAGRCPPTTWLGSLLLLVCLLASRSITEEVSEYCSHMIGSGHLQSLQR
LIDSQMETSCQITFEFVDQEQLKDPVCYLKKAFLLVQDIMEDTMRFRDNTPNA
IAIVQLQELSLRLKSCFTKDYEEHDKACVRTFYETPLQLLEKVKNVFNETKNLL
DKDWNIFSKNCNNSFAECSSQDVVTKPDCNCLYPKAIPSSDPASVSPHQPLAP
SMAPVAGLTWEDSEGTEGSSLLPGEQPLHTVDPGSAKQRPPRSTCQSFEPPET
PVVKDSTIGGSPQPRPSVGAFNPGMEDILDSAMGTNWVPEEASGEASEIPVPQ
GTELSPSRPGGGSMQTEPARPSNFLSASSPLPASAKGQQPADVTGTALPRVGP
VRPTGQDWNHTPQKTDHPSALLRDPPEPGSPRISSLRPQGLSNPSTLSAQPQLS
RSHSSGSVLPLGELEGRRSTRDRRSPAEPEGGPASEGAARPLPRFNSVPLTDTG
HERQSEGSSSPQLQESVFHLLVPSVILVLLAVGGLLFYRWRRRSHQEPQRADS
PLEQPEGSPLTQDDRQVELPV (SEQ ID NO: 2454)

1 gagggctggc cagtgaggct cggcccgggg aaagtgaaag tttgcctggg tcctctcggc 61 gccagagccg ctctccgcat cccaggacag cggtgcggcc ctcggccggg gcgcccactc 121 cgcagcagcc agcgagcgag cgagcgagcg agggcggccg acgcgcccgg ccgggaccca 181 gctgcccgta tgaccgcgcc gggcgccgcc gggcgctgcc ctcccacgac atggctgggc 241 tccctgctgt tgttggtctg tctcctggcg agcaggagta tcaccgagga ggtgtcggag 301 tactgtagcc acatgattgg gagtggacac ctgcagtctc tgcagcggct gattgacagt 361 cagatggaga cctcgtgcca aattacattt gagtttgtag accaggaaca gttgaaagat 421 ccagtgtgct accttaagaa ggcatttctc ctggtacaag acataatgga ggacaccatg 481 cgcttcagag ataacacccc caatgccatc gccattgtgc agctgcagga actctctttg 541 aggctgaaga gctgcttcac caaggattat gaagagcatg acaaggcctg cgtccgaact 601 ttctatgaga cacctctcca gttgctggag aaggtcaaga atgtctttaa tgaaacaaag 661 aatctccttg acaaggactg gaatattttc agcaagaact gcaacaacag ctttgctgaa 721 tgctccagcc aagatgtggt gaccaagcct gattgcaact gcctgtaccc caaagccatc 781 cctagcagtg acccggcctc tgtctcccct catcagcccc tcgcccccctc catggcccct 841 gtggctggct tgacctggga ggactctgag ggaactgagg gcagctccct cttgcctggt 901 gagcagcccc tgcacacagt ggatccaggc agtgccaagc agcggccacc caggagcacc 961 tgccagagct ttgagccgcc agagacccca gttgtcaagg acagcaccat cggtggctca 1021 ccacagcctc gcccctctgt cggggccttc aaccccggga tggaggatat tcttgactct 1081 gcaatgggca ctaattgggt cccagaagaa gcctctggag aggccagtga gattcccgta 1141 ccccaaggga cagagctttc cccctccagg ccaggagggg gcagcatgca gacagagccc 1201 gccagaccca gcaacttcct ctcagcatct tctccactcc ctgcatcagc aaagggccaa 1261 cagccggcag atgtaactgg tacagccttg cccagggtgg gccccgtgag gcccactggc 1321 caggactgga atcacacccc ccagaagaca gaccatccat ctgccctgct cagagacccc 1381 ccggagccag gctctcccag gatctcatca ctgcgccccc agggcctcag caaccccctcc 1441 accctctctg ctcagccaca gctttccaga agccactcct cgggcagcgt gctgcccctt 1501 ggggagctgg agggcaggag gagcaccagg gatcggagga gccccgcaga gccagaagga TABLE 5-continued 1561 ggaccagcaa gtgaaggggc agccaggccc ctgccccgtt ttaactccgt tcctttgact 1621 gacacaggcc atgagaggca gtccgaggga tcctccagcc cgcagctcca ggagtctgtc 1681 ttccacctgc tggtgcccag tgtcatcctg gtcttgctgg ccgtcggagg cctcttgttc 1741 tacaggtgga ggcggcggag ccatcaagag cctcagagag cggattctcc cttggagcaa 1801 ccagagggca gcccccctgac tcaggatgac agacaggtgg aactgccagt gtagagggaa 1861 ttctaagacc cctcaccatc ctggacacac tcgtttgtca atgtccctct gaaaatgtga 1921 cgcccagccc cggacacagt actccagatg ttgtctgacc agctcagaga gagtacagtg 1981 ggactgttac cttccttgat atggacagta ttcttctatt tgtgcagatt aagattgcat 2041 tagttttttt cttaacaact gcatcatact gttgtcatat gttgagcctg tggttctata 2101 aaacccctag ttccatttcc cataaacttc tgtcaagcca gaccatctct accctgtact 2161 tggacaactt aactttttta accaaagtgc agtttatgtt cacctttgtt aaagccacct 2221 ttgtggtttc tgcccatcac ctgaacctac tgaagttgtg tgaaatccta attctgtcat 2281 ctccgtagcc ctcccagttg tgcctcctgc acattgatga gtgcctgctg ttgtctttgc 2341 ccatgttgtt gatgtagctg tgaccctatt gttcctcacc cctgcccccc gccaacccca 2401 gctggcccac ctcttccccc tcccacccaa gcccacagcc agcccatcag gaagccttcc 2461 tggcttctcc acaaccttct gactgtcttt tcagtcatgc cccctgctct tttgtatttg 2521 gctaatagta tatcaatttg cactt (SEQ ID NO: 2455)

*Homo sapiens* colony stimulating factor 1 (macrophage) (CSF1),
transcript variant 3, mRNA.
ACCESSION NM_172211
VERSION NM_172211.1 GI: 27262664

MTAPGAAGRCPPTTWLGSLLLLVCLLASRSITEEVSEYCSHMIGSGHLQSLQR
LIDSQMETSCQITFEFVDQEQLKDPVCYLKKAFLLVQDIMEDTMRFRDNTPNA
IAIVQLQELSLRLKSCFTKDYEEHDKACVRTFYETPLQLLEKVKNVFNETKNLL
DKDWNIFSKNCNNSFAECSSQGHERQSEGSSSPQLQESVFHLLVPSVILVLLAV
GGLLFYRWRRRSHQEPQRADSPLEQPEGSPLTQDDRQVELPV (SEQ ID NO: 2456)

1 gagggctggc cagtgaggct cggcccgggg aaagtgaaag tttgcctggg tcctctcggc 61 gccagagccg ctctccgcat cccaggacag cggtgcggcc ctcggccggg gcgcccactc 121 cgcagcagcc agcgagcgag cgagcgagcg agggcggccg acgcgcccgg ccgggaccca 181 gctgcccgta tgaccgcgcc gggcgccgcc gggcgctgcc ctcccacgac atggctgggc 241 tccctgctgt tgttggtctg tctcctggcg agcaggagta tcaccgagga ggtgtcggag 301 tactgtagcc acatgattgg gagtggacac ctgcagtctc tgcagcggct gattgacagt 361 cagatggaga cctcgtgcca aattacattt gagtttgtag accaggaaca gttgaaagat 421 ccagtgtgct accttaagaa ggcatttctc ctggtacaag acataatgga ggacaccatg 481 cgcttcagag ataacacccc caatgccatc gccattgtgc agctgcagga actctctttg 541 aggctgaaga gctgcttcac caaggattat gaagagcatg acaaggcctg cgtccgaact 601 ttctatgaga cacctctcca gttgctggag aaggtcaaga atgtctttaa tgaaacaaag 661 aatctccttg acaaggactg gaatattttc agcaagaact gcaacaacag ctttgctgaa 721 tgctccagcc aaggccatga gaggcagtcc gagggatcct ccagcccgca gctccaggag 781 tctgtcttcc acctgctggt gcccagtgtc atcctggtct tgctggccgt cggaggcctc 841 ttgttctaca ggtggaggcg gcggagccat caagagcctc agagagcgga ttctcccttg 901 gagcaaccag agggcagccc cctgactcag gatgacagac aggtggaact gccagtgtag 961 agggaattct aagctggacg cacagaacag tctctccgtg ggaggagaca ttatggggcg TABLE 5-continued

```
1021 tccaccacca cccctccctg gccatcctcc tggaatgtgg tctgccctcc accagagctc

1081 ctgcctgcca ggactggacc agagcagcca ggctggggcc cctctgtctc aacccgcaga

1141 cccttgactg aatgagagag gccagaggat gctccccatg ctgccactat ttattgtgag

1201 ccctggaggc tcccatgtgc ttgaggaagg ctggtgagcc cggctcagga ccctcttccc

1261 tcaggggctg caccctcctc tcactccctt ccatgccgga acccaggcca gggacccacc

1321 ggcctgtggt ttgtgggaaa gcagggtgga cgctgaggag tgaaagaacc ctgcacccag

1381 agggcctgcc tggtgccaag gtatcccagc ctggacaggc atggacctgt ctccagagag

1441 aggagcctga agttcgtggg gcgggacagc gtcggcctga tttcccgtaa aggtgtgcag

1501 cctgagagac gggaagagga ggcctctgga cctgctggtc tgcactgaca gcctgaaggg

1561 tctacaccct cggctcacct aagtgccctg tgctggttgc caggcgcaga ggggaggcca

1621 gccctgccct caggacctgc ctgacctgcc agtgatgcca agagggggat caagcactgg

1681 cctctgcccc tcctccttcc agcacctgcc agagcttctc caggaggcca agcagaggct

1741 cccctcatga aggaagccat tgcactgtga acactgtacc tgcctgctga acagcctgcc

1801 cccgtccatc catgagccag catccgtccg tcctccactc tccagcctct cccca (SEQ ID NO: 2457)
```

*Homo sapiens* colony stimulating factor 1 (macrophage) (CSF1),
transcript variant 2, mRNA.
ACCESSION NM_172210
VERSION NM_172210.1 GI: 27262662

```
MTAPGAAGRCPPTTWLGSLLLLVCLLASRSITEEVSEYCSHMIGSGHLQSLQR
LIDSQMETSCQITFEFVDQEQLKDPVCYLKKAFLLVQDIMEDTMRFRDNTPNA
IAIVQLQELSLRLKSCFTKDYEEHDKACVRTFYETPLQLLEKVKNVFNETKNLL
DKDWNIFSKNCNNSFAECSSQDVVTKPDCNCLYPKAIPSSDPASVSPHQPLAP
SMAPVAGLTWEDSEGTEGSSLLPGEQPLHTVDPGSAKQRPPRSTCQSFEPPET
PVVKDSTIGGSPQPRPSVGAFNPGMEDILDSAMGTNWVPEEASGEASEIPVPQ
GTELSPSRPGGGSMQTEPARPSNFLSASSPLPASAKGQQPADVTGHERQSEGS
SSPQLQESVFHLLVPSVILVLLAVGGLLFYRWRRRSHQEPQRADSPLEQPEGSP
LTQDDRQVELPV (SEQ ID NO: 2458)
```

```
   1 gagggctggc cagtgaggct cggcccgggg aaagtgaaag tttgcctggg tcctctcggc

  61 gccagagccg ctctccgcat cccaggacag cggtgcggcc ctcggccggg gcgcccactc

 121 cgcagcagcc agcgagcgag cgagcgagcg agggcggccg acgcgcccgg ccgggaccca

 181 gctgcccgta tgaccgcgcc gggcgccgcc gggcgctgcc ctcccacgac atggctgggc

 241 tccctgctgt tgttggtctg tctcctggcg agcaggagta tcaccgagga ggtgtcggag

 301 tactgtagcc acatgattgg gagtggacac ctgcagtctc tgcagcggct gattgacagt

 361 cagatggaga cctcgtgcca aattacattt gagtttgtag accaggaaca gttgaaagat

 421 ccagtgtgct accttaagaa ggcatttctc ctggtacaag acataatgga ggacaccatg

 481 cgcttcagag ataacacccc caatgccatc gccattgtgc agctgcagga actctctttg

 541 aggctgaaga gctgcttcac caaggattat gaagagcatg acaaggcctg cgtccgaact

 601 ttctatgaga cacctctcca gttgctggag aaggtcaaga atgtctttaa tgaaacaaag

 661 aatctccttg acaaggactg gaatattttc agcaagaact gcaacaacag ctttgctgaa

 721 tgctccagcc aagatgtggt gaccaagcct gattgcaact gcctgtaccc caaagccatc

 781 cctagcagtg acccggcctc tgtctcccct catcagcccc tcgccccctc catggcccct

 841 gtggctggct tgacctggga ggactctgag ggaactgagg gcagctccct cttgcctggt

 901 gagcagcccc tgcacacagt ggatccaggc agtgccaagc agcggccacc caggagcacc

 961 tgccagagct ttgagccgcc agagacccca gttgtcaagg acagcaccat cggtggctca

1021 ccacagcctc gcccctctgt cggggccttc aaccccggga tggaggatat tcttgactct

1081 gcaatgggca ctaattgggt cccagaagaa gcctctggag aggccagtga gattcccgta
```

TABLE 5-continued 1141 ccccaaggga cagagctttc cccctccagg ccaggagggg gcagcatgca gacagagccc 1201 gccagaccca gcaacttcct ctcagcatct tctccactcc ctgcatcagc aaagggccaa 1261 cagccggcag atgtaactgg ccatgagagg cagtccgagg gatcctccag cccgcagctc 1321 caggagtctg tcttccacct gctggtgccc agtgtcatcc tggtcttgct ggccgtcgga 1381 ggcctcttgt tctacaggtg gaggcggcgg agccatcaag agcctcagag agcggattct 1441 cccttggagc aaccagaggg cagccccctg actcaggatg acagacaggt ggaactgcca 1501 gtgtagaggg aattctaag (SEQ ID NO: 2459)

*Homo sapiens* colony stimulating factor 1 (macrophage) (CSF1), transcript variant 1, mRNA.
ACCESSION NM_000757
VERSION NM_000757.3 GI: 27262660

MTAPGAAGRCPPTTWLGSLLLLVCLLASRSITEEVSEYCSHMIGSGHLQSLQR
LIDSQMETSCQITFEFVDQEQLKDPVCYLKKAFLLVQDIMEDTMRFRDNTPNA
IAIVQLQELSLRLKSCFTKDYEEHDKACVRTFYETPLQLLEKVKNFVFNETKNLL
DKDWNIFSKNCNNSFAECSSQDVVTKPDCNCLYPKAIPSSDPASVSPHQPLAP
SMAPVAGLTWEDSEGTEGSSLLPGEQPLHTVDPGSAKQRPPRSTCQSFEPPET
PVVKDSTIGGSPQPRPSVGAFNPGMEDILDSAMGTNWVPEEASGEASEIPVPQ
GTELSPSRPGGGSMQTEPARPSNFLSASSPLPASAKGQQPADVTGTALPRVGP
VRPTGQDWNHTPQKTDHPSALLRDPPEPGSPRISSLRPQGLSNPSTLSAQPQLS
RSHSSGSVLPLGELEGRRSTRDRRSPAEPEGGPASEGAARPLPRFNSVPLTDTG
HERQSEGSSSPQLQESVFHLLVPSVILVLLAVGGLLFYRWRRRSHQEPQRADS
PLEQPEGSPLTQDDRQVELPV (SEQ ID NO: 2460)

1 gagggctggc cagtgaggct cggcccgggg aaagtgaaag tttgcctggg tcctctcggc 61 gccagagccg ctctccgcat cccaggacag cggtgcggcc ctcggccggg gcgcccactc 121 cgcagcagcc agcgagcgag cgagcgagcg agggcggccg acgcgcccgg ccgggaccca 181 gctgcccgta tgaccgcgcc gggcgccgcc gggcgctgcc ctcccacgac atggctgggc 241 tccctgctgt tgttggtctg tctcctggcg agcaggagta tcaccgagga ggtgtcggag 301 tactgtagcc acatgattgg gagtggacac ctgcagtctc tgcagcggct gattgacagt 361 cagatggaga cctcgtgcca aattacattt gagtttgtag accaggaaca gttgaaagat 421 ccagtgtgct accttaagaa ggcatttctc ctggtacaag acataatgga ggacaccatg 481 cgcttcagag ataacacccc caatgccatc gccattgtgc agctgcagga actctctttg 541 aggctgaaga gctgcttcac caaggattat gaagagcatg acaaggcctg cgtccgaact 601 ttctatgaga cacctctcca gttgctggag aaggtcaaga atgtctttaa tgaaacaaag 661 aatctccttg acaaggactg gaatattttc agcaagaact gcaacaacag ctttgctgaa 721 tgctccagcc aagatgtggt gaccaagcct gattgcaact gcctgtaccc caaagccatc 781 cctagcagtg acccggcctc tgtctcccct catcagcccc tcgcccccte catggcccct 841 gtggctggct tgacctggga ggactctgag ggaactgagg gcagctccct cttgcctggt 901 gagcagcccc tgcacacagt ggatccaggc agtgccaagc agcggccacc caggagcacc 961 tgccagagct ttgagccgcc agagacccca gttgtcaagg acagcaccat cggtggctca 1021 ccacagcctc gcccctctgt cggggccttc aaccccggga tggaggatat tcttgactct 1081 gcaatgggca ctaattgggt cccagaagaa gcctctggag aggccagtga gattcccgta 1141 ccccaaggga cagagctttc cccctccagg ccaggagggg gcagcatgca gacagagccc 1201 gccagaccca gcaacttcct ctcagcatct tctccactcc ctgcatcagc aaagggccaa 1261 cagccggcag atgtaactgg tacagccttg cccagggtgg gccccgtgag gcccactggc 1321 caggactgga atcacacccc ccagaagaca gaccatccat ctgccctgct cagagacccc 1381 ccggagccag gctctcccag gatctcatca ctgcgccccc agggcctcag caacccctcc TABLE 5-continued 1441 accctctctg ctcagccaca gctttccaga agccactcct cgggcagcgt gctgcccctt 1501 ggggagctgg agggcaggag gagcaccagg gatcggagga gccccgcaga gccagaagga 1561 ggaccagcaa gtgaaggggc agccaggccc ctgccccgtt ttaactccgt tcctttgact 1621 gacacaggcc atgagaggca gtccgaggga tcctccagcc cgcagctcca ggagtctgtc 1681 ttccacctgc tggtgcccag tgtcatcctg gtcttgctgg ccgtcggagg cctcttgttc 1741 tacaggtgga ggcggcggag ccatcaagag cctcagagag cggattctcc cttggagcaa 1801 ccagagggca gccccctgac tcaggatgac agacaggtgg aactgccagt gtagagggaa 1861 ttctaagctg gacgcacaga acagtctctc cgtgggagga gacattatgg ggcgtccacc 1921 accacccctc cctggccatc ctcctggaat gtggtctgcc ctccaccaga gctcctgcct 1981 gccaggactg gaccagagca gccaggctgg ggcccctctg tctcaacccg cagacccttg 2041 actgaatgag agaggccaga ggatgctccc catgctgcca ctatttattg tgagccctgg 2101 aggctcccat gtgcttgagg aaggctggtg agcccggctc aggaccctct tccctcaggg 2161 gctgcaccct cctctcactc ccttccatgc cggaacccag gccagggacc caccggcctg 2221 tggtttgtgg gaaagcaggg tggacgctga ggagtgaaag aaccctgcac ccagagggcc 2281 tgcctggtgc caaggtatcc cagcctggac aggcatggac ctgtctccag agagaggagc 2341 ctgaagttcg tggggcggga cagcgtcggc ctgatttccc gtaaaggtgt gcagcctgag 2401 agacgggaag aggaggcctc tggacctgct ggtctgcact gacagcctga agggtctaca 2461 ccctcggctc acctaagtgc cctgtgctgg ttgccaggcg cagaggggag gccagccctg 2521 ccctcaggac ctgcctgacc tgccagtgat gccaagaggg ggatcaagca ctggcctctg 2581 cccctcctcc ttccagcacc tgccagagct tctccaggag gccaagcaga ggctcccctc 2641 atgaaggaag ccattgcact gtgaacactg tacctgcctg ctgaacagcc tgcccccgtc 2701 catccatgag ccagcatccg tccgtcctcc actctccagc ctctcccca (SEQ ID NO: 2461)

GM-CSF
*Homo sapiens* colony stimulating factor 2 (granulocyte-macrophage)
(CSF2), mRNA.
ACCESSION NM_000758
VERSION NM_000758.2 GI: 27437029

MWLQSLLLLGTVACSISAPARSPSPSTQPWEHVNAIQEARRLLN
LSRDTAAEMNETVEVISEMFDLQEPTCLQTRLELYKQGLRGSLT
KLKGPLTMMASHYKQHCPPTPETSCATQIITFESFKENLKDFLL
VIPFDCWEPVQE (SEQ ID NO: 2462)

1 acacagagag aaaggctaaa gttctctgga ggatgtggct gcagagcctg ctgctcttgg 61 gcactgtggc ctgcagcatc tctgcacccg cccgctcgcc cagccccagc acgcagccct 121 gggagcatgt gaatgccatc caggaggccc ggcgtctcct gaacctgagt agagacactg 181 ctgctgagat gaatgaaaca gtagaagtca tctcagaaat gtttgacctc caggagccga 241 cctgcctaca gacccgcctg gagctgtaca agcagggcct gcggggcagc ctcaccaagc 301 tcaagggccc cttgaccatg atggccagcc actacaagca gcactgccct ccaaccccgg 361 aaacttcctg tgcaacccag attatcacct ttgaaagttt caaagagaac ctgaaggact 421 ttctgcttgt catccccttt gactgctggg agccagtcca ggagtgagac cggccagatg 481 aggctggcca agccggggag ctgctctctc atgaaacaag agctagaaac tcaggatggt 541 catcttggag ggaccaaggg gtgggccaca gccatggtgg gagtggcctg gacctgccct 601 gggccacact gaccctgata caggcatggc agaagaatgg gaatatttta tactgacaga 661 aatcagtaat atttatatat ttatattttt aaaatattta tttatttatt tatttaagtt TABLE 5-continued 721 catattccat atttattcaa gatgttttac cgtaataatt attattaaaa atatgcttct 781 a (SEQ ID NO: 2463)

TNF-ALPHA TYPE II RECEPTOR
*Homo sapiens* tumor necrosis factor (TNF superfamily, member 2)
(TNF), mRNA.
ACCESSION NM_000594
VERSION NM_000594.2 GI: 25952110

MSTESMIRDVELAEEALPKKTGGPQGSRRCLFLSLFSFLIVAGATTLFCLLHFG
VIGPQREEFPRDLSLISPLAQAVRSSSRTPSDKPVAHVVANPQAEGQLQWLNR
RANALLANGVELRDNQLVVPSEGLYLIYSQVLFKGQGCPSTHVLLTHTISRIAV
SYQTKVNLLSAIKSPCQRETPEGAEAKPWYEPIYLGGVFQLEKGDRLSAEINRP
DYLDFAESGQVYFGIIAL (SEQ ID NO: 2464)

1 ctccctcagc aaggacagca gaggaccagc taagagggag agaagcaact acagaccccc 61 cctgaaaaca accctcagac gccacatccc ctgacaagct gccaggcagg ttctcttcct 121 ctcacatact gacccacggc tccaccctct ctcccctgga aaggacacca tgagcactga 181 aagcatgatc cgggacgtgg agctggccga ggaggcgctc cccaagaaga caggggggcc 241 ccagggctcc aggcggtgct tgttcctcag cctcttctcc ttcctgatcg tggcaggcgc 301 caccacgctc ttctgcctgc tgcactttgg agtgatcggc ccccagaggg aagagttccc 361 cagggacctc tctctaatca gccctctggc ccaggcagtc agatcatctt ctcgaacccc 421 gagtgacaag cctgtagccc atgttgtagc aaaccctcaa gctgaggggc agctccagtg 481 gctgaaccgc cgggccaatg ccctcctggc caatggcgtg gagctgagag ataaccagct 541 ggtggtgcca tcagagggcc tgtacctcat ctactcccag gtcctcttca agggccaagg 601 ctgcccctcc acccatgtgc tcctcaccca caccatcagc cgcatcgccg tctcctacca 661 gaccaaggtc aacctcctct ctgccatcaa gagcccctgc cagagggaga ccccagaggg 721 ggctgaggcc aagccctggt atgagcccat ctatctggga ggggtcttcc agctggagaa 781 gggtgaccga ctcagcgctg agatcaatcg gcccgactat ctcgactttg ccgagtctgg 841 gcaggtctac tttgggatca ttgccctgtg aggaggacga acatccaacc ttcccaaacg 901 cctcccctgc cccaatccct ttattacccc ctccttcaga caccctcaac ctcttctggc 961 tcaaaaagag aattgggggc ttagggtcgg aacccaagct tagaacttta agcaacaaga 1021 ccaccacttc gaaacctggg attcaggaat gtgtggcctg cacagtgaag tgctggcaac 1081 cactaagaat tcaaactggg gcctccagaa ctcactgggg cctacagctt tgatccctga 1141 catctggaat ctggagacca gggagccttt ggttctggcc agaatgctgc aggacttgag 1201 aagacctcac ctagaaattg acacaagtgg accttaggcc ttcctctctc cagatgtttc 1261 cagacttcct tgagacacgg agcccagccc tccccatgga gccagctccc tctatttatg 1321 tttgcacttg tgattattta ttatttattt attatttatt tatttacaga tgaatgtatt 1381 tatttgggag accggggtat cctgggggac ccaatgtagg agctgccttg gctcagacat 1441 gttttccgtg aaaacggagc tgaacaatag gctgttccca tgtagccccc tggcctctgt 1501 gccttctttt gattatgttt tttaaaatat ttatctgatt aagttgtcta aacaatgctg 1561 atttggtgac caactgtcac tcattgctga gcctctgctc cccaggggag ttgtgtctgt 1621 aatcgcccta ctattcagtg gcgagaaata aagtttgctt agaaaagaa (SEQ ID NO: 2465)

DEFINITION *Homo sapiens* tumor necrosis factor receptor superfamily,
member 1A
(TNFRSF1A), mRNA.
ACCESSION NM_001065
VERSION NM_001065.2 GI: 23312372

MGLSTVPDLLLPLVLLELLVGIYPSGVIGLVPHLGDREKRDSVCPQGKYIHPQN
NSICCTKCHKGTYLYNDCPGPGQDTDCRECESGSFTASENHLRHCLSCSKCRK

TABLE 5-continued

```
EMGQVEISSCTVDRDTVCGCRKNQYRHYWSENLFQCFNCSLCLNGTVHLSCQ
EKQNTVCTCHAGFFLRENECVSCSNCKKSLECTKLCLPQIENVKGTEDSGTTV
LLPLVIFFGLCLLSLLFIGLMYRYQRWKSKLYSIVCGKSTPEKEGELEGTTTKPL
APNPSFSPTPGFTPTLGFSPVPSSTFTSSSTYTPGDCPNFAAPRREVAPPYQGAD
PILATALASDPIPNPLQKWEDSAHKPQSLDTDDPATLYAVVENVPPLRWKEFV
RRLGLSDHEIDRLELQNGRCLREAQYSMLATWRRRTPRREATLELLGRVLRD
MDLLGCLEDIEEALCGPAALPPAPSLLR (SEQ ID NO: 2466)

   1 gctgttgcaa cactgcctca ctcttcccct cccaccttct ctcccctcct ctctgcttta
  61 attttctcag aattctctgg actgaggctc cagttctggc ctttggggtt caagatcact
 121 gggaccaggc cgtgatctct atgcccgagt ctcaaccctc aactgtcacc ccaaggcact
 181 tgggacgtcc tggacagacc gagtcccggg aagccccagc actgccgctg ccacactgcc
 241 ctgagcccaa atgggggagt gagaggccat agctgtctgg catgggcctc tccaccgtgc
 301 ctgacctgct gctgccactg gtgctcctgg agctgttggt gggaatatac ccctcagggg
 361 ttattggact ggtccctcac ctaggggaca gggagaagag agatagtgtg tgtccccaag
 421 gaaaatatat ccaccctcaa aataattcga tttgctgtac caagtgccac aaaggaacct
 481 acttgtacaa tgactgtcca ggcccggggc aggatacgga ctgcagggag tgtgagagcg
 541 gctccttcac cgcttcagaa aaccacctca gacactgcct cagctgctcc aaatgccgaa
 601 aggaaatggg tcaggtggag atctcttctt gcacagtgga ccgggacacc gtgtgtggct
 661 gcaggaagaa ccagtaccgg cattattgga gtgaaaacct tttccagtgc ttcaattgca
 721 gcctctgcct caatgggacc gtgcacctct cctgccagga gaaacagaac accgtgtgca
 781 cctgccatgc aggtttcttt ctaagagaaa acgagtgtgt ctcctgtagt aactgtaaga
 841 aaagcctgga gtgcacgaag ttgtgcctac cccagattga gaatgttaag ggcactgagg
 901 actcaggcac cacagtgctg ttgcccctgg tcattttctt tggtctttgc cttttatccc
 961 tcctcttcat tggtttaatg tatcgctacc aacggtggaa gtccaagctc tactccattg
1021 tttgtgggaa atcgacacct gaaaaagagg gggagcttga aggaactact actaagcccc
1081 tggccccaaa cccaagcttc agtcccactc caggcttcac ccccaccctg ggcttcagtc
1141 ccgtgcccag ttccaccttc acctccagct ccacctatac ccccggtgac tgtcccaact
1201 ttgcggctcc ccgcagagag gtggcaccac cctatcaggg ggctgacccc atccttgcga
1261 cagccctcgc ctccgacccc atccccaacc cccttcagaa gtgggaggac agcgcccaca
1321 agccacagag cctagacact gatgaccccg cgacgctgta cgccgtggtg gagaacgtgc
1381 ccccgttgcg ctggaaggaa ttcgtgcggc gcctagggct gagcgaccac gagatcgatc
1441 ggctggagct gcagaacggg cgctgcctgc gcgaggcgca atacagcatg ctggcgacct
1501 ggaggcggcg cacgccgcgg cgcgaggcca cgctggagct gctgggacgc gtgctccgcg
1561 acatggacct gctgggctgc ctggaggaca tcgaggaggc gctttgcggc cccgccgccc
1621 tcccgcccgc gcccagtctt ctcagatgag gctgcgcccc tgcgggcagc tctaaggacc
1681 gtcctgcgag atcgccttcc aaccccactt ttttctggaa aggaggggtc ctgcaggggc
1741 aagcaggagc tagcagccgc ctacttggtg ctaacccctc gatgtacata gcttttctca
1801 gctgcctgcg cgccgccgac agtcagcgct gtgcgcgcgg agagaggtgc gccgtgggct
1861 caagagcctg agtgggtggt ttgcgaggat gagggacgct atgcctcatg cccgttttgg
1921 gtgtcctcac cagcaaggct gctcgggggc ccctggttcg tccctgagcc tttttcacag
1981 tgcataagca gttttttttg tttttgtttt gttttgtttt gtttttaaat caatcatgtt
2041 acactaatag aaacttggca ctcctgtgcc ctctgcctgg acaagcacat agcaagctga
2101 actgtcctaa ggcaggggcg agcacggaac aatggggcct tcagctggag ctgtggactt
```

TABLE 5-continued 2161 ttgtacatac actaaaattc tgaagttaaa gctctgctct tggaaaaaaa aaaaaaaaaa 2221 aaaaaaaaaa aaaaaa (SEQ ID NO: 2467)

BETA INTERFERON
*Homo sapiens* interferon, beta 1, fibroblast (IFNB1), mRNA.
ACCESSION NM_002176
VERSION NM_002176.2 GI: 50593016

MTNKCLLQIALLLCFSTTALSMSYNLLGFLQRSSNFQCQKLLWQLNGRLEYCL
KDRMNFDIPEEIKQLQQFQKEDAALTIYEMLQNIFAIFRQDSSSTGWNETIVEN
LLANVYHQINHLKTVLEEKLEKEDFTRGKLMSSLHLKRYYGRILHYLKAKEY
SHCAWTIVRVEILRNFYFINRLTGYLRN (SEQ ID NO: 2468)

1 acattctaac tgcaaccttt cgaagccttt gctctggcac aacaggtagt aggcgacact 61 gttcgtgttg tcaacatgac caacaagtgt ctcctccaaa ttgctctcct gttgtgcttc 121 tccactacag ctctttccat gagctacaac ttgcttggat tcctacaaag aagcagcaat 181 tttcagtgtc agaagctcct gtggcaattg aatgggaggc ttgaatactg cctcaaggac 241 aggatgaact ttgacatccc tgaggagatt aagcagctgc agcagttcca gaaggaggac 301 gccgcattga ccatctatga gatgctccag aacatctttg ctattttcag acaagattca 361 tctagcactg gctggaatga gactattgtt gagaacctcc tggctaatgt ctatcatcag 421 ataaaccatc tgaagacagt cctggaagaa aaactggaga aagaagattt caccagggga

481 aaactcatga gcagtctgca cctgaaaaga tattatggga ggattctgca ttacctgaag 541 gccaaggagt acagtcactg tgcctggacc atagtcagag tggaaatcct aaggaacttt 601 tacttcatta acagacttac aggttacctc cgaaactgaa gatctcctag cctgtgcctc 661 tgggactgga caattgcttc aagcattctt caaccagcag atgctgttta agtgactgat 721 ggctaatgta ctgcatatga aaggacacta gaagattttg aaatttttat taaattatga 781 gttattttta tttatttaaa ttttattttg gaaaataaat tatttttggt gcaaaagtca (SEQ ID NO: 2469)

GAMMA INTERFERON
*Homo sapiens* interferon, gamma (IFNG), mRNA.
ACCESSION NM_000619
VERSION NM_000619.2 GI: 56786137

MKYTSYILAFQLCIVLGSLGCYCQDPYVKEAENLKKYFNAGHSDVADNGTLF
LGILKNWKEESDRKIMQSQIVSFYFKLFKNFKDDQSIQKSVETIKEDMNVKFFN
SNKKKRDDFEKLTNYSVTDLNVQRKAIHELIQVMAELSPAAKTGKRKRSQML
FRGRRASQ (SEQ ID NO: 2470)

1 cacattgttc tgatcatctg aagatcagct attagaagag aaagatcagt taagtccttt 61 ggacctgatc agcttgatac aagaactact gatttcaact tctttggctt aattctctcg 121 gaaacgatga aatatacaag ttatatcttg gcttttcagc tctgcatcgt tttgggttct 181 cttggctgtt actgccagga cccatatgta aaagaagcag aaaaccttaa gaaatatttt 241 aatgcaggtc attcagatgt agcggataat ggaactcttt tcttaggcat tttgaagaat 301 tggaaagagg agagtgacag aaaaataatg cagagccaaa ttgtctcctt ttacttcaaa 361 ctttttaaaa actttaaaga tgaccagagc atccaaaaga gtgtggagac catcaaggaa 421 gacatgaatg tcaagttttt caatagcaac aaaaagaaac gagatgactt cgaaaagctg 481 actaattatt cggtaactga cttgaatgtc caacgcaaag caatacatga actcatccaa 541 gtgatggctg aactgtcgcc agcagctaaa acagggaagc gaaaaaggag tcagatgctg 601 tttcgaggtc gaagagcatc ccagtaatgg ttgtcctgcc tgcaatattt gaattttaaa 661 tctaaatcta tttattaata tttaacatta tttatatggg gaatatattt ttagactcat 721 caatcaaata agtatttata atagcaactt ttgtgtaatg aaaatgaata tctattaata 781 tatgtattat ttataattcc tatatcctgt gactgtctca cttaatcctt tgttttctga TABLE 5-continued 841 ctaattaggc aaggctatgt gattacaagg ctttatctca ggggccaact aggcagccaa 901 cctaagcaag atcccatggg ttgtgtgttt atttcacttg atgatacaat gaacacttat 961 aagtgaagtg atactatcca gttactgccg gtttgaaaat atgcctgcaa tctgagccag 1021 tgctttaatg gcatgtcaga cagaacttga atgtgtcagg tgaccctgat gaaaacatag 1081 catctcagga gatttcatgc ctggtgcttc caaatattgt tgacaactgt gactgtaccc 1141 aaatggaaag taactcattt gttaaaatta tcaatatcta atatatatga ataaagtgta 1201 agttcacaac aaaaaaaaaa aaaaaaaaaa aaaaaaaaaa (SEQ ID NO: 2471)

HUMAN GROWTH HORMONE
Human growth hormone (somatotropin, GH1) gene, complete cds.
ACCESSION J00148 K00612
VERSION J00148.1 GI: 183145

MATGSRTSLLLAFGLLCLPWLQEGSAFPTIPLSRLFDNASLRAHRLHQLAFDTY
QEFNPQTSLCFSESIPTPSNREETQQKSNLELLRISLLLIQSWLEPVQFLRSVFAN
SLVYGASDSNVYDLLKDLEEGIQTLMGRLEDGSPRTGQIFKQTYSKFDTNSHN
DDALLKNYGLLYCFRKDMDKVETFLRIVQCRSVEGSCGF (SEQ ID NO: 2472)

1 agggcaccca cgtgaccctt aaagagagga caagttgggt ggtattttct ggctgacact 61 ctgtgcacaa ccctcacaac actggttgac ggtgggaagg gaaagatgac aagccagggg 121 catgatccca gcatgtgtgg gaggagcttc taaattatcc attagcacaa gcccgtcagt 181 ggccccatgc ataaatgtac acagaaacag gtgggggcaa cagtgggaga gaaggggcca 241 gggtataaaa agggcccaca agagaccggc tcaaggatcc caaggcccaa ctccccgaac 301 cactcagggt cctgtggacg ctcacctagc tgcaatggct acaggtaagc gcccctaaaa 361 tccctttggg cacaatgtgt cctgagggga gaggcagcga cctgtagatg ggacgggggc 421 actaaccctc aggtttgggg cttctgaatg agtatcgcca tgtaagccca gtatggccaa 481 tctcagaaag ctcctggtcc ctggagggat ggagagagaa aaacaaacag ctcctggagc 541 agggagagtg ctggcctctt gctctccggc tccctctgtt gccctctggt ttctccccag 601 gctcccggac gtccctgctc ctggcttttg gcctgctctg cctgccctgg cttcaagagg 661 gcagtgcctt cccaaccatt cccttatcca ggctttttga caacgctagt ctccgcgccc 721 atcgtctgca ccagctggcc tttgacacct accaggagtt tgtaagctct tggggaatgg 781 gtgcgcatca ggggtggcag gaaggggtga ctttcccccg ctgggaaata agaggaggag 841 actaaggagc tcagggtttt tcccgaagcg aaaatgcagg cagatgagca cacgctgagt 901 gaggttccca gaaaagtaac aatgggagct ggtctccagc gtagaccttg gtgggcggtc 961 cttctcctag gaagaagcct atatcccaaa ggaacagaag tattcattcc tgcagaaccc 1021 ccagacctcc ctctgtttct cagagtctat tccgacaccc tccaacaggg aggaaacaca 1081 acagaaatcc gtgagtggat gccttgaccc caggcgggga tgggggagac ctgtagtcag 1141 agcccccggg cagcacaggc caatgcccgt ccttcccctg cagaacctag agctgctccg 1201 catctccctg ctgctcatcc agtcgtggct ggagcccgtg cagttcctca ggagtgtctt 1261 cgccaacagc ctggtgtacg gcgcctctga cagcaacgtc tatgacctcc taaaggacct 1321 agaggaaggc atccaaacgc tgatgggggt gggggtggcg ctaggggtcc ccaatcttgg 1381 agccccactg actttgagag ctgtgttaga gaaacactgc tgccctcttt ttagcagtcc 1441 aggccctgac ccaagagaac tcaccttatt cttcatttcc cctcgtgaat cctctagcct 1501 ttctctacac cctgaagggg agggaggaaa atgaatgaat gagaaaggga gggagcagta 1561 cccaagcgct tggcctctcc ttctcttcct tcactttgca gaggctggaa gatggcagcc 1621 cccggactgg gcagatcttc aagcagacct acagcaagtt cgacacaaac tcacacaacg TABLE 5-continued 1681 atgacgcact actcaagaac tacgggctgc tctactgctt caggaaggac atggacaagg 1741 tcgagacatt cctgcgcatc gtgcagtgcc gctctgtgga gggcagctgt ggcttctagc 1801 tgcccgggtg gcatccctgt gacccctccc cagtgcctct cctggccttg gaagttgcca 1861 ctccagtgcc caccagcctt gtcctaataa aattaagttg catcattttg tctgactagg 1921 tgtcctctat aatattatgg ggtggagggg ggtggtttgg agca (SEQ ID NO: 2473)

COAGULATION FACTORS
*Homo sapiens* coagulation factor VII (serum prothrombin conversion accelerator) (F7), transcript variant 2, mRNA.
ACCESSION NM_019616
VERSION NM_019616.1 GI: 10518502

MVSQALRLLCLLLGLQGCLAAVFVTQEEAHGVLHRRRRANAFLEELRPGSLE
RECKEEQCSFEEAREIFKDAERTKLFWISYSDGDQCASSPCQNGGSCKDQLQS
YICFCLPAFEGRNCETHKDDQLICVNENGGCEQYCSDHTGTKRSCRCHEGYSL
LADGVSCTPTVEYPCGKIPILEKRNASKPQGRIVGGKVCPKGECPWQVLLLVN
GAQLCGGTLINTIWVVSAAHCFDKIKNWRNLIAVLGEHDLSEHDGDEQSRRV
AQVIIPSTYVPGTTNHDIALLRLHQPVVLTDHVVPLCLPERTFSERTLAFVRFSL
VSGWGQLLDRGATALELMVLNVPRLMTQDCLQQSRKVGDSPNITEYMFCAG
YSDGSKDSCKGDSGGPHATHYRGTWYLTGIVSWGQGCATVGHFGVYTRVSQ
YIEWLQKLMRSEPRPGVLLRAPFP (SEQ ID NO: 2474)

1 agtcccatgg ggaatgtcaa caggcagggg cagcactgca gagatttcat catggtctcc 61 caggccctca ggctcctctg ccttctgctt gggcttcagg gctgcctggc tgcagtcttc 121 gtaacccagg aggaagccca cggcgtcctg caccggcgcc ggcgcgccaa cgcgttcctg 181 gaggagctgc ggccgggctc cctggagagg gagtgcaagg aggagcagtg ctccttcgag 241 gaggcccggg agatcttcaa ggacgcggag aggacgaagc tgttctggat ttcttacagt 301 gatggggacc agtgtgcctc aagtccatgc cagaatgggg gctcctgcaa ggaccagctc 361 cagtcctata tctgcttctg cctccctgcc ttcgagggcc ggaactgtga gacgcacaag 421 gatgaccagc tgatctgtgt gaacgagaac ggcggctgtg agcagtactg cagtgaccac 481 acgggcacca agcgctcctg tcggtgccac gaggggtact ctctgctggc agacggggtg 541 tcctgcacac ccacagttga atatccatgt ggaaaaatac ctattctaga aaaaagaaat 601 gccagcaaac cccaaggccg aattgtgggg ggcaaggtgt gccccaaagg ggagtgtcca 661 tggcaggtcc tgttgttggt gaatggagct cagttgtgtg gggggaccct gatcaacacc 721 atctgggtgg tctccgcggc ccactgtttc gacaaaatca agaactggag gaacctgatc 781 gcggtgctgg gcgagcacga cctcagcgag cacgacgggg atgagcagag ccggcgggtg 841 gcgcaggtca tcatccccag cacgtacgtc ccgggcacca ccaaccacga catcgcgctg 901 ctccgcctgc accagcccgt ggtcctcact gaccatgtgg tgcccctctg cctgcccgaa 961 cggacgttct ctgagaggac gctggccttc gtgcgcttct cattggtcag cggctggggc 1021 cagctgctgg accgtggcgc cacggccctg gagctcatgg tgctcaacgt gccccggctg 1081 atgacccagg actgcctgca gcagtcacgg aaggtgggag actccccaaa tatcacggag 1141 tacatgttct gtgccggcta ctcggatggc agcaaggact cctgcaaggg ggacagtgga 1201 ggcccacatg ccacccacta ccggggcacg tggtacctga cgggcatcgt cagctggggc 1261 cagggctgcg caaccgtggg ccactttggg gtgtacacca gggtctccca gtacatcgag 1321 tggctgcaaa agctcatgcg ctcagagcca cgcccaggag tcctcctgcg agccccattt 1381 ccctagccca gcagccctgg cctgtggaga gaaagccaag gctgcgtcga actgtcctgg 1441 caccaaatcc catatattct tctgcagtta atggggtaga ggagggcatg ggagggaggg 1501 agaggtgggg agggagacag agacagaaac agagagagac agagacagag agagactgag 1561 ggagagactc tgaggacatg gagagagact caaagagact ccaagattca aagagactaa TABLE 5-continued 1621 tagagacaca gagatggaat agaaaagatg agaggcagag gcagacaggc gctggacaga 1681 ggggcagggg agtgccaagg ttgtcctgga ggcagacagc ccagctgagc ctccttacct 1741 cccttcagcc aagccccacc tgcacgtgat ctgctggccc tcaggctgct gctctgcctt 1801 cattgctgga gacagtagag gcatgaacac acatggatgc acacacacac acgccaatgc 1861 acacacacag agatatgcac acacacggat gcacacacag atggtcacac agagatacgc 1921 aaacacaccg atgcacacgc acatagagat atgcacacac agatgcacac acagatatac 1981 acatggatgc acgcacatgc caatgcacgc acacatcagt gcacacggat gcacagagat 2041 atgcacacac cgatgtgcgc acacacagat atgcacacac atggatgagc acacacacac 2101 caagtgcgca cacacaccga tgtacacaca cagatgcaca cacagatgca cacacaccga 2161 tgctgactcc atgtgtgctg tcctctgaag gcggttgttt agctctcact tttctggttc 2221 ttatccatta tcatcttcac ttcagacaat tcagaagcat caccatgcat ggtggcgaat 2281 gcccccaaac tctcccccaa atgtatttct cccttcgctg ggtgccgggc tgcacagact 2341 attccccacc tgcttcccag cttcacaata aacggctgcg tctcctccgc acacctgtgg 2401 tgcctgccac cc (SEQ ID NO: 2475)

*Homo sapiens* coagulation factor V (proaccelerin, labile factor)
(F5), mRNA.
ACCESSION NM_000130
VERSION NM_000130.2 GI: 10518500

MFPGCPRLWVLVVLGTSWVGWGSQGTEAAQLRQFYVAAQGISWSYRPEPTN
SSLNLSVTSFKKIVYREYEPYFKKEKPQSTISGLLGPTLYAEVGDIIKVHFKNKA
DKPLSIHPQGIRYSKLSEGASYLDHTFPAEKMDDAVAPGREYTYEWSISEDSG
PTHDDPPCLTHIYYSHENLIEDFNSGLIGPLLICKKGTLTEGGTQKTFDKQIVLL
FAVFDESKSWSQSSSLMYTVNGYVNGTMPDITVCAHDHISWHLLGMSSGPEL
FSIHFNGQVLEQNHHKVSAITLVSATSTTANMTVGPEGKWIISSLTPKHLQAG
MQAYIDIKNCPKKTRNLKKITREQRRHMKRWEYFIAAEEVIWDYAPVIPANM
DKKYRSQHLDNFSNQIGKHYKKVMYTQYEDESFTKHTVNPNMKEDGILGPII
RAQVRDTLKIVFKNMASRPYSIYPHGVTFSPYEDEVNSSFTSGRNNTMIRAVQ
PGETYTYKWNILEFDEPTENDAQCLTRPYYSDVDIMRDIASGLIGLLLICKSRSL
DRRGIQRAADIEQQAVFAVFDENKSWYLEDNINKFCENPDEVKRDDPKFYES
NIMSTINGYVPESITTLGFCFDDTVQWHFCSVGTQNEILTIHFTGHSFIYGKRHE
DTLTLFPMRGESVTVTMDNVGTWMLTSMNSSPRSKKLRLKFRDVKCIPDDDE
DSYEIFEPPESTVMATRKMHDRLEPEDEESDADYDYQNRLAAALGIRSFRNSS
LNQEEEEFNLTALALENGTEFVSSNTDIIVGSNYSSPSNISKFTVNNLAEPQKAP
SHQQATTAGSPLRHLIGKNSVLNSSTAEHSSPYSEDPIEDPLQPDVTGIRLLSLG
AGEFRSQEHAKRKGPKVERDQAAKHRFSWMKLLAHKVGRHLSQDTGSPSG
MRPWEDLPSQDTGSPSRMRPWEDPPSDLLLLKQSNSSKILVGRWHLASEKGS
YEIIQDTDEDTAVNNWLISPQNASRAWGESTPLANKPGKQSGHPKFPRVRHKS
LQVRQDGGKSRLKKSQFLIKTRKKKKEKHTHHAPLSPRTFHPLRSEAYNTFSE
RRLKHSLVLHKSNETSLPTDLNQTLPSMDFGWIASLPDHNQNSSNDTGQASCP
PGLYQTVPPEEHYQTFPIQDPDQMHSTSDPSHRSSSPELSEMLEYDRSHKSFPT
DISQMSPSSEHEVWQTVISPDLSQVTLSPELSQTNLSPDLSHTTLSPELIQRNLSP
ALGQMPISPDLSHTTLSPDLSHTTLSLDLSQTNLSPELSQTNLSPALGQMPLSPD
LSHTTISLDFSQTNLSPELSHMTLSPELSQTNLSPALGQMPISPDLSHTTLSLDFS
QTNLSPELSQTNLSPALGQMPLSPDPSHTTLSLDLSQTNLSPELSQTNLSPDLSE
MPLFADLSQIPLTPDLDQMTLSPDLGETDLSPNFGQMSLSPDLSQVTLSPDISDT
TLLPDLSQISPPPDLDQIFYPSESSQSLLLQEFNESFPYPDLGQMPSPSSPTLNDT
FLSKEFNPLVIVGLSKDGTDYIEIIPKEEVQSSEDDYAEIDYVPYDDPYKTDVRT
NINSSRDPDNIAAWYLRSNNGNRRNYYIAAEEISWDYSEFVQRETDIEDSDDIP
EDTTYKKVVFRKYLDSTFTKRDPRGEYEEHLGILGPIIRAEVDDVIQVRFKNLA
SRPYSLHAHGLSYEKSSEGKTYEDDSPEWFKEDNAVQPNSSYTYVWHATERS
GPESPGSACRAWAYYSAVNPEKDIHSGLIGPLLICQKGILHKDSNMPVDMREF
VLLFMTFDEKKSWYYEKKSRSSWRLTSSEMKKSHEFHAINGMIYSLPGLKMY
EQEWVRLHLLNIGGSQDIHVVHFHGQTLLENGNKQHQLGVWPLLPGSFKTLE
MKASKPGWWLLNTEVGENQRAGMQTPFLIMDRDCRMPMGLSTGIISDSQIKA
SEFLGYWEPRLARLNNGGSYNAWSVEKLAAEFASKPWIQVDMQKEVIITGIQ
TQGAKHYLKSCYTTEFYVAYSSNQINWQIFKGNSTRNVMYFNGNSDASTIKE
NQFDPPIVARYIRISPTRAYNRPTLRLELQGCEVNGCSTPLGMENGKIENKQIT
ASSFKKSWWGDYWEPFRARLNAQGRVNAWQAKANNNKQWLEIDLLKIKKI
TAIITQGCKSLSSEMYVKSYTIHYSEQGVEWKPYRLKSSMVDKIFEGNTNTKG
HVKNFFNPPIISRFIRVIPKTWNQSIALRLELFGCDIY" (SEQ ID NO: 2476)

1 tcattgcagc tgggacagcc cggagtgtgg ttagcagctc ggcaagcgct gcccaggtcc 61 tggggtggtg gcagccagcg ggagcaggaa aggaagcatg ttcccaggct gcccacgcct TABLE 5-continued 121 ctgggtcctg gtggtcttgg gcaccagctg ggtaggctgg gggagccaag ggacagaagc 181 ggcacagcta aggcagttct acgtggctgc tcagggcatc agttggagct accgacctga 241 gcccacaaac tcaagtttga atctttctgt aacttccttt aagaaaattg tctacagaga 301 gtatgaacca tattttaaga aagaaaaacc acaatctacc atttcaggac ttcttgggcc 361 tactttatat gctgaagtcg gagacatcat aaaagttcac tttaaaaata aggcagataa 421 gcccttgagc atccatcctc aaggaattag gtacagtaaa ttatcagaag gtgcttctta 481 ccttgaccac acattccctg cagagaagat ggacgacgct gtggctccag gccgagaata 541 cacctatgaa tggagtatca gtgaggacag tggacccacc catgatgacc ctccatgcct 601 cacacacatc tattactccc atgaaaatct gatcgaggat ttcaactctg ggctgattgg 661 gcccctgctt atctgtaaaa aagggaccct aactgagggt gggacacaga agacgtttga 721 caagcaaatc gtgctactat ttgctgtgtt tgatgaaagc aagagctgga gccagtcatc 781 atccctaatg tacacagtca atggatatgt gaatgggaca atgccagata taacagtttg 841 tgcccatgac cacatcagct ggcatctgct gggaatgagc tcggggccag aattattctc 901 cattcatttc aacggccagg tcctggagca gaaccatcat aaggtctcag ccatcaccct 961 tgtcagtgct acatccacta ccgcaaatat gactgtgggc ccagagggaa agtggatcat 1021 atcttctctc accccaaaac atttgcaagc tgggatgcag gcttacattg acattaaaaa 1081 ctgcccaaag aaaaccagga atcttaagaa aataactcgt gagcagaggc ggcacatgaa 1141 gaggtgggaa tacttcattg ctgcagagga agtcatttgg gactatgcac ctgtaatacc 1201 agcgaatatg gacaaaaaat acaggtctca gcatttggat aatttctcaa accaaattgg 1261 aaaacattat aagaaagtta tgtacacaca gtacgaagat gagtccttca ccaaacatac 1321 agtgaatccc aatatgaaag aagatgggat tttgggtcct attatcagag cccaggtcag 1381 agacacactc aaaatcgtgt tcaaaaatat ggccagccgc ccctatagca tttaccctca 1441 tggagtgacc ttctcgcctt atgaagatga agtcaactct tctttcacct caggcaggaa 1501 caacaccatg atcagagcag ttcaaccagg ggaaacctat acttataagt ggaacatctt 1561 agagtttgat gaacccacag aaaatgatgc ccagtgctta acaagaccat actacagtga 1621 cgtggacatc atgagagaca tcgcctctgg gctaatagga ctacttctaa tctgtaagag 1681 cagatccctg gacaggcgag gaatacagag ggcagcagac atcgaacagc aggctgtgtt 1741 tgctgtgttt gatgagaaca aaagctggta ccttgaggac aacatcaaca agttttgtga 1801 aaatcctgat gaggtgaaac gtgatgaccc caagttttat gaatcaaaca tcatgagcac 1861 tatcaatggc tatgtgcctg agagcataac tactcttgga ttctgctttg atgacactgt 1921 ccagtggcac ttctgtagtg tggggaccca gaatgaaatt ttgaccatcc acttcactgg 1981 gcactcattc atctatggaa agaggcatga ggacaccttg accctcttcc ccatgcgtgg 2041 agaatctgtg acggtcacaa tggataatgt tggaacttgg atgttaactt ccatgaattc 2101 tagtccaaga agcaaaaagc tgaggctgaa attcagggat gttaaatgta tcccagatga 2161 tgatgaagac tcatatgaga tttttgaacc tccagaatct acagtcatgg ctacacggaa 2221 aatgcatgat cgtttagaac ctgaagatga agagagtgat gctgactatg attaccagaa 2281 cagactggct gcagcattag gaattaggtc attccgaaac tcatcattga accaggaaga 2341 agaagagttc aatcttactg ccctagctct ggagaatggc actgaattcg tttcttcgaa 2401 cacagatata attgttggtt caaattattc ttccccaagt aatattagta agttcactgt 2461 caataacctt gcagaacctc agaaagcccc ttctcaccaa caagccacca cagctggttc TABLE 5-continued 2521 cccactgaga cacctcattg gcaagaactc agttctcaat tcttccacag cagagcattc 2581 cagcccatat tctgaagacc ctatagagga tcctctacag ccagatgtca cagggatacg 2641 tctactttca cttggtgctg gagaattcag aagtcaagaa catgctaagc gtaagggacc 2701 caaggtagaa agagatcaag cagcaaagca caggttctcc tggatgaaat tactagcaca 2761 taaagttggg agacacctaa gccaagacac tggttctcct tccggaatga ggccctggga 2821 ggaccttcct agccaagaca ctggttctcc ttccagaatg aggccctggg aggaccctcc 2881 tagtgatctg ttactcttaa aacaaagtaa ctcatctaag attttggttg ggagatggca 2941 tttggcttct gagaaaggta gctatgaaat aatccaagat actgatgaag acacagctgt 3001 taacaattgg ctgatcagcc cccagaatgc ctcacgtgct tggggagaaa gcacccctct 3061 tgccaacaag cctggaaagc agagtggcca cccaaagttt cctagagtta gacataaatc 3121 tctacaagta agacaggatg gaggaaagag tagactgaag aaaagccagt ttctcattaa 3181 gacacgaaaa aagaaaaaag agaagcacac acaccatgct cctttatctc cgaggacctt 3241 tcaccctcta agaagtgaag cctacaacac attttcagaa agaagactta agcattcgtt 3301 ggtgcttcat aaatccaatg aaacatctct tcccacagac ctcaatcaga cattgccctc 3361 tatggatttt ggctggatag cctcacttcc tgaccataat cagaattcct caaatgacac 3421 tggtcaggca agctgtcctc caggtcttta tcagacagtg cccccagagg aacactatca 3481 aacattcccc attcaagacc ctgatcaaat gcactctact tcagacccca gtcacagatc 3541 ctcttctcca gagctcagtg aaatgcttga gtatgaccga agtcacaagt ccttccccac 3601 agatataagt caaatgtccc cttcctcaga acatgaagtc tggcagacag tcatctctcc 3661 agacctcagc caggtgaccc tctctccaga actcagccag acaaacctct ctccagacct 3721 cagccacacg actctctctc cagaactcat tcagagaaac ctttccccag ccctcggtca 3781 gatgcccatt tctccagacc tcagccatac aaccctttct ccagacctca gccatacaac 3841 cctttcttta gacctcagcc agacaaacct ctctccagaa ctcagtcaga caaacctttc 3901 tccagccctc ggtcagatgc cccttttctcc agacctcagc catacaacca tttctctaga 3961 cttcagccag acaaacctct ctccagaact cagccatatg actctctctc cagaactcag 4021 tcagacaaac ctttccccag ccctcggtca gatgcccatt tctccagacc tcagccatac 4081 aaccctttct ctagacttca gccagacaaa cctctctcca gaactcagtc aaacaaacct 4141 ttccccagcc ctcggtcaga tgcccctttc tccagacccc agccatacaa ccctttctct 4201 agacctcagc cagacaaacc tctctccaga actcagtcag acaaaccttt ccccagacct 4261 cagtgagatg cccctctttg cagatctcag tcaaattccc cttaccccag acctcgacca 4321 gatgacactt tctccagacc ttggtgagac agatctttcc ccaaactttg gtcagatgtc 4381 cctttcccca gacctcagcc aggtgactct ctctccagac atcagtgaca ccacccttct 4441 cccggatctc agccagatat cacctcctcc agaccttgat cagatattct acccttctga 4501 atctagtcag tcattgcttc ttcaagaatt taatgagtct tttccttatc cagaccttgg 4561 tcagatgcca tctccttcat ctcctactct caatgatact tttctatcaa aggaatttaa 4621 tccactggtt atagtgggcc tcagtaaaga tggtacagat tacattgaga tcattccaaa 4681 ggaagaggtc cagagcagtg aagatgacta tgctgaaatt gattatgtgc cctatgatga 4741 cccctacaaa actgatgtta ggacaaacat caactcctcc agagatcctg acaacattgc 4801 agcatggtac ctccgcagca acaatggaaa cagaagaaat tattacattg ctgctgaaga 4861 aatatcctgg gattattcag aatttgtaca aagggaaaca gatattgaag actctgatga TABLE 5-continued

| | |
|---|---|
| 4921 | tattccagaa gataccacat ataagaaagt agtttttcga aagtacctcg acagcacttt |
| 4981 | taccaaacgt gatcctcgag gggagtatga agagcatctc ggaattcttg gtcctattat |
| 5041 | cagagctgaa gtggatgatg ttatccaagt tcgttttaaa aatttagcat ccagaccgta |
| 5101 | ttctctacat gcccatggac tttcctatga aaaatcatca gagggaaaga cttatgaaga |
| 5161 | tgactctcct gaatggttta aggaagataa tgctgttcag ccaaatagca gttataccta |
| 5221 | cgtatggcat gccactgagc gatcagggcc agaaagtcct ggctctgcct gtcgggcttg |
| 5281 | ggcctactac tcagctgtga acccagaaaa agatattcac tcaggcttga taggtcccct |
| 5341 | cctaatctgc caaaaaggaa tactacataa ggacagcaac atgcctgtgg acatgagaga |
| 5401 | atttgtctta ctatttatga cctttgatga aaagaagagc tggtactatg aaaagaagtc |
| 5461 | ccgaagttct tggagactca catcctcaga aatgaaaaaa tcccatgagt ttcacgccat |
| 5521 | taatgggatg atctacagct tgcctggcct gaaaatgtat gagcaagagt gggtgaggtt |
| 5581 | acacctgctg aacataggcg gctcccaaga cattcacgtg gttcactttc acggccagac |
| 5641 | cttgctggaa aatggcaata aacagcacca gttaggggtc tggccccttc tgcctggttc |
| 5701 | atttaaaact cttgaaatga aggcatcaaa acctggctgg tggctcctaa acacagaggt |
| 5761 | tggagaaaac cagagagcag ggatgcaaac gccatttctt atcatggaca gagactgtag |
| 5821 | gatgccaatg ggactaagca ctggtatcat atctgattca cagatcaagg cttcagagtt |
| 5881 | tctgggttac tgggagccca gattagcaag attaaacaat ggtggatctt ataatgcttg |
| 5941 | gagtgtagaa aaacttgcag cagaatttgc ctctaaacct tggatccagg tggacatgca |
| 6001 | aaaggaagtc ataatcacag ggatccagac ccaaggtgcc aaacactacc tgaagtcctg |
| 6061 | ctataccaca gagttctatg tagcttacag ttccaaccag atcaactggc agatcttcaa |
| 6121 | agggaacagc acaaggaatg tgatgtattt taatggcaat tcagatgcct ctacaataaa |
| 6181 | agagaatcag tttgacccac ctattgtggc tagatatatt aggatctctc caactcgagc |
| 6241 | ctataacaga cctacccttc gattggaact gcaaggttgt gaggtaaatg gatgttccac |
| 6301 | acccctgggt atggaaaatg gaaagataga aaacaagcaa atcacagctt cttcgtttaa |
| 6361 | gaaatcttgg tggggagatt actgggaacc cttccgtgcc cgtctgaatg cccagggacg |
| 6421 | tgtgaatgcc tggcaagcca aggcaaacaa caataagcag tggctagaaa ttgatctact |
| 6481 | caagatcaag aagataacgg caattataac acagggctgc aagtctctgt cctctgaaat |
| 6541 | gtatgtaaag agctatacca tccactacag tgagcaggga gtggaatgga aaccatacag |
| 6601 | gctgaaatcc tccatggtgg acaagatttt tgaaggaaat actaatacca aaggacatgt |
| 6661 | gaagaacttt ttcaaccccc caatcatttc caggtttatc cgtgtcattc ctaaaacatg |
| 6721 | gaatcaaagt attgcacttc gcctggaact ctttggctgt gatatttact agaattgaac |
| 6781 | attcaaaaac ccctggaaga gactctttaa gacctcaaac catttagaat gggcaatgta |
| 6841 | ttttacgctg tgttaaatgt taacagtttt ccactatttc tctttctttt ctattagtga |
| 6901 | ataaaatttt atac (SEQ ID NO: 2477) |

*Homo sapiens* coagulation factor II (thrombin) (F2), mRNA.
ACCESSION NM_000506
VERSION NM_000506.2 GI: 5922005

MAHVRGLQLPGCLALAALCSLVHSQHVFLAPQQARSLLQRVRRANTFLEEVR
KGNLERECVEETCSYEEAFEALESSTATDVFWAKYTACETARTPRDKLAACL
EGNCAEGLGTNYRGHVNITRSGIECQLWRSRYPHKPEINSTTHPGADLQENFC
RNPDSSTTGPWCYTTDPTVRRQECSIPVCGQDQVTVAMTPRSEGSSVNLSPPL
EQCVPDRGQQYQGRLAVTTHGLPCLAWASAQAKALSKHQDFNSAVQLVENF
CRNPDGDEEGVWCYVAGKPGDFGYCDLNYCEEAVEEETGDGLDEDSDRAIE

TABLE 5-continued

GRTATSEYQTFFNPRTFGSGEADCGLRPLFEKKSLEDKTERELLESYIDGRIVE
GSDAEIGMSPWQVMLFRKSPQELLCGASLISDRWVLTAAHCLLYPPWDKNFT
ENDLLVRIGKHSRTRYERNIEKISMLEKIYIHPRYNWRENLDRDIALMKLKKPV
AFSDYIHPVCLPDRETAASLLQAGYKGRVTGWGNLKETWTANVGKGQPSVL
QVVNLPIVERPVCKDSTRIRITDNMFCAGYKPDEGKRGDACEGDSGGPFVMK
SPFNNRWYQMGIVSWGEGCDRDGKYGFYTHVFRLKKWIQKVIDQFGE" (SEQ ID NO: 2478)

1 aattcctcag tgacccagga gctgacacac tatggcgcac gtccgaggct tgcagctgcc 61 tggctgcctg gccctggctg ccctgtgtag ccttgtgcac agccagcatg tgttcctggc 121 tcctcagcaa gcacggtcgc tgctccagcg ggtccggcga gccaacacct tcttggagga 181 ggtgcgcaag ggcaacctag agcgagagtg cgtggaggag acgtgcagct acgaggaggc 241 cttcgaggct ctggagtcct ccacggctac ggatgtgttc tgggccaagt acacagcttg 301 tgagacagcg aggacgcctc gagataagct tgctgcatgt ctggaaggta actgtgctga 361 gggtctgggt acgaactacc gagggcatgt gaacatcacc cggtcaggca ttgagtgcca 421 gctatggagg agtcgctacc cacataagcc tgaaatcaac tccactaccc atcctggggc 481 cgacctacag gagaatttct gccgcaaccc cgacagcagc accacgggac cctggtgcta 541 cactacagac ccccaccgtga ggaggcagga atgcagcatc cctgtctgtg gccaggatca 601 agtcactgta gcgatgactc cacgctccga aggctccagt gtgaatctgt cacctccatt 661 ggagcagtgt gtccctgatc gggggcagca gtaccagggg cgcctggcgg tgaccacaca 721 tgggctcccc tgcctggcct gggccagcgc acaggccaag gccctgagca agcaccagga 781 cttcaactca gctgtgcagc tggtggagaa cttctgccgc aacccagacg gggatgagga 841 gggcgtgtgg tgctatgtgg ccgggaagcc tggcgacttt gggtactgcg acctcaacta 901 ttgtgaggag gccgtggagg aggagacagg agatgggctg gatgaggact cagacagggc 961 catcgaaggg cgtaccgcca ccagtgagta ccagactttc ttcaatccga ggacctttgg 1021 ctcgggagag gcagactgtg ggctgcgacc tctgttcgag aagaagtcgc tggaggacaa 1081 aaccgaaaga gagctcctgg aatcctacat cgacgggcgc attgtggagg gctcggatgc 1141 agagatcggc atgtcacctt ggcaggtgat gcttttccgg aagagtcccc aggagctgct 1201 gtgtggggcc agcctcatca gtgaccgctg ggtcctcacc gccgcccact gcctcctgta 1261 cccgccctgg gacaagaact tcaccgagaa tgaccttctg gtgcgcattg gcaagcactc 1321 ccgcacaagg tacgagcgaa acattgaaaa gatatccatg ttggaaaaga tctacatcca 1381 ccccaggtac aactggcggg agaacctgga ccgggacatt gccctgatga agctgaagaa 1441 gcctgttgcc ttcagtgact acattcaccc tgtgtgtctg cccgacaggg agacggcagc 1501 cagcttgctc caggctggat acaaggggcg ggtgacaggc tggggcaacc tgaaggagac 1561 gtggacagcc aacgttggta aggggcagcc cagtgtcctg caggtggtga acctgcccat 1621 tgtggagcgg ccggtctgca aggactccac ccggatccgc atcactgaca acatgttctg 1681 tgctggttac aagcctgatg aagggaaacg aggggatgcc tgtgaaggtg acagtggggg 1741 accctttgtc atgaagagcc cctttaacaa ccgctggtat caaatgggca tcgtctcatg 1801 gggtgaaggc tgtgaccggg atgggaaata tggcttctac acacatgtgt tccgcctgaa 1861 gaagtggata cagaaggtca ttgatcagtt tggagagtag ggccactca tattctgggc 1921 tcctggaacc aatcccgtga aagaattatt tttgtgtttc taaaactatg gttcccaata 1981 aaagtgactc tcagcgg (SEQ ID NO: 2479)

TABLE 6

```
Ala Pro Pro Arg Leu Ile Cys Asp Ser Arg Val Leu Glu Arg Tyr Leu
 1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp (SEQ ID NO: 2480)

Ala Pro Pro Arg Leu Ile Cys Asp Ser Arg Val Leu Glu Arg Tyr Leu
  1               5                  10                  15

Leu Glu Ala Lys Glu Ala Glu Asn Ile Thr Thr Gly Cys Ala Glu His
             20                  25                  30

Cys Ser Leu Asn Glu Asn Ile Thr Val Pro Asp Thr Lys Val Asn Phe
         35                  40                  45

Tyr Ala Trp Lys Arg Met Glu Val Gly Gln Gln Ala Val Glu Val Trp
     50                  55                  60

Gln Gly Leu Ala Leu Leu Ser Glu Ala Val Leu Arg Gly Gln Ala Leu
 65                  70                  75                  80

Leu Val Asn Ser Ser Gln Pro Trp Glu Pro Leu Gln Leu His Val Asp
                 85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Pro Pro Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg (SEQ ID NO: 2481)
                165
```

TABLE 7

| (SEQ ID NOS: 2482-4747, respectively, in order of appearance) |
|---|
| N(Asparagine) as major constituent Oligonucleotides of peptide motifs containing 3-7 amino acid residues with N(Asparagine) as the major constituent and T(Threonine) as the minor constituent |
| AAY-AAY-ACN, ACN-AAY-AAY, AAY-ACN-AAY, AAY-AAY-AAY-ACN, ACN-AAY-AAY-AAY, AAY-ACN-AAY-AAY, AAY-AAY-ACN-AAY, AAY-AAY-AAY-AAY-ACN, ACN-AAY-AAY-AAY-AAY, AAY-ACN-AAY-AAY-AAY, AAY-AAY-ACN-AAY-AAY, AAY-AAY-AAY-ACN-AAY, AAY-AAY-AAY-ACN-ACN, ACN-ACN-AAY-AAY-AAY, ACN-AAY-ACN-AAY-AAY, ACN-AAY-AAY-ACN-AAY, ACN-AAY-AAY-AAY-ACN, AAY-ACN-ACN-AAY-AAY, AAY-ACN-AAY-ACN-AAY, AAY-ACN-AAY-AAY-ACN, AAY-AAY-ACN-ACN-AAY, AAY-AAY-ACN-AAY-ACN, AAY-AAY-AAY-AAY-AAY-ACN, ACN-AAY-AAY-AAY-AAY-AAY, AAY-ACN-AAY-AAY-AAY-AAY, AAY-AAY-ACN-AAY-AAY-AAY, AAY-AAY-AAY-ACN-AAY-AAY, AAY-AAY-AAY-AAY-ACN-AAY, AAY-AAY-AAY-AAY-ACN-ACN, ACN-ACN-AAY-AAY-AAY-AAY, ACN-AAY-ACN-AAY-AAY-AAY, ACN-AAY-AAY-ACN-AAY-AAY, ACN-AAY-AAY-AAY-ACN-AAY, ACN-AAY-AAY-AAY-AAY-ACN, AAY-ACN-ACN-AAY-AAY-AAY, AAY-ACN-AAY-ACN-AAY-AAY, AAY-ACN-AAY-AAY-ACN-AAY, AAY-ACN-AAY-AAY-AAY-ACN, AAY-AAY-ACN-ACN-AAY-AAY, AAY-AAY-ACN-AAY-ACN-AAY, AAY-AAY-ACN-AAY-AAY-ACN, AAY-AAY-AAY-ACN-ACN-AAY, AAY-AAY-AAY-ACN-AAY-ACN, AAY-AAY-AAY-AAY-ACN-ACN-ACN, ACN-ACN-ACN-AAY-AAY-AAY-AAY, ACN-AAY-ACN-ACN-AAY-AAY-AAY, ACN-AAY-ACN-AAY-ACN-AAY-AAY, ACN-AAY-ACN-AAY-AAY-ACN-AAY, ACN-AAY-ACN-AAY-AAY-AAY-ACN, ACN-AAY-AAY-ACN-ACN-AAY-AAY, ACN-AAY-AAY-ACN-AAY-ACN-AAY, ACN-AAY-AAY-ACN-AAY-AAY-ACN, ACN-AAY-AAY-AAY-ACN-AAY-ACN, ACN-AAY-AAY-AAY-ACN-ACN-AAY, ACN-AAY-AAY-AAY-AAY-ACN-ACN, ACN-ACN-AAY-ACN-AAY-AAY-AAY, ACN-ACN-AAY-AAY-ACN-AAY-AAY, ACN-ACN-AAY-AAY-AAY-ACN-AAY, ACN-ACN-AAY-AAY-AAY-AAY-ACN, AAY-ACN-ACN-ACN-AAY-AAY-AAY, AAY-ACN-ACN-AAY-ACN-AAY-AAY, AAY-ACN-ACN-AAY-AAY-ACN-AAY, AAY-ACN-ACN-AAY-AAY-AAY-ACN, AAY-ACN-AAY-ACN-ACN-AAY-AAY, AAY-ACN-AAY-AAY-ACN-ACN-AAY, AAY-ACN-AAY-AAY-AAY-ACN-ACN, AAY-ACN-AAY-ACN-AAY-ACN-AAY, AAY-ACN-AAY-ACN-AAY-AAY-ACN, AAY-ACN-AAY-AAY-ACN-AAY-ACN, AAY-AAY-ACN-ACN-ACN-AAY-AAY, AAY-AAY-ACN-ACN-AAY-ACN-AAY, AAY-AAY-ACN-ACN-AAY-AAY-ACN, AAY-AAY-ACN-AAY-ACN-ACN-AAY, AAY-AAY-ACN-AAY-AAY-ACN-ACN, AAY-AAY-AAY-ACN-ACN-ACN-AAY, AAY-AAY-AAY-AAY-ACN-ACN-ACN, ACN-AAY-AAY-ACN-AAY-AAY-AAY, ACN-AAY-AAY-AAY-ACN-AAY-AAY, ACN-AAY-AAY-AAY-AAY-ACN-AAY, ACN-AAY-AAY-AAY-AAY-AAY-ACN, AAY-ACN-ACN-AAY-AAY-AAY-AAY, AAY-ACN-AAY-ACN-AAY-AAY-AAY, AAY-ACN-AAY-AAY-ACN-AAY-AAY, AAY-ACN-AAY-AAY-AAY-ACN-AAY, AAY-ACN-AAY-AAY-AAY-AAY-ACN, AAY-AAY-ACN-ACN-AAY-AAY-AAY, AAY-AAY-ACN-AAY-ACN-AAY-AAY, AAY-AAY-ACN-AAY-AAY-ACN-AAY, AAY-AAY-ACN-AAY-AAY-AAY-ACN, AAY-AAY-AAY-ACN-ACN-AAY-AAY, AAY-AAY-AAY-ACN-AAY-ACN-AAY, AAY-AAY-AAY-ACN-AAY-AAY-ACN, AAY-AAY-AAY-AAY-ACN-ACN-AAY, AAY-AAY-AAY-AAY-ACN-AAY-ACN-AAY-AAY-AAY-AAY-AAY-ACN, ACN-AAY-AAY-AAY-AAY-AAY-AAY, AAY-ACN-AAY-AAY-AAY-AAY-AAY, AAY-AAY-ACN-AAY-AAY-AAY-AAY, AAY-AAY-AAY-ACN-AAY-AAY-AAY, AAY-AAY-AAY-AAY-ACN-AAY-AAY, AAY-AAY-AAY-AAY-AAY-ACN-AAY |
| Oligonucleotides of peptide motifs containing 3-7 amino acid residues with N(Asparagine) as the major constituent and A(Alanine) as the minor constituent |
| AAY-AAY-GCN, GCN-AAY-AAY, AAY-GCN-AAY, AAY-AAY-AAY-GCN, GCN-AAY-AAY-AAY, AAY-GCN-AAY-AAY, AAY-AAY-GCN-AAY, AAY-AAY-AAY-AAY-GCN, GCN-AAY-AAY-AAY-AAY, AAY-GCN-AAY-AAY-AAY, AAY-AAY-GCN-AAY-AAY, AAY-AAY-AAY-GCN-AAY, AAY-AAY-AAY-GCN-GCN, GCN-GCN-AAY-AAY-AAY, GCN-AAY-GCN-AAY-AAY, GCN-AAY-AAY-GCN-AAY, GCN-AAY-AAY-AAY-GCN, AAY-GCN-GCN-AAY-AAY, AAY-GCN-AAY-GCN-AAY, AAY-GCN-AAY-AAY-GCN, AAY-AAY-GCN-GCN-AAY, AAY-AAY-GCN-AAY-GCN, AAY-AAY-AAY-AAY-AAY-GCN, GCN-AAY-AAY-AAY-AAY-AAY, AAY-GCN-AAY-AAY-AAY-AAY, AAY-AAY-GCN-AAY-AAY-AAY, AAY-AAY-AAY-GCN-AAY-AAY, AAY-AAY-AAY-AAY-GCN-AAY, AAY-AAY-AAY-AAY-GCN-GCN, GCN-GCN-AAY-AAY-AAY-AAY, GCN-AAY-GCN-AAY-AAY-AAY, GCN-AAY-AAY-GCN-AAY-AAY, GCN-AAY-AAY-AAY-GCN-AAY, GCN-AAY- |

TABLE 7-continued

| (SEQ ID NOS: 2482-4747, respectively, in order of appearance) |
|---|
| AAY-AAY-AAY-GCN, AAY-GCN-GCN-AAY-AAY-AAY, AAY-GCN-AAY-GCN-AAY-AAY, AAY-GCN-AAY-AAY-GCN-AAY, AAY-GCN-AAY-AAY-AAY-GCN, AAY-AAY-GCN-GCN-AAY-AAY, AAY-AAY-GCN-AAY-GCN-AAY, AAY-AAY-GCN-AAY-AAY-GCN, AAY-AAY-AAY-GCN-GCN-AAY, AAY-AAY-AAY-GCN-AAY-GCN, AAY-AAY-AAY-AAY-GCN-GCN-GCN, GCN-GCN-GCN-AAY-AAY-AAY-AAY, GCN-AAY-GCN-GCN-AAY-AAY-AAY, GCN-AAY-GCN-AAY-GCN-AAY-AAY, GCN-AAY-GCN-AAY-AAY-GCN-AAY, GCN-AAY-GCN-AAY-AAY-AAY-GCN, GCN-AAY-AAY-GCN-GCN-AAY-AAY, GCN-AAY-AAY-GCN-AAY-GCN-AAY, GCN-AAY-AAY-GCN-AAY-AAY-GCN, GCN-AAY-AAY-AAY-GCN-AAY-GCN, GCN-AAY-AAY-AAY-GCN-GCN-AAY, GCN-AAY-AAY-AAY-AAY-GCN-GCN, GCN-GCN-AAY-GCN-AAY-AAY-AAY, GCN-GCN-AAY-AAY-GCN-AAY-AAY, GCN-GCN-AAY-AAY-AAY-GCN-AAY, GCN-GCN-AAY-AAY-AAY-AAY-GCN, AAY-GCN-GCN-GCN-AAY-AAY-AAY, AAY-GCN-GCN-AAY-GCN-AAY-AAY, AAY-GCN-GCN-AAY-AAY-GCN-AAY, AAY-GCN-GCN-AAY-AAY-AAY-GCN, AAY-GCN-AAY-GCN-GCN-AAY-AAY, AAY-GCN-AAY-AAY-GCN-GCN-AAY, AAY-GCN-AAY-AAY-AAY-GCN-GCN, AAY-GCN-AAY-GCN-AAY-GCN-AAY, AAY-GCN-AAY-GCN-AAY-AAY-GCN, AAY-GCN-AAY-AAY-GCN-AAY-GCN, AAY-AAY-GCN-GCN-GCN-AAY-AAY, AAY-AAY-GCN-GCN-AAY-GCN-AAY, AAY-AAY-GCN-GCN-AAY-AAY-GCN, AAY-AAY-GCN-AAY-GCN-GCN-AAY, AAY-AAY-GCN-AAY-GCN-AAY-GCN, AAY-AAY-GCN-AAY-AAY-GCN-GCN, AAY-AAY-AAY-GCN-GCN-GCN-AAY, AAY-AAY-AAY-GCN-GCN-AAY-GCN, AAY-AAY-AAY-GCN-AAY-GCN-GCN, AAY-AAY-AAY-AAY-AAY-GCN-GCN, GCN-GCN-AAY-AAY-AAY-AAY-AAY, GCN-AAY-GCN-AAY-AAY-AAY-AAY, GCN-AAY-AAY-GCN-AAY-AAY-AAY, GCN-AAY-AAY-AAY-GCN-AAY-AAY, GCN-AAY-AAY-AAY-AAY-GCN-AAY, GCN-AAY-AAY-AAY-AAY-AAY-GCN, AAY-GCN-GCN-AAY-AAY-AAY-AAY, AAY-GCN-AAY-GCN-AAY-AAY-AAY, AAY-GCN-AAY-AAY-GCN-AAY-AAY, AAY-GCN-AAY-AAY-AAY-GCN-AAY, AAY-GCN-AAY-AAY-AAY-AAY-GCN, AAY-AAY-GCN-GCN-AAY-AAY-AAY, AAY-AAY-GCN-AAY-GCN-AAY-AAY, AAY-AAY-GCN-AAY-AAY-GCN-AAY, AAY-AAY-GCN-AAY-AAY-AAY-GCN, AAY-AAY-AAY-GCN-GCN-AAY-AAY, AAY-AAY-AAY-GCN-AAY-GCN-AAY, AAY-AAY-AAY-GCN-AAY-AAY-GCN, AAY-AAY-AAY-AAY-GCN-GCN-AAY, AAY-AAY-AAY-AAY-GCN-AAY-GCN-AAY-AAY-AAY-AAY-AAY-AAY-GCN, GCN-AAY-AAY-AAY-AAY-AAY-AAY, AAY-GCN-AAY-AAY-AAY-AAY-AAY, AAY-AAY-GCN-AAY-AAY-AAY-AAY, AAY-AAY-AAY-GCN-AAY-AAY-AAY, AAY-AAY-AAY-AAY-GCN-AAY-AAY, AAY-AAY-AAY-AAY-AAY-GCN-AAY |
| Oligonucleotides of peptide motifs containing 3-7 amino acid residues with N(Asparagine) as the major constituent and S(Serine) as the minor constituent |
| AAY-AAY-AGY, AGY-AAY-AAY, AAY-AGY-AAY, AAY-AAY-AAY-AGY, AGY-AAY-AAY-AAY, AAY-AGY-AAY-AAY, AAY-AAY-AGY-AAY, AAY-AAY-AAY-AAY-AGY, AGY-AAY-AAY-AAY-AAY, AAY-AGY-AAY-AAY-AAY, AAY-AAY-AGY-AAY-AAY, AAY-AAY-AAY-AGY-AAY, AAY-AAY-AAY-AGY-AGY, AGY-AGY-AAY-AAY-AAY, AGY-AAY-AGY-AAY-AAY, AGY-AAY-AAY-AGY-AAY, AGY-AAY-AAY-AAY-AGY, AAY-AGY-AGY-AAY-AAY, AAY-AGY-AAY-AGY-AAY, AAY-AGY-AAY-AAY-AGY, AAY-AAY-AGY-AGY-AAY, AAY-AAY-AGY-AAY-AGY, AAY-AAY-AAY-AAY-AAY-AGY, AGY-AAY-AAY-AAY-AAY-AAY, AAY-AGY-AAY-AAY-AAY-AAY, AAY-AAY-AGY-AAY-AAY-AAY, AAY-AAY-AAY-AGY-AAY-AAY, AAY-AAY-AAY-AAY-AGY-AAY, AAY-AAY-AAY-AAY-AGY-AGY, AGY-AGY-AAY-AAY-AAY-AAY, AGY-AAY-AGY-AAY-AAY-AAY, AGY-AAY-AAY-AGY-AAY-AAY, AGY-AAY-AAY-AAY-AGY-AAY, AGY-AAY-AAY-AAY-AAY-AGY, AAY-AGY-AGY-AAY-AAY-AAY, AAY-AGY-AAY-AGY-AAY-AAY, AAY-AGY-AAY-AAY-AGY-AAY, AAY-AGY-AAY-AAY-AAY-AGY, AAY-AAY-AGY-AGY-AAY-AAY, AAY-AAY-AGY-AAY-AGY-AAY, AAY-AAY-AGY-AAY-AAY-AGY, AAY-AAY-AAY-AGY-AGY-AAY, AAY-AAY-AAY-AGY-AAY-AGY, AAY-AAY-AAY-AAY-AGY-AGY-AGY, AGY-AGY-AGY-AAY-AAY-AAY-AAY, AGY-AAY-AGY-AGY-AAY-AAY-AAY, AGY-AAY-AGY-AAY-AGY-AAY-AAY, AGY-AAY-AGY-AAY-AAY-AGY-AAY, AGY-AAY-AGY-AAY-AAY-AAY-AGY, AGY-AAY-AAY-AGY-AGY-AAY-AAY, AGY-AAY-AAY-AGY-AAY-AGY-AAY, AGY-AAY-AAY-AGY-AAY-AAY-AGY, AGY-AAY-AAY-AAY-AGY-AAY-AGY, AGY-AAY-AAY-AAY-AGY-AGY-AAY, AGY-AAY-AAY-AAY-AAY-AGY-AGY, AGY-AGY-AAY-AGY-AAY-AAY-AAY, AGY-AGY-AAY-AAY-AGY-AAY-AAY, AGY-AGY-AAY-AAY-AAY-AGY-AAY, AGY-AGY-AAY-AAY-AAY-AAY-AGY, AAY-AGY-AGY-AGY-AAY-AAY-AAY, AAY-AGY-AGY-AAY-AGY-AAY-AAY, AAY-AGY-AGY-AAY-AAY-AGY-AAY, AAY-AGY-AGY-AAY-AAY-AAY-AGY, AAY-AGY-AAY-AGY-AGY-AAY-AAY, AAY-AGY-AAY-AAY-AGY-AGY-AAY, AAY-AGY-AAY-AAY- |

TABLE 7-continued (SEQ ID NOS: 2482-4747, respectively, in order of appearance)

AAY-AGY-AGY, AAY-AGY-AAY-AGY-AAY-AGY-AAY, AAY-AGY-AAY-AGY-AAY-AAY-AGY, AAY-AGY-AAY-AAY-AGY-AAY-AGY, AAY-AAY-AGY-AGY-AGY-AAY-AAY, AAY-AAY-AGY-AGY-AAY-AGY-AAY, AAY-AAY-AGY-AGY-AAY-AAY-AGY, AAY-AAY-AGY-AAY-AGY-AGY-AAY, AAY-AAY-AGY-AAY-AGY-AAY-AGY, AAY-AAY-AGY-AAY-AAY-AGY-AGY, AAY-AAY-AAY-AGY-AGY-AGY-AAY, AAY-AAY-AAY-AGY-AGY-AAY-AGY, AAY-AAY-AAY-AGY-AAY-AGY-AGY, AAY-AAY-AAY-AAY-AAY-AGY-AGY, AGY-AGY-AAY-AAY-AAY-AAY-AAY, AGY-AAY-AGY-AAY-AAY-AAY-AAY, AGY-AAY-AAY-AGY-AAY-AAY-AAY, AGY-AAY-AAY-AAY-AGY-AAY-AAY, AGY-AAY-AAY-AAY-AAY-AGY-AAY, AGY-AAY-AAY-AAY-AAY-AAY-AGY, AAY-AGY-AGY-AAY-AAY-AAY-AAY, AAY-AGY-AAY-AGY-AAY-AAY-AAY, AAY-AGY-AAY-AAY-AGY-AAY-AAY, AAY-AGY-AAY-AAY-AAY-AGY-AAY, AAY-AGY-AAY-AAY-AAY-AAY-AGY, AAY-AAY-AGY-AGY-AAY-AAY-AAY, AAY-AAY-AGY-AAY-AGY-AAY-AAY, AAY-AAY-AGY-AAY-AAY-AGY-AAY, AAY-AAY-AGY-AAY-AAY-AAY-AGY, AAY-AAY-AAY-AGY-AGY-AAY-AAY, AAY-AAY-AAY-AGY-AAY-AGY-AAY, AAY-AAY-AAY-AGY-AAY-AAY-AGY, AAY-AAY-AAY-AAY-AGY-AGY-AAY, AAY-AAY-AAY-AAY-AGY-AAY-AGY-AAY-AAY-AAY-AAY-AAY-AAY-AGY,

AGY-AAY-AAY-AAY-AAY-AAY-AAY, AAY-AGY-AAY-AAY-AAY-AAY-AAY, AAY-AAY-AGY-AAY-AAY-AAY-AAY, AAY-AAY-AAY-AGY-AAY-AAY-AAY, AAY-AAY-AAY-AAY-AGY-AAY-AAY, AAY-AAY-AAY-AAY-AAY-AGY-AAY

Oligonucleotides of peptide motifs containing 3-7 amino acid residues with N(Asparagine) as the major constituent and Q(Glutamine) as the minor constituent AAY-AAY-CAR, CAR-AAY-AAY, AAY-CAR-AAY, AAY-AAY-AAY-CAR, CAR-AAY-AAY-AAY, AAY-CAR-AAY-AAY, AAY-AAY-CAR-AAY, AAY-AAY-AAY-AAY-CAR, CAR-AAY-AAY-AAY-AAY, AAY-CAR-AAY-AAY-AAY, AAY-AAY-CAR-AAY-AAY, AAY-AAY-AAY-CAR-AAY, AAY-AAY-AAY-CAR-CAR, CAR-CAR-AAY-AAY-AAY, CAR-AAY-CAR-AAY-AAY, CAR-AAY-AAY-CAR-AAY, CAR-AAY-AAY-AAY-CAR, AAY-CAR-CAR-AAY-AAY, AAY-CAR-AAY-CAR-AAY, AAY-CAR-AAY-AAY-CAR, AAY-AAY-CAR-CAR-AAY, AAY-AAY-CAR-AAY-CAR, AAY-AAY-AAY-AAY-AAY-CAR, CAR-AAY-AAY-AAY-AAY-AAY, AAY-CAR-AAY-AAY-AAY-AAY, AAY-AAY-CAR-AAY-AAY-AAY, AAY-AAY-AAY-CAR-AAY-AAY, AAY-AAY-AAY-AAY-CAR-AAY, AAY-AAY-AAY-AAY-CAR-CAR, CAR-CAR-AAY-AAY-AAY-AAY, CAR-AAY-CAR-AAY-AAY-AAY, CAR-AAY-AAY-CAR-AAY-AAY, CAR-AAY-AAY-AAY-CAR-AAY, CAR-AAY-AAY-AAY-AAY-CAR, AAY-CAR-CAR-AAY-AAY-AAY, AAY-CAR-AAY-CAR-AAY-AAY, AAY-CAR-AAY-AAY-CAR-AAY, AAY-CAR-AAY-AAY-AAY-CAR, AAY-AAY-CAR-CAR-AAY-AAY, AAY-AAY-CAR-AAY-CAR-AAY, AAY-AAY-CAR-AAY-AAY-CAR, AAY-AAY-AAY-CAR-CAR-AAY, AAY-AAY-AAY-CAR-AAY-CAR, AAY-AAY-AAY-AAY-CAR-CAR-CAR, CAR-CAR-CAR-AAY-AAY-AAY-AAY, CAR-AAY-CAR-CAR-AAY-AAY-AAY, CAR-AAY-CAR-AAY-CAR-AAY-AAY, CAR-AAY-CAR-AAY-AAY-CAR-AAY, CAR-AAY-CAR-AAY-AAY-AAY-CAR, CAR-AAY-AAY-CAR-CAR-AAY-AAY, CAR-AAY-AAY-CAR-AAY-CAR-AAY, CAR-AAY-AAY-CAR-AAY-AAY-CAR, CAR-AAY-AAY-AAY-CAR-AAY-CAR, CAR-AAY-AAY-AAY-CAR-CAR-AAY, CAR-AAY-AAY-AAY-AAY-CAR-CAR, CAR-CAR-AAY-CAR-AAY-AAY-AAY, CAR-CAR-AAY-AAY-CAR-AAY-AAY, CAR-CAR-AAY-AAY-AAY-CAR-AAY, CAR-CAR-AAY-AAY-AAY-AAY-CAR, AAY-CAR-CAR-CAR-AAY-AAY-AAY, AAY-CAR-CAR-AAY-CAR-AAY-AAY, AAY-CAR-CAR-AAY-AAY-CAR-AAY, AAY-CAR-CAR-AAY-AAY-AAY-CAR, AAY-CAR-AAY-CAR-CAR-AAY-AAY, AAY-CAR-AAY-AAY-CAR-CAR-AAY, AAY-CAR-AAY-AAY-AAY-CAR-CAR, AAY-CAR-AAY-CAR-AAY-CAR-AAY, AAY-CAR-AAY-CAR-AAY-AAY-CAR, AAY-CAR-AAY-AAY-CAR-AAY-CAR, AAY-AAY-CAR-CAR-CAR-AAY-AAY, AAY-AAY-CAR-CAR-AAY-CAR-AAY, AAY-AAY-CAR-CAR-AAY-AAY-CAR, AAY-AAY-CAR-AAY-CAR-CAR-AAY, AAY-AAY-CAR-AAY-CAR-AAY-CAR, AAY-AAY-CAR-AAY-AAY-CAR-CAR, AAY-AAY-AAY-CAR-CAR-CAR-AAY, AAY-AAY-AAY-CAR-CAR-AAY-CAR, AAY-AAY-AAY-CAR-AAY-CAR-CAR, AAY-AAY-AAY-AAY-AAY-CAR-CAR, CAR-CAR-AAY-AAY-AAY-AAY-AAY, CAR-AAY-CAR-AAY-AAY-AAY-AAY, CAR-AAY-AAY-CAR-AAY-AAY-AAY, CAR-AAY-AAY-AAY-CAR-AAY-AAY, CAR-AAY-AAY-AAY-AAY-CAR-AAY, CAR-AAY-AAY-AAY-AAY-AAY-CAR, AAY-CAR-CAR-AAY-AAY-AAY-AAY, AAY-CAR-AAY-CAR-AAY-AAY-AAY, AAY-CAR-AAY-AAY-CAR-AAY-AAY, AAY-CAR-AAY-AAY-AAY-CAR-AAY, AAY-CAR-AAY-AAY-AAY-AAY-CAR, AAY-AAY-CAR-CAR-AAY-AAY-AAY, AAY-AAY-CAR-AAY-CAR-AAY-AAY, AAY-AAY-CAR-AAY-AAY-CAR-AAY, AAY-AAY-CAR-AAY-AAY-AAY-CAR, AAY-AAY-AAY-CAR-CAR- TABLE 7-continued (SEQ ID NOS: 2482-4747, respectively, in order of appearance)

AAY-AAY, AAY-AAY-AAY-CAR-AAY-CAR-AAY, AAY-AAY-AAY-CAR-AAY-AAY-CAR, AAY-AAY-AAY-AAY-CAR-CAR-AAY, AAY-AAY-AAY-AAY-CAR-AAY-CAR-AAY-AAY-AAY-AAY-AAY-AAY-CAR,

CAR-AAY-AAY-AAY-AAY-AAY-AAY, AAY-CAR-AAY-AAY-AAY-AAY-AAY, AAY-AAY-CAR-AAY-AAY-AAY-AAY, AAY-AAY-AAY-CAR-AAY-AAY-AAY, AAY-AAY-AAY-AAY-CAR-AAY-AAY, AAY-AAY-AAY-AAY-AAY-CAR-AAY

Oligonucleotides of peptide motifs containing 3-7 amino acid residues with N(Asparagine) as the major constituent and E(Glutamic Acid) as the minor constituent AAY-AAY-GAR, GAR-AAY-AAY, AAY-GAR-AAY, AAY-AAY-AAY-GAR, GAR-AAY-AAY-AAY, AAY-GAR-AAY-AAY, AAY-AAY-GAR-AAY, AAY-AAY-AAY-AAY-GAR, GAR-AAY-AAY-AAY-AAY, AAY-GAR-AAY-AAY-AAY, AAY-AAY-GAR-AAY-AAY, AAY-AAY-AAY-GAR-AAY, AAY-AAY-AAY-GAR-GAR, GAR-GAR-AAY-AAY-AAY, GAR-AAY-GAR-AAY-AAY, GAR-AAY-AAY-GAR-AAY, GAR-AAY-AAY-AAY-GAR, AAY-GAR-GAR-AAY-AAY, AAY-GAR-AAY-GAR-AAY, AAY-GAR-AAY-AAY-GAR, AAY-AAY-GAR-GAR-AAY, AAY-AAY-GAR-AAY-GAR, AAY-AAY-AAY-AAY-AAY-GAR, GAR-AAY-AAY-AAY-AAY-AAY, AAY-GAR-AAY-AAY-AAY-AAY, AAY-AAY-GAR-AAY-AAY-AAY, AAY-AAY-AAY-GAR-AAY-AAY, AAY-AAY-AAY-AAY-GAR-AAY, AAY-AAY-AAY-AAY-GAR-GAR, GAR-GAR-AAY-AAY-AAY-AAY, GAR-AAY-GAR-AAY-AAY-AAY, GAR-AAY-AAY-GAR-AAY-AAY, GAR-AAY-AAY-AAY-GAR-AAY, GAR-AAY-AAY-AAY-AAY-GAR, AAY-GAR-GAR-AAY-AAY-AAY, AAY-GAR-AAY-GAR-AAY-AAY, AAY-GAR-AAY-AAY-GAR-AAY, AAY-GAR-AAY-AAY-AAY-GAR, AAY-AAY-GAR-GAR-AAY-AAY, AAY-AAY-GAR-AAY-GAR-AAY, AAY-AAY-GAR-AAY-AAY-GAR, AAY-AAY-AAY-GAR-GAR-AAY, AAY-AAY-AAY-GAR-AAY-GAR, AAY-AAY-AAY-AAY-GAR-GAR-GAR, GAR-GAR-GAR-AAY-AAY-AAY-AAY, GAR-AAY-GAR-GAR-AAY-AAY-AAY, GAR-AAY-GAR-AAY-GAR-AAY-AAY, GAR-AAY-GAR-AAY-AAY-GAR-AAY, GAR-AAY-GAR-AAY-AAY-AAY-GAR, GAR-AAY-AAY-GAR-GAR-AAY-AAY, GAR-AAY-AAY-GAR-AAY-GAR-AAY, GAR-AAY-AAY-GAR-AAY-AAY-GAR, GAR-AAY-AAY-AAY-GAR-AAY-GAR, GAR-AAY-AAY-AAY-GAR-GAR-AAY, GAR-AAY-AAY-AAY-AAY-GAR-GAR, GAR-GAR-AAY-GAR-AAY-AAY-AAY, GAR-GAR-AAY-AAY-GAR-AAY-AAY, GAR-GAR-AAY-AAY-AAY-GAR-AAY, GAR-GAR-AAY-AAY-AAY-AAY-GAR, AAY-GAR-GAR-GAR-AAY-AAY-AAY, AAY-GAR-GAR-AAY-GAR-AAY-AAY, AAY-GAR-GAR-AAY-AAY-GAR-AAY, AAY-GAR-GAR-AAY-AAY-AAY-GAR, AAY-GAR-AAY-GAR-GAR-AAY-AAY, AAY-GAR-AAY-AAY-GAR-GAR-AAY, AAY-GAR-AAY-AAY-AAY-GAR-GAR, AAY-GAR-AAY-GAR-AAY-GAR-AAY, AAY-GAR-AAY-GAR-AAY-AAY-GAR, AAY-GAR-AAY-AAY-GAR-AAY-GAR, AAY-AAY-GAR-GAR-GAR-AAY-AAY, AAY-AAY-GAR-GAR-AAY-GAR-AAY, AAY-AAY-GAR-GAR-AAY-AAY-GAR, AAY-AAY-GAR-AAY-GAR-GAR-AAY, AAY-AAY-GAR-AAY-GAR-AAY-GAR, AAY-AAY-GAR-AAY-AAY-GAR-GAR, AAY-AAY-AAY-GAR-GAR-GAR-AAY, AAY-AAY-AAY-GAR-GAR-AAY-GAR, AAY-AAY-AAY-GAR-AAY-GAR-GAR, AAY-AAY-AAY-AAY-AAY-GAR-GAR, GAR-GAR-AAY-AAY-AAY-AAY-AAY, GAR-AAY-GAR-AAY-AAY-AAY-AAY, GAR-AAY-AAY-GAR-AAY-AAY-AAY, GAR-AAY-AAY-AAY-GAR-AAY-AAY, GAR-AAY-AAY-AAY-AAY-GAR-AAY, GAR-AAY-AAY-AAY-AAY-AAY-GAR, AAY-GAR-GAR-AAY-AAY-AAY-AAY, AAY-GAR-AAY-GAR-AAY-AAY-AAY, AAY-GAR-AAY-AAY-GAR-AAY-AAY, AAY-GAR-AAY-AAY-AAY-GAR-AAY, AAY-GAR-AAY-AAY-AAY-AAY-GAR, AAY-AAY-GAR-GAR-AAY-AAY-AAY, AAY-AAY-GAR-AAY-GAR-AAY-AAY, AAY-AAY-GAR-AAY-AAY-GAR-AAY, AAY-AAY-GAR-AAY-AAY-AAY-GAR, AAY-AAY-AAY-GAR-GAR-AAY-AAY, AAY-AAY-AAY-GAR-AAY-GAR-AAY, AAY-AAY-AAY-GAR-AAY-AAY-GAR, AAY-AAY-AAY-AAY-GAR-GAR-AAY, AAY-AAY-AAY-AAY-GAR-AAY-GAR-AAY-AAY-AAY-AAY-AAY-AAY-GAR, GAR-AAY-AAY-AAY-AAY-AAY-AAY, AAY-GAR-AAY-AAY-AAY-AAY-AAY, AAY-AAY-GAR-AAY-AAY-AAY-AAY, AAY-AAY-AAY-GAR-AAY-AAY-AAY, AAY-AAY-AAY-AAY-GAR-AAY-AAY, AAY-AAY-AAY-AAY-AAY-GAR-AAY Oligonucleotides of peptide motifs containing 3-7 amino acid residues with N(Asparagine) as the major constituent and H(Histidine) as the minor constituent AAY-AAY-CAY, CAY-AAY-AAY, AAY-CAY-AAY, AAY-AAY-AAY-CAY, CAY-AAY-AAY-AAY, AAY-CAY-AAY-AAY, AAY-AAY-CAY-AAY, AAY-AAY-AAY-AAY-CAY, CAY-AAY-AAY-AAY-AAY, AAY-CAY-AAY-AAY-AAY, AAY-AAY-CAY-AAY-AAY, AAY-AAY-AAY-CAY-AAY, AAY-AAY-AAY-CAY-CAY, CAY-CAY-AAY-AAY-AAY, CAY-AAY-CAY-AAY-AAY, CAY-AAY-AAY-CAY-AAY, CAY-AAY-AAY-AAY-CAY, AAY-CAY-CAY-AAY-AAY, AAY-CAY-AAY-CAY-AAY, AAY-CAY-AAY-AAY-CAY, AAY-AAY-CAY-CAY-AAY, AAY- TABLE 7-continued (SEQ ID NOS: 2482-4747, respectively, in order of appearance)

AAY-CAY-AAY-CAY, AAY-AAY-AAY-AAY-AAY-CAY, CAY-AAY-
AAY-AAY-AAY-AAY, AAY-CAY-AAY-AAY-AAY-AAY, AAY-AAY-
CAY-AAY-AAY-AAY, AAY-AAY-AAY-CAY-AAY-AAY, AAY-AAY-
AAY-AAY-CAY-AAY, AAY-AAY-AAY-AAY-CAY-CAY, CAY-CAY-
AAY-AAY-AAY-AAY, CAY-AAY-CAY-AAY-AAY-AAY, CAY-AAY-
AAY-CAY-AAY-AAY, CAY-AAY-AAY-AAY-CAY-AAY, CAY-AAY-
AAY-AAY-AAY-CAY, AAY-CAY-CAY-AAY-AAY-AAY, AAY-CAY-
AAY-CAY-AAY-AAY, AAY-CAY-AAY-AAY-CAY-AAY, AAY-CAY-
AAY-AAY-AAY-CAY, AAY-AAY-CAY-CAY-AAY-AAY, AAY-AAY-
CAY-AAY-CAY-AAY, AAY-AAY-CAY-AAY-AAY-CAY, AAY-AAY-
AAY-CAY-CAY-AAY, AAY-AAY-AAY-CAY-AAY-CAY, AAY-AAY-
AAY-AAY-CAY-CAY-CAY, CAY-CAY-CAY-AAY-AAY-AAY-AAY,
CAY-AAY-CAY-CAY-AAY-AAY-AAY, CAY-AAY-CAY-AAY-CAY-
AAY-AAY, CAY-AAY-CAY-AAY-AAY-CAY-AAY, CAY-AAY-CAY-
AAY-AAY-AAY-CAY, CAY-AAY-AAY-CAY-CAY-AAY-AAY, CAY-
AAY-AAY-CAY-AAY-CAY-AAY, CAY-AAY-AAY-CAY-AAY-AAY-
CAY, CAY-AAY-AAY-AAY-CAY-AAY-CAY, CAY-AAY-AAY-AAY-
CAY-CAY-AAY, CAY-AAY-AAY-AAY-AAY-CAY-CAY, CAY-CAY-
AAY-CAY-AAY-AAY-AAY, CAY-CAY-AAY-AAY-CAY-AAY-AAY,
CAY-CAY-AAY-AAY-AAY-CAY-AAY, CAY-CAY-AAY-AAY-AAY-
AAY-CAY, AAY-CAY-CAY-CAY-AAY-AAY-AAY, AAY-CAY-CAY-
AAY-CAY-AAY-AAY, AAY-CAY-CAY-AAY-AAY-CAY-AAY, AAY-
CAY-CAY-AAY-AAY-AAY-CAY, AAY-CAY-AAY-CAY-CAY-AAY-
AAY, AAY-CAY-AAY-AAY-CAY-CAY-AAY, AAY-CAY-AAY-AAY-
AAY-CAY-CAY, AAY-CAY-AAY-CAY-AAY-CAY-AAY, AAY-CAY-
AAY-CAY-AAY-AAY-CAY, AAY-CAY-AAY-AAY-CAY-AAY-CAY,
AAY-AAY-CAY-CAY-CAY-AAY-AAY, AAY-AAY-CAY-CAY-AAY-
CAY-AAY, AAY-AAY-CAY-CAY-AAY-AAY-CAY, AAY-AAY-CAY-
AAY-CAY-CAY-AAY, AAY-AAY-CAY-AAY-CAY-AAY-CAY, AAY-
AAY-CAY-AAY-AAY-CAY-CAY, AAY-AAY-AAY-CAY-CAY-CAY-
AAY, AAY-AAY-AAY-CAY-CAY-AAY-CAY, AAY-AAY-AAY-CAY-
AAY-CAY-CAY, AAY-AAY-AAY-AAY-AAY-CAY-CAY, CAY-CAY-
AAY-AAY-AAY-AAY-AAY, CAY-AAY-CAY-AAY-AAY-AAY-AAY,
CAY-AAY-AAY-CAY-AAY-AAY-AAY, CAY-AAY-AAY-AAY-CAY-
AAY-AAY, CAY-AAY-AAY-AAY-AAY-CAY-AAY, CAY-AAY-AAY-
AAY-AAY-AAY-CAY, AAY-CAY-CAY-AAY-AAY-AAY-AAY, AAY-
CAY-AAY-CAY-AAY-AAY-AAY, AAY-CAY-AAY-AAY-CAY-AAY-
AAY, AAY-CAY-AAY-AAY-AAY-CAY-AAY, AAY-CAY-AAY-AAY-
AAY-AAY-CAY, AAY-AAY-CAY-CAY-AAY-AAY-AAY, AAY-AAY-

TABLE 7-continued (SEQ ID NOS: 2482-4747, respectively, in order of appearance)

CAY-AAY-CAY-AAY-AAY, AAY-AAY-CAY-AAY-AAY-CAY-AAY,
AAY-AAY-CAY-AAY-AAY-AAY-CAY, AAY-AAY-AAY-CAY-CAY-
AAY-AAY, AAY-AAY-AAY-CAY-AAY-CAY-AAY, AAY-AAY-AAY-
CAY-AAY-AAY-CAY, AAY-AAY-AAY-AAY-CAY-CAY-AAY, AAY-
AAY-AAY-AAY-CAY-AAY-CAY-AAY-AAY-AAY-AAY-AAY-AAY-
CAY, CAY-AAY-AAY-AAY-AAY-AAY-AAY, AAY-CAY-AAY-AAY-
AAY-AAY-AAY, AAY-AAY-CAY-AAY-AAY-AAY-AAY, AAY-AAY-
AAY-CAY-AAY-AAY-AAY, AAY-AAY-AAY-AAY-CAY-AAY-AAY,
AAY-AAY-AAY-AAY-AAY-CAY-AAY

Oligonucleotides of peptide motifs containing 3-7 amino acid residues with N(Asparagine) as the major constituent and D(Aspartic Acid) as the minor constituent AAY-AAY-GAY, GAY-AAY-AAY, AAY-GAY-AAY, AAY-AAY-AAY-
GAY, GAY-AAY-AAY-AAY, AAY-GAY-AAY-AAY, AAY-AAY-GAY-
AAY, AAY-AAY-AAY-AAY-GAY, GAY-AAY-AAY-AAY-AAY, AAY-
GAY-AAY-AAY-AAY, AAY-AAY-GAY-AAY-AAY, AAY-AAY-AAY-
GAY-AAY, AAY-AAY-AAY-GAY-GAY, GAY-GAY-AAY-AAY-AAY,
GAY-AAY-GAY-AAY-AAY, GAY-AAY-AAY-GAY-AAY, GAY-AAY-
AAY-AAY-GAY, AAY-GAY-GAY-AAY-AAY, AAY-GAY-AAY-GAY-
AAY, AAY-GAY-AAY-AAY-GAY, AAY-AAY-GAY-GAY-AAY, AAY-
AAY-GAY-AAY-GAY, AAY-AAY-AAY-AAY-AAY-GAY, GAY-AAY-
AAY-AAY-AAY-AAY, AAY-GAY-AAY-AAY-AAY-AAY, AAY-AAY-
GAY-AAY-AAY-AAY, AAY-AAY-AAY-GAY-AAY-AAY, AAY-AAY-
AAY-AAY-GAY-AAY, AAY-AAY-AAY-AAY-GAY-GAY, GAY-GAY-
AAY-AAY-AAY-AAY, GAY-AAY-GAY-AAY-AAY-AAY, GAY-AAY-
AAY-GAY-AAY-AAY, GAY-AAY-AAY-AAY-GAY-AAY, GAY-AAY-
AAY-AAY-AAY-GAY, AAY-GAY-GAY-AAY-AAY-AAY, AAY-GAY-
AAY-GAY-AAY-AAY, AAY-GAY-AAY-AAY-GAY-AAY, AAY-GAY-
AAY-AAY-AAY-GAY, AAY-AAY-GAY-GAY-AAY-AAY, AAY-AAY-
GAY-AAY-GAY-AAY, AAY-AAY-GAY-AAY-AAY-GAY, AAY-AAY-
AAY-GAY-GAY-AAY, AAY-AAY-AAY-GAY-AAY-GAY, AAY-AAY-
AAY-AAY-GAY-GAY-GAY, GAY-GAY-GAY-AAY-AAY-AAY-AAY,
GAY-AAY-GAY-GAY-AAY-AAY-AAY, GAY-AAY-GAY-AAY-GAY-
AAY-AAY, GAY-AAY-GAY-AAY-AAY-GAY-AAY, GAY-AAY-GAY-
AAY-AAY-AAY-GAY, GAY-AAY-AAY-GAY-GAY-AAY-AAY, GAY-
AAY-AAY-GAY-AAY-GAY-AAY, GAY-AAY-AAY-GAY-AAY-AAY-
GAY, GAY-AAY-AAY-AAY-GAY-AAY-GAY, GAY-AAY-AAY-AAY-
GAY-GAY-AAY, GAY-AAY-AAY-AAY-AAY-GAY-GAY, GAY-GAY-
AAY-GAY-AAY-AAY-AAY, GAY-GAY-AAY-AAY-GAY-AAY-AAY, TABLE 7-continued (SEQ ID NOS: 2482-4747, respectively, in order of appearance)

GAY-GAY-AAY-AAY-AAY-GAY-AAY, GAY-GAY-AAY-AAY-AAY-AAY-GAY, AAY-GAY-GAY-GAY-AAY-AAY-AAY, AAY-GAY-GAY-AAY-GAY-AAY-AAY, AAY-GAY-GAY-AAY-AAY-GAY-AAY, AAY-GAY-GAY-AAY-AAY-AAY-GAY, AAY-GAY-AAY-GAY-GAY-AAY-AAY, AAY-GAY-AAY-AAY-GAY-GAY-AAY, AAY-GAY-AAY-AAY-AAY-GAY-GAY, AAY-GAY-AAY-GAY-AAY-GAY-AAY, AAY-GAY-AAY-GAY-AAY-AAY-GAY, AAY-GAY-AAY-AAY-GAY-AAY-GAY, AAY-AAY-GAY-GAY-GAY-AAY-AAY, AAY-AAY-GAY-GAY-AAY-GAY-AAY, AAY-AAY-GAY-GAY-AAY-AAY-GAY, AAY-AAY-GAY-AAY-GAY-GAY-AAY, AAY-AAY-GAY-AAY-GAY-AAY-GAY, AAY-AAY-GAY-AAY-AAY-GAY-GAY, AAY-AAY-AAY-GAY-GAY-GAY-AAY, AAY-AAY-AAY-GAY-GAY-AAY-GAY, AAY-AAY-AAY-GAY-AAY-GAY-GAY, AAY-AAY-AAY-AAY-AAY-GAY-GAY, GAY-GAY-AAY-AAY-AAY-AAY-AAY, GAY-AAY-GAY-AAY-AAY-AAY-AAY, GAY-AAY-AAY-GAY-AAY-AAY-AAY, GAY-AAY-AAY-AAY-GAY-AAY-AAY, GAY-AAY-AAY-AAY-AAY-GAY-AAY, GAY-AAY-AAY-AAY-AAY-AAY-GAY, AAY-GAY-GAY-AAY-AAY-AAY-AAY, AAY-GAY-AAY-GAY-AAY-AAY-AAY, AAY-GAY-AAY-AAY-GAY-AAY-AAY, AAY-GAY-AAY-AAY-AAY-GAY-AAY, AAY-GAY-AAY-AAY-AAY-AAY-GAY, AAY-AAY-GAY-GAY-AAY-AAY-AAY, AAY-AAY-GAY-AAY-GAY-AAY-AAY, AAY-AAY-GAY-AAY-AAY-GAY-AAY, AAY-AAY-GAY-AAY-AAY-AAY-GAY, AAY-AAY-AAY-GAY-GAY-AAY-AAY, AAY-AAY-AAY-GAY-AAY-GAY-AAY, AAY-AAY-AAY-GAY-AAY-AAY-GAY, AAY-AAY-AAY-AAY-GAY-GAY-AAY, AAY-AAY-AAY-AAY-GAY-AAY-GAY-AAY-AAY-AAY-AAY-AAY-AAY-GAY,

GAY-AAY-AAY-AAY-AAY-AAY-AAY, AAY-GAY-AAY-AAY-AAY-AAY-AAY, AAY-AAY-GAY-AAY-AAY-AAY-AAY, AAY-AAY-AAY-GAY-AAY-AAY-AAY, AAY-AAY-AAY-AAY-GAY-AAY-AAY, AAY-AAY-AAY-AAY-AAY-GAY-AAY

Oligonucleotides of peptide motifs containing 3-7 amino acide residues with G (glycine) as the major constituent and T(Threonine) as the minor constituent GGN-GGN-ACN, ACN-GGN-GGN, GGN-ACN-GGN, GGN-GGN-GGN-ACN, ACN-GGN-GGN-GGN, GGN-ACN-GGN-GGN, GGN-GGN-ACN-GGN, GGN-GGN-GGN-GGN-ACN, ACN-GGN-GGN-GGN-GGN, GGN-ACN-GGN-GGN-GGN, GGN-GGN-ACN-GGN-GGN, GGN-GGN-GGN-ACN-GGN, GGN-GGN-GGN-ACN-ACN, ACN-ACN-GGN-GGN-GGN, ACN-GGN-ACN-GGN-GGN, ACN-GGN-GGN-ACN-GGN, ACN-GGN- TABLE 7-continued (SEQ ID NOS: 2482-4747, respectively, in order of appearance)

GGN-GGN-ACN, GGN-ACN-ACN-GGN-GGN, GGN-ACN-GGN-ACN-GGN, GGN-ACN-GGN-GGN-ACN, GGN-GGN-ACN-ACN-GGN, GGN-GGN-ACN-GGN-ACN, GGN-GGN-GGN-GGN-GGN-ACN, ACN-GGN-GGN-GGN-GGN-GGN, GGN-ACN-GGN-GGN-GGN-GGN, GGN-GGN-ACN-GGN-GGN-GGN, GGN-GGN-GGN-ACN-GGN-GGN, GGN-GGN-GGN-GGN-ACN-GGN, GGN-GGN-GGN-GGN-ACN-ACN, ACN-ACN-GGN-GGN-GGN-GGN, ACN-GGN-ACN-GGN-GGN-GGN, ACN-GGN-GGN-ACN-GGN-GGN, ACN-GGN-GGN-GGN-ACN-GGN, ACN-GGN-GGN-GGN-GGN-ACN, GGN-ACN-ACN-GGN-GGN-GGN, GGN-ACN-GGN-ACN-GGN-GGN, GGN-ACN-GGN-GGN-ACN-GGN, GGN-ACN-GGN-GGN-GGN-ACN, GGN-GGN-ACN-ACN-GGN-GGN, GGN-GGN-ACN-GGN-ACN-GGN, GGN-GGN-ACN-GGN-GGN-ACN, GGN-GGN-GGN-ACN-ACN-GGN, GGN-GGN-GGN-ACN-GGN-ACN, GGN-GGN-GGN-GGN-ACN-ACN-ACN, ACN-ACN-ACN-GGN-GGN-GGN-GGN, ACN-GGN-ACN-ACN-GGN-GGN-GGN, ACN-GGN-ACN-GGN-ACN-GGN-GGN, ACN-GGN-ACN-GGN-GGN-ACN-GGN, ACN-GGN-ACN-GGN-GGN-GGN-ACN, ACN-GGN-GGN-ACN-ACN-GGN-GGN, ACN-GGN-GGN-ACN-GGN-ACN-GGN, ACN-GGN-GGN-ACN-GGN-GGN-ACN, ACN-GGN-GGN-GGN-ACN-GGN-ACN, ACN-GGN-GGN-GGN-ACN-ACN-GGN, ACN-GGN-GGN-GGN-GGN-ACN-ACN, ACN-ACN-GGN-ACN-GGN-GGN-GGN, ACN-ACN-GGN-GGN-ACN-GGN-GGN, ACN-ACN-GGN-GGN-GGN-ACN-GGN, ACN-ACN-GGN-GGN-GGN-GGN-ACN, GGN-ACN-ACN-ACN-GGN-GGN-GGN, GGN-ACN-ACN-GGN-ACN-GGN-GGN, GGN-ACN-ACN-GGN-GGN-ACN-GGN, GGN-ACN-ACN-GGN-GGN-GGN-ACN, GGN-ACN-GGN-ACN-ACN-GGN-GGN, GGN-ACN-GGN-GGN-ACN-ACN-GGN, GGN-ACN-GGN-GGN-GGN-ACN-ACN, GGN-ACN-GGN-ACN-GGN-ACN-GGN, GGN-ACN-GGN-ACN-GGN-GGN-ACN, GGN-ACN-GGN-GGN-ACN-GGN-ACN, GGN-GGN-ACN-ACN-ACN-GGN-GGN, GGN-GGN-ACN-ACN-GGN-ACN-GGN, GGN-GGN-ACN-ACN-GGN-GGN-ACN, GGN-GGN-ACN-GGN-ACN-ACN-GGN, GGN-GGN-ACN-GGN-ACN-GGN-ACN, GGN-GGN-ACN-GGN-GGN-ACN-ACN, GGN-GGN-GGN-ACN-ACN-ACN-GGN, GGN-GGN-GGN-ACN-ACN-GGN-ACN, GGN-GGN-GGN-ACN-GGN-ACN-ACN, GGN-GGN-GGN-GGN-GGN-ACN-ACN, ACN-ACN-GGN-GGN-GGN-GGN-GGN, ACN-GGN-ACN-GGN-GGN-GGN-GGN, ACN-GGN-GGN-ACN-GGN-GGN-GGN, ACN-GGN-GGN-GGN-ACN-GGN-GGN, ACN-GGN-GGN-GGN-GGN-ACN-GGN, ACN-GGN-GGN-GGN-GGN-GGN-ACN, GGN-ACN-ACN-GGN-GGN-GGN-GGN, GGN-

TABLE 7-continued (SEQ ID NOS: 2482-4747, respectively, in order of appearance)

ACN-GGN-ACN-GGN-GGN-GGN, GGN-ACN-GGN-GGN-ACN-GGN-GGN, GGN-ACN-GGN-GGN-GGN-ACN-GGN, GGN-ACN-GGN-GGN-GGN-GGN-ACN, GGN-GGN-ACN-ACN-GGN-GGN-GGN, GGN-GGN-ACN-GGN-ACN-GGN-GGN, GGN-GGN-ACN-GGN-GGN-ACN-GGN, GGN-GGN-ACN-GGN-GGN-GGN-ACN, GGN-GGN-GGN-ACN-ACN-GGN-GGN, GGN-GGN-GGN-ACN-GGN-ACN-GGN, GGN-GGN-GGN-ACN-GGN-GGN-ACN, GGN-GGN-GGN-GGN-ACN-ACN-GGN, GGN-GGN-GGN-GGN-ACN-GGN-ACN-GGN-GGN-GGN-GGN-GGN-GGN-ACN, ACN-GGN-GGN-GGN-GGN-GGN-GGN, GGN-ACN-GGN-GGN-GGN-GGN-GGN, GGN-GGN-ACN-GGN-GGN-GGN-GGN, GGN-GGN-GGN-ACN-GGN-GGN-GGN, GGN-GGN-GGN-GGN-ACN-GGN-GGN, GGN-GGN-GGN-GGN-GGN-ACN-GGN

Oligonucleotides of peptide motifs containing 3-7 amino acide residues with G(glycine) as the major constituent and A(Alanine) as the minor constituent GGN-GGN-GCN, GCN-GGN-GGN, GGN-GCN-GGN, GGN-GGN-GGN-GCN, GCN-GGN-GGN-GGN, GGN-GCN-GGN-GGN, GGN-GGN-GCN-GGN, GGN-GGN-GGN-GGN-GCN, GCN-GGN-GGN-GGN-GGN, GGN-GCN-GGN-GGN-GGN, GGN-GGN-GCN-GGN-GGN, GGN-GGN-GGN-GCN-GGN, GGN-GGN-GGN-GCN-GCN, GCN-GCN-GGN-GGN-GGN, GCN-GGN-GCN-GGN-GGN, GCN-GGN-GGN-GCN-GGN, GCN-GGN-GGN-GGN-GCN, GGN-GCN-GCN-GGN-GGN, GGN-GCN-GGN-GCN-GGN, GGN-GCN-GGN-GGN-GCN, GGN-GGN-GCN-GCN-GGN, GGN-GGN-GCN-GGN-GCN, GGN-GGN-GGN-GGN-GGN-GCN, GCN-GGN-GGN-GGN-GGN-GGN, GGN-GCN-GGN-GGN-GGN-GGN, GGN-GGN-GCN-GGN-GGN-GGN, GGN-GGN-GGN-GCN-GGN-GGN, GGN-GGN-GGN-GGN-GCN-GGN, GGN-GGN-GGN-GGN-GCN-GCN, GCN-GCN-GGN-GGN-GGN-GGN, GCN-GGN-GCN-GGN-GGN-GGN, GCN-GGN-GGN-GCN-GGN-GGN, GCN-GGN-GGN-GGN-GCN-GGN, GCN-GGN-GGN-GGN-GGN-GCN, GGN-GCN-GCN-GGN-GGN-GGN, GGN-GCN-GGN-GCN-GGN-GGN, GGN-GCN-GGN-GGN-GCN-GGN, GGN-GCN-GGN-GGN-GGN-GCN, GGN-GGN-GCN-GCN-GGN-GGN, GGN-GGN-GCN-GGN-GCN-GGN, GGN-GGN-GCN-GGN-GGN-GCN, GGN-GGN-GGN-GCN-GCN-GGN, GGN-GGN-GGN-GCN-GGN-GCN, GGN-GGN-GGN-GGN-GCN-GCN-GCN, GCN-GCN-GCN-GGN-GGN-GGN-GGN, GCN-GGN-GCN-GCN-GGN-GGN-GGN, GCN-GGN-GCN-GGN-GCN-GGN-GGN, GCN-GGN-GCN-GGN-GGN-GCN-GGN, GCN-GGN-GCN-GGN-GGN-GGN-GCN, GCN-GGN-GGN-GCN-GCN-GGN-GGN, GCN-GGN-GGN-GCN-GGN-GCN-GGN, GCN-GGN-GGN-GCN-GGN-GGN- TABLE 7-continued (SEQ ID NOS: 2482-4747, respectively, in order of appearance)

GCN, GCN-GGN-GGN-GGN-GCN-GGN-GCN, GCN-GGN-GGN-GGN-GCN-GCN-GGN, GCN-GGN-GGN-GGN-GGN-GCN-GCN, GCN-GCN-GGN-GCN-GGN-GGN-GGN, GCN-GCN-GGN-GGN-GCN-GGN-GGN, GCN-GCN-GGN-GGN-GGN-GCN-GGN, GCN-GCN-GGN-GGN-GGN-GGN-GCN, GGN-GCN-GCN-GCN-GGN-GGN-GGN, GGN-GCN-GCN-GGN, GGN-GCN-GCN-GGN-GGN-GCN-GGN, GGN-GCN-GCN-GGN-GGN-GCN-GGN-GGN-GGN-GCN, GGN-GCN-GGN-GCN-GCN-GGN-GGN, GGN-GCN-GGN-GGN-GCN-GCN-GGN, GGN-GCN-GGN-GGN-GGN-GCN-GCN, GGN-GCN-GGN-GCN-GGN-GCN-GGN, GGN-GCN-GGN-GCN-GGN-GGN-GCN, GGN-GCN-GGN-GGN-GCN-GGN-GCN, GGN-GGN-GCN-GCN-GCN-GGN-GGN, GGN-GGN-GCN-GCN-GGN-GCN-GGN, GGN-GGN-GCN-GCN-GGN-GGN-GCN, GGN-GGN-GCN-GGN-GCN-GCN-GGN, GGN-GGN-GCN-GGN-GCN-GGN-GCN, GGN-GGN-GCN-GGN-GGN-GCN-GCN, GGN-GGN-GGN-GCN-GCN-GCN-GGN, GGN-GGN-GGN-GCN-GCN-GGN-GCN, GGN-GGN-GGN-GCN-GGN-GCN-GCN, GGN-GGN-GGN-GGN-GCN-GCN-GCN, GCN-GCN-GGN-GGN-GGN-GGN-GGN, GCN-GGN-GCN-GGN-GGN-GGN-GGN, GCN-GGN-GGN-GCN-GGN-GGN-GGN, GCN-GGN-GGN-GGN-GCN-GGN-GGN, GCN-GGN-GGN-GGN-GGN-GCN-GGN, GCN-GGN-GGN-GGN-GGN-GGN-GCN, GGN-GCN-GCN-GGN-GGN-GGN-GGN, GGN-GCN-GGN-GCN-GGN-GGN-GGN, GGN-GCN-GGN-GGN-GCN-GGN-GGN, GGN-GCN-GGN-GGN-GGN-GCN-GGN, GGN-GCN-GGN-GGN-GGN-GGN-GCN, GGN-GGN-GCN-GCN-GGN-GGN-GGN, GGN-GGN-GCN-GGN-GCN-GGN-GGN, GGN-GGN-GCN-GGN-GGN-GCN-GGN, GGN-GGN-GCN-GGN-GGN-GGN-GCN, GGN-GGN-GGN-GCN-GCN-GGN-GGN, GGN-GGN-GGN-GCN-GGN-GCN-GGN, GGN-GGN-GGN-GCN-GGN-GGN-GCN, GGN-GGN-GGN-GGN-GCN-GCN-GGN, GGN-GGN-GGN-GGN-GCN-GGN-GCN-GGN-GGN-GGN-GGN-GGN-GGN-GCN,

GCN-GGN-GGN-GGN-GGN-GGN-GGN, GGN-GCN-GGN-GGN-GGN-GGN-GGN, GGN-GGN-GCN-GGN-GGN-GGN-GGN, GGN-GGN-GGN-GCN-GGN-GGN-GGN, GGN-GGN-GGN-GGN-GCN-GGN-GGN, GGN-GGN-GGN-GGN-GGN-GCN-GGN

Oligonucleotides of peptide motifs containing 3-7 amino acide residues with G(glycine) as the major constituent and S(Serine) as the minor constituent GGN-GGN-AGY, AGY-GGN-GGN, GGN-AGY-GGN, GGN-GGN-GGN-AGY, AGY-GGN-GGN-GGN, GGN-AGY-GGN-GGN, GGN-GGN-AGY-GGN, GGN-GGN-GGN-GGN-AGY, AGY-GGN-GGN-GGN-GGN, GGN- TABLE 7-continued

| (SEQ ID NOS: 2482-4747, respectively, in order of appearance) |
| --- |
| AGY-GGN-GGN-GGN, GGN-GGN-AGY-GGN-GGN, GGN-GGN-GGN-AGY-GGN, GGN-GGN-GGN-AGY-AGY, AGY-AGY-GGN-GGN-GGN, AGY-GGN-AGY-GGN-GGN, AGY-GGN-GGN-AGY-GGN, AGY-GGN-GGN-GGN-AGY, GGN-AGY-AGY-GGN-GGN, GGN-AGY-GGN-AGY-GGN, GGN-AGY-GGN-GGN-AGY, GGN-GGN-AGY-AGY-GGN, GGN-GGN-AGY-GGN-AGY, GGN-GGN-GGN-GGN-GGN-AGY, AGY-GGN-GGN-GGN-GGN-GGN, GGN-AGY-GGN-GGN-GGN-GGN, GGN-GGN-AGY-GGN-GGN-GGN, GGN-GGN-GGN-AGY-GGN-GGN, GGN-GGN-GGN-GGN-AGY-GGN, GGN-GGN-GGN-GGN-AGY-AGY, AGY-AGY-GGN-GGN-GGN-GGN, AGY-GGN-AGY-GGN-GGN-GGN, AGY-GGN-GGN-AGY-GGN-GGN, AGY-GGN-GGN-GGN-AGY-GGN, AGY-GGN-GGN-GGN-GGN-AGY, GGN-AGY-AGY-GGN-GGN-GGN, GGN-AGY-GGN-AGY-GGN-GGN, GGN-AGY-GGN-GGN-AGY-GGN, GGN-AGY-GGN-GGN-GGN-AGY, GGN-GGN-AGY-AGY-GGN-GGN, GGN-GGN-AGY-GGN-AGY-GGN, GGN-GGN-AGY-GGN-GGN-AGY, GGN-GGN-GGN-AGY-AGY-GGN, GGN-GGN-GGN-AGY-GGN-AGY, GGN-GGN-GGN-GGN-AGY-AGY-AGY, AGY-AGY-AGY-GGN-GGN-GGN-GGN, AGY-GGN-AGY-AGY-GGN-GGN-GGN, AGY-GGN-AGY-GGN-AGY-GGN-GGN, AGY-GGN-AGY-GGN-GGN-AGY-GGN, AGY-GGN-AGY-GGN-GGN-GGN-AGY, AGY-GGN-GGN-AGY-AGY-GGN-GGN, AGY-GGN-GGN-AGY-GGN-AGY-GGN, AGY-GGN-GGN-AGY-GGN-GGN-AGY, AGY-GGN-GGN-GGN-AGY-GGN-AGY, AGY-GGN-GGN-GGN-AGY-AGY-GGN, AGY-GGN-GGN-GGN-GGN-AGY-AGY, AGY-AGY-GGN-AGY-GGN-GGN-GGN, AGY-AGY-GGN-GGN-AGY-GGN-GGN, AGY-AGY-GGN-GGN-GGN-AGY-GGN, AGY-AGY-GGN-GGN-GGN-GGN-AGY, GGN-AGY-AGY-AGY-GGN-GGN-GGN, GGN-AGY-AGY-GGN-AGY-GGN-GGN, GGN-AGY-AGY-GGN-GGN-AGY-GGN, GGN-AGY-AGY-GGN-GGN-GGN-AGY, GGN-AGY-GGN-AGY-AGY-GGN-GGN, GGN-AGY-GGN-GGN-AGY-AGY-GGN, GGN-AGY-GGN-GGN-GGN-AGY-AGY, GGN-AGY-GGN-AGY-GGN-AGY-GGN, GGN-AGY-GGN-AGY-GGN-GGN-AGY, GGN-AGY-GGN-GGN-AGY-GGN-AGY, GGN-GGN-AGY-AGY-AGY-GGN-GGN, GGN-GGN-AGY-AGY-GGN-AGY-GGN, GGN-GGN-AGY-AGY-GGN-GGN-AGY, GGN-GGN-AGY-GGN-AGY-AGY-GGN, GGN-GGN-AGY-GGN-AGY-GGN-AGY, GGN-GGN-AGY-GGN-GGN-AGY-AGY, GGN-GGN-GGN-AGY-AGY-AGY-GGN, GGN-GGN-GGN-AGY-AGY-GGN-AGY, GGN-GGN-GGN-AGY-GGN-AGY-AGY, GGN-GGN-GGN-GGN-GGN-AGY-AGY, AGY-AGY-GGN-GGN-GGN-GGN-GGN, AGY-GGN-AGY-GGN-GGN-GGN-GGN, AGY-GGN-GGN-AGY-GGN-GGN-GGN, AGY-GGN-GGN-GGN-AGY-GGN-GGN, AGY-GGN-GGN-GGN-GGN-AGY-GGN, AGY-GGN-GGN-GGN-GGN-GGN-AGY, GGN-AGY-AGY-GGN-GGN-GGN-GGN, GGN-AGY-GGN-AGY-GGN-GGN-GGN, GGN-AGY-GGN-GGN-AGY-GGN-GGN, GGN-AGY-GGN-GGN-GGN-AGY-GGN, GGN-AGY-GGN-GGN-GGN-GGN-AGY, GGN-GGN-AGY-AGY-GGN-GGN-GGN, GGN-GGN-AGY-GGN-AGY-GGN-GGN, GGN-GGN-AGY-GGN-GGN-AGY-GGN, GGN-GGN-AGY-GGN-GGN-GGN-AGY, GGN-GGN-GGN-AGY-AGY-GGN-GGN, GGN-GGN-GGN-AGY-GGN-AGY-GGN, GGN-GGN-GGN-AGY-GGN-GGN-AGY, GGN-GGN-GGN-GGN-AGY-AGY-GGN, GGN-GGN-GGN-GGN-AGY-GGN-AGY-GGN-GGN-GGN-GGN-GGN-GGN-AGY, AGY-GGN-GGN-GGN-GGN-GGN-GGN, GGN-AGY-GGN-GGN-GGN-GGN-GGN, GGN-GGN-AGY-GGN-GGN-GGN-GGN, GGN-GGN-GGN-AGY-GGN-GGN-GGN, GGN-GGN-GGN-GGN-AGY-GGN-GGN, GGN-GGN-GGN-GGN-GGN-AGY-GGN |
| Oligonucleotides of peptide motifs containing 3-7 amino acide residues with G(glycine) as the major constituent and Q(Glutamine) as the minor constituent |
| GGN-GGN-CAR, CAR-GGN-GGN, GGN-CAR-GGN, GGN-GGN-GGN-CAR, CAR-GGN-GGN-GGN, GGN-CAR-GGN-GGN, GGN-GGN-CAR-GGN, GGN-GGN-GGN-GGN-CAR, CAR-GGN-GGN-GGN-GGN, GGN-CAR-GGN-GGN-GGN, GGN-GGN-CAR-GGN-GGN, GGN-GGN-GGN-CAR-GGN, GGN-GGN-GGN-CAR-CAR, CAR-CAR-GGN-GGN-GGN, CAR-GGN-CAR-GGN-GGN, CAR-GGN-GGN-CAR-GGN, CAR-GGN-GGN-GGN-CAR, GGN-CAR-CAR-GGN-GGN, GGN-CAR-GGN-CAR-GGN, GGN-CAR-GGN-GGN-CAR, GGN-GGN-CAR-CAR-GGN, GGN-GGN-CAR-GGN-CAR, GGN-GGN-GGN-GGN-GGN-CAR, CAR-GGN-GGN-GGN-GGN-GGN, GGN-CAR-GGN-GGN-GGN-GGN, GGN-GGN-CAR-GGN-GGN-GGN, GGN-GGN-GGN-CAR-GGN-GGN, GGN-GGN-GGN-GGN-CAR-GGN, GGN-GGN-GGN-GGN-CAR-CAR, CAR-CAR-GGN-GGN-GGN-GGN, CAR-GGN-CAR-GGN-GGN-GGN, CAR-GGN-GGN-CAR-GGN-GGN, CAR-GGN-GGN-GGN-CAR-GGN, CAR-GGN-GGN-GGN-GGN-CAR, GGN-CAR-CAR-GGN-GGN-GGN, GGN-CAR-GGN-CAR-GGN-GGN, GGN-CAR-GGN-GGN-CAR-GGN, GGN-CAR-GGN-GGN-GGN-CAR, GGN-GGN-CAR-CAR-GGN-GGN, GGN-GGN-CAR-GGN-CAR-GGN, GGN-GGN-CAR-GGN-GGN-CAR, GGN-GGN-GGN-CAR-CAR-GGN, GGN-GGN-GGN-CAR-GGN-CAR, GGN-GGN-GGN-GGN-CAR-CAR-CAR, CAR-CAR-CAR-GGN-GGN-GGN-GGN, |

TABLE 7-continued (SEQ ID NOS: 2482-4747, respectively, in order of appearance)

CAR-GGN-CAR-CAR-GGN-GGN-GGN, CAR-GGN-CAR-GGN-CAR-GGN-GGN, CAR-GGN-CAR-GGN-GGN-CAR-GGN, CAR-GGN-CAR-GGN-GGN-GGN-CAR, CAR-GGN-GGN-CAR-CAR-GGN-GGN, CAR-GGN-GGN-CAR-GGN-CAR-GGN, CAR-GGN-GGN-CAR-GGN-GGN-CAR, CAR-GGN-GGN-GGN-CAR-GGN-CAR, CAR-GGN-GGN-CAR-CAR-GGN, CAR-GGN-GGN-GGN-GGN-CAR-CAR, CAR-CAR-GGN-CAR-GGN-GGN-GGN, CAR-CAR-GGN-GGN-CAR-GGN-GGN, CAR-CAR-GGN-GGN-GGN-CAR-GGN, CAR-CAR-GGN-GGN-GGN-CAR, GGN-CAR-CAR-CAR-GGN-GGN-GGN, GGN-CAR-CAR-GGN-CAR-GGN-GGN, GGN-CAR-CAR-GGN-GGN-CAR-GGN, GGN-CAR-CAR-GGN-GGN-GGN-CAR, GGN-CAR-GGN-CAR-CAR-GGN-GGN, GGN-CAR-GGN-GGN-CAR-CAR-GGN, GGN-CAR-GGN-GGN-CAR-CAR, GGN-CAR-GGN-CAR-GGN-CAR-GGN, GGN-CAR-GGN-CAR-GGN-GGN-CAR, GGN-CAR-GGN-GGN-CAR-GGN-CAR, GGN-GGN-CAR-CAR-CAR-GGN-GGN, GGN-GGN-CAR-CAR-GGN-CAR-GGN, GGN-GGN-CAR-CAR-GGN-GGN-CAR, GGN-GGN-CAR-GGN-CAR-CAR-GGN, GGN-GGN-CAR-GGN-CAR-GGN-CAR, GGN-GGN-CAR-GGN-GGN-CAR-CAR, GGN-GGN-GGN-CAR-CAR-CAR-GGN, GGN-GGN-GGN-CAR-CAR-GGN-CAR, GGN-GGN-GGN-CAR-GGN-CAR-CAR, GGN-GGN-GGN-GGN-GGN-CAR-CAR, CAR-CAR-GGN-GGN-GGN-GGN-GGN, CAR-GGN-CAR-GGN-GGN-GGN-GGN, CAR-GGN-GGN-CAR-GGN-GGN-GGN, CAR-GGN-GGN-GGN-CAR-GGN-GGN, CAR-GGN-GGN-GGN-GGN-CAR-GGN, CAR-GGN-GGN-GGN-GGN-GGN-CAR, GGN-CAR-CAR-GGN-GGN-GGN-GGN, GGN-CAR-GGN-CAR-GGN-GGN-GGN, GGN-CAR-GGN-GGN-CAR-GGN-GGN, GGN-CAR-GGN-GGN-GGN-CAR-GGN, GGN-CAR-GGN-GGN-GGN-GGN-CAR, GGN-GGN-CAR-CAR-GGN-GGN-GGN, GGN-GGN-CAR-GGN-CAR-GGN-GGN, GGN-GGN-CAR-GGN-GGN-CAR-GGN, GGN-GGN-CAR-GGN-GGN-GGN-CAR, GGN-GGN-GGN-CAR-CAR-GGN-GGN, GGN-GGN-GGN-CAR-GGN-CAR-GGN, GGN-GGN-GGN-CAR-GGN-GGN-CAR, GGN-GGN-GGN-GGN-CAR-CAR-GGN, GGN-GGN-GGN-GGN-CAR-GGN-CAR-GGN-GGN-GGN-GGN-GGN-GGN-CAR,

CAR-GGN-GGN-GGN-GGN-GGN-GGN, GGN-CAR-GGN-GGN-GGN-GGN-GGN, GGN-GGN-CAR-GGN-GGN-GGN-GGN, GGN-GGN-GGN-CAR-GGN-GGN-GGN, GGN-GGN-GGN-GGN-CAR-GGN-GGN, GGN-GGN-GGN-GGN-GGN-CAR-GGN

Oligonucleotides of peptide motifs containing 3-7 amino acide residues with G(glycine) as the major constituent and E(Glutamic Acid) as the minor constituent GGN-GGN-GAR, GAR-GGN-GGN, GGN-GAR-GGN, GGN-GGN-GGN-GAR, GAR-GGN-GGN-GGN, GGN-GAR-GGN-GGN, GGN-GGN-GAR-GGN, GGN-GGN-GGN-GGN-GAR, GAR-GGN-GGN-GGN-GGN, GGN-GAR-GGN-GGN-GGN, GGN-GGN-GAR-GGN-GGN, GGN-GGN-GGN-GAR-GGN, GGN-GGN-GGN-GAR-GAR, GAR-GAR-GGN-GGN-GGN, GAR-GGN-GAR-GGN-GGN, GAR-GGN-GGN-GAR-GGN, GAR-GGN-GGN-GGN-GAR, GGN-GAR-GAR-GGN-GGN, GGN-GAR-GGN-GAR-GGN, GGN-GAR-GGN-GGN-GAR, GGN-GGN-GAR-GAR-GGN, GGN-GGN-GAR-GGN-GAR, GGN-GGN-GGN-GGN-GGN-GAR, GAR-GGN-GGN-GGN-GGN-GGN, GGN-GAR-GGN-GGN-GGN-GGN, GGN-GGN-GAR-GGN-GGN-GGN, GGN-GGN-GGN-GAR-GGN-GGN, GGN-GGN-GGN-GGN-GAR-GGN, GGN-GGN-GGN-GGN-GAR-GAR, GAR-GAR-GGN-GGN-GGN-GGN, GAR-GGN-GAR-GGN-GGN-GGN, GAR-GGN-GGN-GAR-GGN-GGN, GAR-GGN-GGN-GGN-GAR-GGN, GAR-GGN-GGN-GGN-GGN-GAR, GGN-GAR-GAR-GGN-GGN-GGN, GGN-GAR-GGN-GAR-GGN-GGN, GGN-GAR-GGN-GGN-GAR-GGN, GGN-GAR-GGN-GGN-GGN-GAR, GGN-GGN-GAR-GAR-GGN-GGN, GGN-GGN-GAR-GGN-GAR-GGN, GGN-GGN-GAR-GGN-GGN-GAR, GGN-GGN-GGN-GAR-GAR-GGN, GGN-GGN-GGN-GAR-GGN-GAR, GGN-GGN-GGN-GGN-GAR-GAR-GAR, GAR-GAR-GAR-GGN-GGN-GGN-GGN, GAR-GGN-GAR-GAR-GGN-GGN-GGN, GAR-GGN-GAR-GGN-GAR-GGN-GGN, GAR-GGN-GAR-GGN-GGN-GAR-GGN, GAR-GGN-GAR-GGN-GGN-GGN-GAR, GAR-GGN-GGN-GAR-GAR-GGN-GGN, GAR-GGN-GGN-GAR-GGN-GAR-GGN, GAR-GGN-GGN-GAR-GGN-GGN-GAR, GAR-GGN-GGN-GGN-GAR-GGN-GAR, GAR-GGN-GGN-GGN-GAR-GAR-GGN, GAR-GGN-GGN-GGN-GGN-GAR-GAR, GAR-GAR-GGN-GAR-GGN-GGN-GGN, GAR-GAR-GGN-GGN-GAR-GGN-GGN, GAR-GAR-GGN-GGN-GGN-GAR-GGN, GAR-GAR-GGN-GGN-GGN-GGN-GAR, GGN-GAR-GAR-GAR-GGN-GGN-GGN, GGN-GAR-GAR-GGN-GAR-GGN-GGN, GGN-GAR-GAR-GGN-GGN-GAR-GGN, GGN-GAR-GAR-GGN-GGN-GGN-GAR, GGN-GAR-GGN-GAR-GAR-GGN-GGN, GGN-GAR-GGN-GGN-GAR-GAR-GGN, GGN-GAR-GGN-GGN-GGN-GAR-GAR, GGN-GAR-GGN-GAR-GGN-GAR-GGN, GGN-GAR-GGN-GAR-GGN-GGN-GAR, GGN-GAR-GGN-GGN-GAR-GGN-GAR, GGN-GGN-GAR-GAR-GAR-GGN-GGN, GGN-GGN-GAR-GAR-GGN-GAR-GGN, GGN-GGN-GAR-GAR-GGN-GGN-GAR, GGN-GGN-GAR- TABLE 7-continued

| (SEQ ID NOS: 2482-4747, respectively, in order of appearance) |
|---|
| GGN-GAR-GAR-GGN, GGN-GGN-GAR-GGN-GAR-GGN-GAR, GGN-GGN-GAR-GGN-GGN-GAR-GAR, GGN-GGN-GGN-GAR-GAR-GAR-GGN, GGN-GGN-GGN-GAR-GAR-GGN-GAR, GGN-GGN-GGN-GAR-GGN-GAR-GAR, GGN-GGN-GGN-GGN-GGN-GAR-GAR, GAR-GAR-GGN-GGN-GGN-GGN-GGN, GAR-GGN-GAR-GGN-GGN-GGN-GGN, GAR-GGN-GGN-GAR-GGN-GGN-GGN, GAR-GGN-GGN-GGN-GAR-GGN-GGN, GAR-GGN-GGN-GGN-GGN-GAR-GGN, GAR-GGN-GGN-GGN-GGN-GGN-GAR, GGN-GAR-GAR-GGN-GGN-GGN-GGN, GGN-GAR-GGN-GAR-GGN-GGN-GGN, GGN-GAR-GGN-GGN-GAR-GGN-GGN, GGN-GAR-GGN-GGN-GGN-GAR-GGN, GGN-GAR-GGN-GGN-GGN-GGN-GAR, GGN-GGN-GAR-GAR-GGN-GGN-GGN, GGN-GGN-GAR-GGN-GAR-GGN-GGN, GGN-GGN-GAR-GGN-GGN-GAR-GGN, GGN-GGN-GAR-GGN-GGN-GGN-GAR, GGN-GGN-GGN-GAR-GAR-GGN-GGN, GGN-GGN-GGN-GAR-GGN-GAR-GGN, GGN-GGN-GGN-GAR-GGN-GGN-GAR, GGN-GGN-GGN-GGN-GAR-GAR-GGN, GGN-GGN-GGN-GGN-GAR-GGN-GAR-GGN-GGN-GGN-GGN-GGN-GGN-GAR, |
| GAR-GGN-GGN-GGN-GGN-GGN-GGN, GGN-GAR-GGN-GGN-GGN-GGN-GGN, GGN-GGN-GAR-GGN-GGN-GGN-GGN, GGN-GGN-GGN-GAR-GGN-GGN-GGN, GGN-GGN-GGN-GGN-GAR-GGN-GGN, GGN-GGN-GGN-GGN-GGN-GAR-GGN |
| Oligonucleotides of peptide motifs containing 3-7 amino acide residues with G(glycine) as the major constituent and H(Histidine) as the minor constituent |
| GGN-GGN-CAY, CAY-GGN-GGN, GGN-CAY-GGN, GGN-GGN-GGN-CAY, CAY-GGN-GGN-GGN, GGN-CAY-GGN-GGN, GGN-GGN-CAY-GGN, GGN-GGN-GGN-GGN-CAY, CAY-GGN-GGN-GGN-GGN, GGN-CAY-GGN-GGN-GGN, GGN-GGN-CAY-GGN-GGN, GGN-GGN-GGN-CAY-GGN, GGN-GGN-GGN-CAY-CAY, CAY-CAY-GGN-GGN-GGN, CAY-GGN-CAY-GGN-GGN, CAY-GGN-GGN-CAY-GGN, CAY-GGN-GGN-GGN-CAY, GGN-CAY-CAY-GGN-GGN, GGN-CAY-GGN-CAY-GGN, GGN-CAY-GGN-GGN-CAY, GGN-GGN-CAY-CAY-GGN, GGN-GGN-CAY-GGN-CAY, GGN-GGN-GGN-GGN-GGN-CAY, CAY-GGN-GGN-GGN-GGN-GGN, GGN-CAY-GGN-GGN-GGN-GGN, GGN-GGN-CAY-GGN-GGN-GGN, GGN-GGN-GGN-CAY-GGN-GGN, GGN-GGN-GGN-GGN-CAY-GGN, GGN-GGN-GGN-GGN-CAY-CAY, CAY-CAY-GGN-GGN-GGN-GGN, CAY-GGN-CAY-GGN-GGN-GGN, CAY-GGN-GGN-CAY-GGN-GGN, CAY-GGN-GGN-GGN-CAY-GGN, CAY-GGN-GGN-GGN-GGN-CAY, GGN-CAY-CAY-GGN-GGN-GGN, GGN-CAY-GGN-CAY-GGN-GGN, GGN-CAY-GGN-GGN-CAY-GGN, GGN-CAY-GGN-GGN-GGN-CAY, GGN-GGN-CAY-CAY-GGN-GGN, GGN-GGN-CAY-GGN-CAY-GGN, GGN-GGN-CAY-GGN-GGN-CAY, GGN-GGN-GGN-CAY-CAY-GGN, GGN-GGN-GGN-CAY-GGN-CAY, GGN-GGN-GGN-GGN-CAY-CAY-CAY, CAY-CAY-CAY-GGN-GGN-GGN-GGN, CAY-GGN-CAY-CAY-GGN-GGN-GGN, CAY-GGN-CAY-GGN-CAY-GGN-GGN, CAY-GGN-CAY-GGN-GGN-CAY-GGN, CAY-GGN-CAY-GGN-GGN-GGN-CAY, CAY-GGN-GGN-CAY-CAY-GGN-GGN, CAY-GGN-GGN-CAY-GGN-CAY-GGN, CAY-GGN-GGN-CAY-GGN-GGN-CAY, CAY-GGN-GGN-GGN-CAY-GGN-CAY, CAY-GGN-GGN-GGN-CAY-CAY-GGN, CAY-GGN-GGN-GGN-GGN-CAY-CAY, CAY-CAY-GGN-CAY-GGN-GGN-GGN, CAY-CAY-GGN-GGN-CAY-GGN-GGN, CAY-CAY-GGN-GGN-GGN-CAY-GGN, CAY-CAY-GGN-GGN-GGN-GGN-CAY, GGN-CAY-CAY-CAY-GGN-GGN-GGN, GGN-CAY-CAY-GGN-CAY-GGN-GGN, GGN-CAY-CAY-GGN-GGN-CAY-GGN, GGN-CAY-CAY-GGN-GGN-GGN-CAY, GGN-CAY-GGN-CAY-CAY-GGN-GGN, GGN-CAY-GGN-GGN-CAY-CAY-GGN, GGN-CAY-GGN-GGN-GGN-CAY-CAY, GGN-CAY-GGN-CAY-GGN-CAY-GGN, GGN-CAY-GGN-CAY-GGN-GGN-CAY, GGN-CAY-GGN-GGN-CAY-GGN-CAY, GGN-GGN-CAY-CAY-CAY-GGN-GGN, GGN-GGN-CAY-CAY-GGN-CAY-GGN, GGN-GGN-CAY-CAY-GGN-GGN-CAY, GGN-GGN-CAY-GGN-CAY-CAY-GGN, GGN-GGN-CAY-GGN-CAY-GGN-CAY, GGN-GGN-CAY-GGN-GGN-CAY-CAY, GGN-GGN-GGN-CAY-CAY-CAY-GGN, GGN-GGN-GGN-CAY-CAY-GGN-CAY, GGN-GGN-GGN-CAY-GGN-CAY-CAY, GGN-GGN-GGN-GGN-GGN-CAY-CAY, CAY-CAY-GGN-GGN-GGN-GGN-GGN, CAY-GGN-CAY-GGN-GGN-GGN-GGN, CAY-GGN-GGN-CAY-GGN-GGN-GGN, CAY-GGN-GGN-GGN-CAY-GGN-GGN, CAY-GGN-GGN-GGN-GGN-CAY-GGN, CAY-GGN-GGN-GGN-GGN-GGN-CAY, GGN-CAY-CAY-GGN-GGN-GGN-GGN, GGN-CAY-GGN-CAY-GGN-GGN-GGN, GGN-CAY-GGN-GGN-CAY-GGN-GGN, GGN-CAY-GGN-GGN-GGN-CAY-GGN, GGN-CAY-GGN-GGN-GGN-GGN-CAY, GGN-GGN-CAY-CAY-GGN-GGN-GGN, GGN-GGN-CAY-GGN-CAY-GGN-GGN, GGN-GGN-CAY-GGN-GGN-CAY-GGN, GGN-GGN-CAY-GGN-GGN-GGN-CAY, GGN-GGN-GGN-CAY-CAY-GGN-GGN, GGN-GGN-GGN-CAY-GGN-CAY-GGN, GGN-GGN-GGN-CAY-GGN-GGN-CAY, GGN-GGN-GGN-GGN-CAY-CAY-GGN, GGN-GGN-GGN-GGN-CAY-GGN-CAY-GGN-GGN-GGN-GGN-GGN-GGN-CAY, |
| CAY-GGN-GGN-GGN-GGN-GGN-GGN, GGN-CAY-GGN-GGN-GGN- |

TABLE 7-continued

| (SEQ ID NOS: 2482-4747, respectively, in order of appearance) |
|---|
| GGN-GGN, GGN-GGN-CAY-GGN-GGN-GGN-GGN, GGN-GGN-GGN-CAY-GGN-GGN-GGN, GGN-GGN-GGN-GGN-CAY-GGN-GGN, GGN-GGN-GGN-GGN-GGN-CAY-GGN |
| Oligonucleotides of peptide motifs containing 3-7 amino acide residues with G(glycine) as the major constituent and N(Asparagine) as the minor constituent |
| GGN-GGN-AAY, AAY-GGN-GGN, GGN-AAY-GGN, GGN-GGN-GGN-AAY, AAY-GGN-GGN-GGN, GGN-AAY-GGN-GGN, GGN-GGN-AAY-GGN, GGN-GGN-GGN-GGN-AAY, AAY-GGN-GGN-GGN-GGN, GGN-AAY-GGN-GGN-GGN, GGN-GGN-AAY-GGN-GGN, GGN-GGN-GGN-AAY-GGN, GGN-GGN-GGN-AAY-AAY, AAY-AAY-GGN-GGN-GGN, AAY-GGN-AAY-GGN-GGN, AAY-GGN-GGN-AAY-GGN, AAY-GGN-GGN-GGN-AAY, GGN-AAY-AAY-GGN-GGN, GGN-AAY-GGN-AAY-GGN, GGN-AAY-GGN-GGN-AAY, GGN-GGN-AAY-AAY-GGN, GGN-GGN-AAY-GGN-AAY, GGN-GGN-GGN-GGN-GGN-AAY, AAY-GGN-GGN-GGN-GGN-GGN, GGN-AAY-GGN-GGN-GGN-GGN, GGN-GGN-AAY-GGN-GGN-GGN, GGN-GGN-GGN-AAY-GGN-GGN, GGN-GGN-GGN-GGN-AAY-GGN, GGN-GGN-GGN-GGN-AAY-AAY, AAY-AAY-GGN-GGN-GGN-GGN, AAY-GGN-AAY-GGN-GGN-GGN, AAY-GGN-GGN-AAY-GGN-GGN, AAY-GGN-GGN-GGN-AAY-GGN, AAY-GGN-GGN-GGN-GGN-AAY, GGN-AAY-AAY-GGN-GGN-GGN, GGN-AAY-GGN-AAY-GGN-GGN, GGN-AAY-GGN-GGN-AAY-GGN, GGN-AAY-GGN-GGN-GGN-AAY, GGN-GGN-AAY-AAY-GGN-GGN, GGN-GGN-AAY-GGN-AAY-GGN, GGN-GGN-AAY-GGN-GGN-AAY, GGN-GGN-GGN-AAY-AAY-GGN, GGN-GGN-GGN-AAY-GGN-AAY, GGN-GGN-GGN-GGN-AAY-AAY-AAY, AAY-AAY-AAY-GGN-GGN-GGN-GGN, AAY-GGN-AAY-AAY-GGN-GGN-GGN, AAY-GGN-AAY-GGN-AAY-GGN-GGN, AAY-GGN-AAY-GGN-GGN-AAY-GGN, AAY-GGN-AAY-GGN-GGN-GGN-AAY, AAY-GGN-GGN-AAY-AAY-GGN-GGN, AAY-GGN-GGN-AAY-GGN-AAY-GGN, AAY-GGN-GGN-AAY-GGN-GGN-AAY, AAY-GGN-GGN-GGN-AAY-GGN-AAY, AAY-GGN-GGN-GGN-AAY-AAY-GGN, AAY-GGN-GGN-GGN-GGN-AAY-AAY, AAY-AAY-GGN-AAY-GGN-GGN-GGN, AAY-AAY-GGN-GGN-AAY-GGN-GGN, AAY-AAY-GGN-GGN-GGN-AAY-GGN, AAY-AAY-GGN-GGN-GGN-GGN-AAY, GGN-AAY-AAY-AAY-GGN-GGN-GGN, GGN-AAY-AAY-GGN-AAY-GGN-GGN, GGN-AAY-AAY-GGN-GGN-AAY-GGN, GGN-AAY-AAY-GGN-GGN-GGN-AAY, GGN-AAY-GGN-AAY-AAY-GGN-GGN, GGN-AAY-GGN-GGN-AAY-AAY-GGN, GGN-AAY-GGN-GGN-GGN-AAY-AAY, GGN-AAY-GGN-AAY-GGN-AAY-GGN, GGN-AAY-GGN-AAY-GGN-GGN-AAY, GGN-AAY-GGN-GGN-AAY-GGN-AAY, GGN-GGN-AAY-AAY-AAY-GGN-GGN, GGN-GGN-AAY-AAY-GGN-AAY-GGN, GGN-GGN-AAY-AAY-GGN-GGN-AAY, GGN-GGN-AAY-GGN-AAY-AAY-GGN, GGN-GGN-AAY-GGN-AAY-GGN-AAY, GGN-GGN-AAY-GGN-GGN-AAY-AAY, GGN-GGN-GGN-AAY-AAY-AAY-GGN, GGN-GGN-GGN-AAY-AAY-GGN-AAY, GGN-GGN-GGN-AAY-GGN-AAY-AAY, GGN-GGN-GGN-GGN-GGN-AAY-AAY, AAY-AAY-GGN-GGN-GGN-GGN-GGN, AAY-GGN-AAY-GGN-GGN-GGN-GGN, AAY-GGN-GGN-AAY-GGN-GGN-GGN, AAY-GGN-GGN-GGN-AAY-GGN-GGN, AAY-GGN-GGN-GGN-GGN-AAY-GGN, AAY-GGN-GGN-GGN-GGN-GGN-AAY, GGN-AAY-AAY-GGN-GGN-GGN-GGN, GGN-AAY-GGN-AAY-GGN-GGN-GGN, GGN-AAY-GGN-GGN-AAY-GGN-GGN, GGN-AAY-GGN-GGN-GGN-AAY-GGN, GGN-AAY-GGN-GGN-GGN-GGN-AAY, GGN-GGN-AAY-AAY-GGN-GGN-GGN, GGN-GGN-AAY-GGN-AAY-GGN-GGN, GGN-GGN-AAY-GGN-GGN-AAY-GGN, GGN-GGN-AAY-GGN-GGN-GGN-AAY, GGN-GGN-GGN-AAY-AAY-GGN-GGN, GGN-GGN-GGN-AAY-GGN-AAY-GGN, GGN-GGN-GGN-AAY-GGN-GGN-AAY, GGN-GGN-GGN-GGN-AAY-AAY-GGN, GGN-GGN-GGN-GGN-AAY-GGN-AAY-GGN-GGN-GGN-GGN-GGN-AAY, AAY-GGN-GGN-GGN-GGN-GGN-GGN, GGN-AAY-GGN-GGN-GGN-GGN-GGN, GGN-GGN-AAY-GGN-GGN-GGN-GGN, GGN-GGN-GGN-AAY-GGN-GGN-GGN, GGN-GGN-GGN-GGN-AAY-GGN-GGN, GGN-GGN-GGN-GGN-GGN-AAY-GGN |
| Oligonucleotides of peptide motifs containing 3-7 amino acide residues with G(glycine) as the major constituent and D(Aspartic Acid) as the minor constituent |
| GGN-GGN-GAY, GAY-GGN-GGN, GGN-GAY-GGN, GGN-GGN-GGN-GAY, GAY-GGN-GGN-GGN, GGN-GAY-GGN-GGN, GGN-GGN-GAY-GGN, GGN-GGN-GGN-GGN-GAY, GAY-GGN-GGN-GGN-GGN, GGN-GAY-GGN-GGN-GGN, GGN-GGN-GAY-GGN-GGN, GGN-GGN-GGN-GAY-GGN, GGN-GGN-GGN-GAY-GAY, GAY-GAY-GGN-GGN-GGN, GAY-GGN-GAY-GGN-GGN, GAY-GGN-GGN-GAY-GGN, GAY-GGN-GGN-GGN-GAY, GGN-GAY-GAY-GGN-GGN, GGN-GAY-GGN-GAY-GGN, GGN-GAY-GGN-GGN-GAY, GGN-GGN-GAY-GAY-GGN, GGN-GGN-GAY-GGN-GAY, GGN-GGN-GGN-GGN-GGN-GAY, GAY-GGN-GGN-GGN-GGN-GGN, GGN-GAY-GGN-GGN-GGN-GGN, GGN-GGN-GAY-GGN-GGN-GGN, GGN-GGN-GGN-GAY-GGN-GGN, GGN-GGN-GGN-GGN-GAY-GGN, GGN-GGN-GGN-GGN-GAY-GAY, GAY-GAY-GGN-GGN-GGN-GGN, GAY-GGN-GAY-GGN-GGN-GGN, GAY-GGN- |

TABLE 7-continued

| (SEQ ID NOS: 2482-4747, respectively, in order of appearance) |
|---|
| GGN-GAY-GGN-GGN, GAY-GGN-GGN-GGN-GAY-GGN, GAY-GGN-GGN-GGN-GGN-GAY, GGN-GAY-GAY-GGN-GGN-GGN, GGN-GAY-GGN-GAY-GGN-GGN, GGN-GAY-GGN-GGN-GAY-GGN, GGN-GAY-GGN-GGN-GGN-GAY, GGN-GGN-GAY-GAY-GGN-GGN, GGN-GGN-GAY-GGN-GAY-GGN, GGN-GGN-GAY-GGN-GGN-GAY, GGN-GGN-GGN-GAY-GAY-GGN, GGN-GGN-GGN-GAY-GGN-GAY, GGN-GGN-GGN-GGN-GAY-GAY-GAY, GAY-GAY-GAY-GGN-GGN-GGN-GGN, GAY-GGN-GAY-GAY-GGN-GGN-GGN, GAY-GGN-GAY-GGN-GAY-GGN-GGN, GAY-GGN-GAY-GGN-GGN-GAY-GGN, GAY-GGN-GAY-GGN-GGN-GGN-GAY, GAY-GGN-GGN-GAY-GAY-GGN-GGN, GAY-GGN-GGN-GAY-GGN-GAY-GGN, GAY-GGN-GGN-GAY-GGN-GGN-GAY, GAY-GGN-GGN-GGN-GAY-GGN-GAY, GAY-GGN-GGN-GGN-GAY-GAY-GGN, GAY-GGN-GGN-GGN-GGN-GAY-GAY, GAY-GAY-GGN-GAY-GGN-GGN-GGN, GAY-GAY-GGN-GGN-GAY-GGN-GGN, GAY-GAY-GGN-GGN-GGN-GAY-GGN, GAY-GAY-GGN-GGN-GGN-GGN-GAY, GGN-GAY-GAY-GAY-GGN-GGN-GGN, GGN-GAY-GAY-GGN-GAY-GGN-GGN, GGN-GAY-GAY-GGN-GGN-GAY-GGN, GGN-GAY-GAY-GGN-GGN-GGN-GAY, GGN-GAY-GGN-GAY-GAY-GGN-GGN, GGN-GAY-GGN-GGN-GAY-GAY-GGN, GGN-GAY-GGN-GGN-GGN-GAY-GAY, GGN-GAY-GGN-GAY-GGN-GAY-GGN, GGN-GAY-GGN-GAY-GGN-GGN-GAY, GGN-GAY-GGN-GGN-GAY-GGN-GAY, GGN-GGN-GAY-GAY-GAY-GGN-GGN, GGN-GGN-GAY-GAY-GGN-GAY-GGN, GGN-GGN-GAY-GAY-GGN-GGN-GAY, GGN-GGN-GAY-GGN-GAY-GAY-GGN, GGN-GGN-GAY-GGN-GAY-GGN-GAY, GGN-GGN-GAY-GGN-GGN-GAY-GAY, GGN-GGN-GGN-GAY-GAY-GAY-GGN, GGN-GGN-GGN-GAY-GAY-GGN-GAY, GGN-GGN-GGN-GAY-GGN-GAY-GAY, GGN-GGN-GGN-GGN-GGN-GAY-GAY, GAY-GAY-GGN-GGN-GGN-GGN-GGN, GAY-GGN-GAY-GGN-GGN-GGN-GGN, GAY-GGN-GGN-GAY-GGN-GGN-GGN, GAY-GGN-GGN-GGN-GAY-GGN-GGN, GAY-GGN-GGN-GGN-GGN-GAY-GGN, GAY-GGN-GGN-GGN-GGN-GGN-GAY, GGN-GAY-GAY-GGN-GGN-GGN-GGN, GGN-GAY-GGN-GAY-GGN-GGN-GGN, GGN-GAY-GGN-GGN-GAY-GGN-GGN, GGN-GAY-GGN-GGN-GGN-GAY-GGN, GGN-GAY-GGN-GGN-GGN-GGN-GAY, GGN-GGN-GAY-GAY-GGN-GGN-GGN, GGN-GGN-GAY-GGN-GAY-GGN-GGN, GGN-GGN-GAY-GGN-GGN-GAY-GGN, GGN-GGN-GAY-GGN-GGN-GGN-GAY, GGN-GGN-GGN-GAY-GAY-GGN-GGN, GGN-GGN-GGN-GAY-GGN-GAY-GGN, GGN-GGN-GGN-GAY-GGN-GGN-GAY, GGN-GGN-GGN-GGN-GAY-GAY-GGN, GGN- |

TABLE 7-continued

| (SEQ ID NOS: 2482-4747, respectively, in order of appearance) |
|---|
| GGN-GGN-GGN-GAY-GGN-GAY-GGN-GGN-GGN-GGN-GGN-GGN-GAY, GAY-GGN-GGN-GGN-GGN-GGN-GGN, GGN-GAY-GGN-GGN-GGN-GGN-GGN, GGN-GGN-GAY-GGN-GGN-GGN-GGN, GGN-GGN-GGN-GAY-GGN-GGN-GGN, GGN-GGN-GGN-GGN-GAY-GGN-GGN, GGN-GGN-GGN-GGN-GGN-GAY-GGN |
| Q (glutamine) as major constituent Oligonucleotides of peptide motifs containing 3-7 amino acide residues with Q(Glutamine) as the major constituent and T(Threonine) as the minor constituent |
| CAR-CAR-ACN, ACN-CAR-CAR, CAR-ACN-CAR, CAR-CAR-CAR-ACN, ACN-CAR-CAR-CAR, CAR-ACN-CAR-CAR, CAR-CAR-ACN-CAR, CAR-CAR-CAR-CAR-ACN, ACN-CAR-CAR-CAR-CAR, CAR-ACN-CAR-CAR-CAR, CAR-CAR-ACN-CAR-CAR, CAR-CAR-CAR-ACN-CAR, CAR-CAR-CAR-ACN-ACN, ACN-ACN-CAR-CAR-CAR, ACN-CAR-ACN-CAR-CAR, ACN-CAR-CAR-ACN-CAR, ACN-CAR-CAR-CAR-ACN, CAR-ACN-ACN-CAR-CAR, CAR-ACN-CAR-ACN-CAR, CAR-ACN-CAR-CAR-ACN, CAR-CAR-ACN-ACN-CAR, CAR-CAR-ACN-CAR-ACN, CAR-CAR-CAR-CAR-CAR-ACN, ACN-CAR-CAR-CAR-CAR-CAR, CAR-ACN-CAR-CAR-CAR-CAR, CAR-CAR-ACN-CAR-CAR-CAR, CAR-CAR-CAR-ACN-CAR-CAR, CAR-CAR-CAR-CAR-ACN-CAR, CAR-CAR-CAR-CAR-ACN-ACN, ACN-ACN-CAR-CAR-CAR-CAR, ACN-CAR-ACN-CAR-CAR-CAR, ACN-CAR-CAR-ACN-CAR-CAR, ACN-CAR-CAR-CAR-ACN-CAR, ACN-CAR-CAR-CAR-CAR-ACN, CAR-ACN-ACN-CAR-CAR-CAR, CAR-ACN-CAR-ACN-CAR-CAR, CAR-ACN-CAR-CAR-ACN-CAR, CAR-ACN-CAR-CAR-CAR-ACN, CAR-CAR-ACN-ACN-CAR-CAR, CAR-CAR-ACN-CAR-ACN-CAR, CAR-CAR-ACN-CAR-CAR-ACN, CAR-CAR-CAR-ACN-ACN-CAR, CAR-CAR-CAR-ACN-CAR-ACN, CAR-CAR-CAR-CAR-ACN-ACN-ACN, ACN-ACN-ACN-CAR-CAR-CAR-CAR, ACN-CAR-ACN-ACN-CAR-CAR-CAR, ACN-CAR-ACN-CAR-ACN-CAR-CAR, ACN-CAR-ACN-CAR-CAR-ACN-CAR, ACN-CAR-ACN-CAR-CAR-CAR-ACN, ACN-CAR-CAR-ACN-ACN-CAR-CAR, ACN-CAR-CAR-ACN-CAR-ACN-CAR, ACN-CAR-CAR-ACN-CAR-CAR-ACN, ACN-CAR-CAR-CAR-ACN-CAR-ACN, ACN-CAR-CAR-CAR-ACN-ACN-CAR, ACN-CAR-CAR-CAR-CAR-ACN-ACN, ACN-ACN-CAR-ACN-CAR-CAR-CAR, ACN-ACN-CAR-CAR-ACN-CAR-CAR, ACN-ACN-CAR-CAR-CAR-ACN-CAR, ACN-ACN-CAR-CAR-CAR-CAR-ACN, CAR-ACN-ACN-ACN-CAR-CAR-CAR, CAR-ACN-ACN-CAR-ACN-CAR-CAR, CAR-ACN-ACN-CAR-CAR-ACN-CAR, CAR- |

TABLE 7-continued (SEQ ID NOS: 2482-4747, respectively, in order of appearance)

ACN-ACN-CAR-CAR-CAR-ACN, CAR-ACN-CAR-ACN-ACN-CAR-
CAR, CAR-ACN-CAR-CAR-ACN-ACN-CAR, CAR-ACN-CAR-CAR-
CAR-ACN-ACN, CAR-ACN-CAR-ACN-CAR-ACN-CAR, CAR-ACN-
CAR-ACN-CAR-CAR-ACN, CAR-ACN-CAR-CAR-ACN-CAR-ACN,
CAR-CAR-ACN-ACN-ACN-CAR-CAR, CAR-CAR-ACN-ACN-CAR-
ACN-CAR, CAR-CAR-ACN-ACN-CAR-CAR-ACN, CAR-CAR-ACN-
CAR-ACN-ACN-CAR, CAR-CAR-ACN-CAR-ACN-CAR-ACN, CAR-
CAR-ACN-CAR-CAR-ACN-ACN, CAR-CAR-CAR-ACN-ACN-ACN-
CAR, CAR-CAR-CAR-ACN-ACN-CAR-ACN, CAR-CAR-CAR-ACN-
CAR-ACN-ACN, CAR-CAR-CAR-CAR-CAR-ACN-ACN, ACN-ACN-
CAR-CAR-CAR-CAR-CAR, ACN-CAR-ACN-CAR-CAR-CAR-CAR,
ACN-CAR-CAR-ACN-CAR-CAR-CAR, ACN-CAR-CAR-CAR-ACN-
CAR-CAR, ACN-CAR-CAR-CAR-CAR-ACN-CAR, ACN-CAR-CAR-
CAR-CAR-CAR-ACN, CAR-ACN-ACN-CAR-CAR-CAR-CAR, CAR-
ACN-CAR-ACN-CAR-CAR-CAR, CAR-ACN-CAR-CAR-ACN-CAR-
CAR, CAR-ACN-CAR-CAR-CAR-ACN-CAR, CAR-ACN-CAR-CAR-
CAR-CAR-ACN, CAR-CAR-ACN-ACN-CAR-CAR-CAR, CAR-CAR-
ACN-CAR-ACN-CAR-CAR, CAR-CAR-ACN-CAR-CAR-ACN-CAR,
CAR-CAR-ACN-CAR-CAR-CAR-ACN, CAR-CAR-CAR-ACN-ACN-
CAR-CAR, CAR-CAR-CAR-ACN-CAR-ACN-CAR, CAR-CAR-CAR-
ACN-CAR-CAR-ACN, CAR-CAR-CAR-CAR-ACN-ACN-CAR, CAR-
CAR-CAR-CAR-ACN-CAR-ACN-CAR-CAR-CAR-CAR-CAR-CAR-
ACN,
ACN-CAR-CAR-CAR-CAR-CAR-CAR, CAR-ACN-CAR-CAR-CAR-
CAR-CAR, CAR-CAR-ACN-CAR-CAR-CAR-CAR, CAR-CAR-CAR-
ACN-CAR-CAR-CAR, CAR-CAR-CAR-CAR-ACN-CAR-CAR, CAR-
CAR-CAR-CAR-CAR-ACN-CAR

Oligonucleotides of peptide motifs containing 3-7 amino acide residues with Q(Glutamine) as the major constituent and A(Alanine) as the minor constituent CAR-CAR-GCN, GCN-CAR-CAR, CAR-GCN-CAR, CAR-CAR-CAR-
GCN, GCN-CAR-CAR-CAR, CAR-GCN-CAR-CAR, CAR-CAR-GCN-
CAR, CAR-CAR-CAR-CAR-GCN, GCN-CAR-CAR-CAR-CAR, CAR-
GCN-CAR-CAR-CAR, CAR-CAR-GCN-CAR-CAR, CAR-CAR-CAR-
GCN-CAR, CAR-CAR-CAR-GCN-GCN, GCN-GCN-CAR-CAR-CAR,
GCN-CAR-GCN-CAR-CAR, GCN-CAR-CAR-GCN-CAR, GCN-CAR-
CAR-CAR-GCN, CAR-GCN-GCN-CAR-CAR, CAR-GCN-CAR-GCN-
CAR, CAR-GCN-CAR-CAR-GCN, CAR-CAR-GCN-GCN-CAR, CAR-
CAR-GCN-CAR-GCN, CAR-CAR-CAR-CAR-CAR-GCN, GCN-CAR-
CAR-CAR-CAR, CAR-GCN-CAR-CAR-CAR-CAR, CAR-CAR-
GCN-CAR-CAR-CAR, CAR-CAR-CAR-GCN-CAR-CAR, CAR-CAR-
CAR-CAR-GCN-CAR, CAR-CAR-CAR-CAR-GCN-GCN, GCN-GCN-
CAR-CAR-CAR-CAR, GCN-CAR-GCN-CAR-CAR-CAR, GCN-CAR-
CAR-GCN-CAR-CAR, GCN-CAR-CAR-CAR-GCN-CAR, GCN-CAR-
CAR-CAR-CAR-GCN, CAR-GCN-GCN-CAR-CAR-CAR, CAR-GCN-
CAR-GCN-CAR-CAR, CAR-GCN-CAR-CAR-GCN-CAR, CAR-GCN-
CAR-CAR-CAR-GCN, CAR-CAR-GCN-GCN-CAR-CAR, CAR-CAR-
GCN-CAR-GCN-CAR, CAR-CAR-GCN-CAR-CAR-GCN, CAR-CAR-
CAR-GCN-GCN-CAR, CAR-CAR-CAR-GCN-CAR-GCN, CAR-CAR-
CAR-CAR-GCN-GCN-GCN, GCN-GCN-GCN-CAR-CAR-CAR-CAR,
GCN-CAR-GCN-GCN-CAR-CAR-CAR, GCN-CAR-GCN-CAR-GCN-
CAR-CAR, GCN-CAR-GCN-CAR-CAR-GCN-CAR, GCN-CAR-GCN-
CAR-CAR-CAR-GCN, GCN-CAR-CAR-GCN-GCN-CAR-CAR, GCN-
CAR-CAR-GCN-CAR-GCN-CAR, GCN-CAR-CAR-GCN-CAR-CAR-
GCN, GCN-CAR-CAR-CAR-GCN-CAR-GCN, GCN-CAR-CAR-CAR-
GCN-GCN-CAR, GCN-CAR-CAR-CAR-CAR-GCN-GCN, GCN-GCN-
CAR-GCN-CAR-CAR-CAR, GCN-GCN-CAR-CAR-GCN-CAR-CAR,
GCN-GCN-CAR-CAR-CAR-GCN-CAR, GCN-GCN-CAR-CAR-CAR-
CAR-GCN, CAR-GCN-GCN-GCN-CAR-CAR-CAR, CAR-GCN-GCN-
CAR-GCN-CAR-CAR, CAR-GCN-GCN-CAR-CAR-GCN-CAR, CAR-
GCN-GCN-CAR-CAR-CAR-GCN, CAR-GCN-CAR-GCN-GCN-CAR-
CAR, CAR-GCN-CAR-CAR-GCN-GCN-CAR, CAR-GCN-CAR-CAR-
CAR-GCN-GCN, CAR-GCN-CAR-GCN-CAR-GCN-CAR, CAR-GCN-
CAR-GCN-CAR-CAR-GCN, CAR-GCN-CAR-CAR-GCN-CAR-GCN,
CAR-CAR-GCN-GCN-GCN-CAR-CAR, CAR-CAR-GCN-GCN-CAR-
GCN-CAR, CAR-CAR-GCN-GCN-CAR-CAR-GCN, CAR-CAR-GCN-
CAR-GCN-GCN-CAR, CAR-CAR-GCN-CAR-GCN-CAR-GCN, CAR-
CAR-GCN-CAR-CAR-GCN-GCN, CAR-CAR-CAR-GCN-GCN-GCN-
CAR, CAR-CAR-CAR-GCN-GCN-CAR-GCN, CAR-CAR-CAR-GCN-
GCAR-GCN-GCN, CAR-CAR-CAR-CAR-CAR-CN-GCN, GCN-GCN-
CAR-CAR-CAR-CAR-CAR, GCN-CAR-GCN-CAR-CAR-CAR-CAR,
GCN-CAR-CAR-GCN-CAR-CAR-CAR, GCN-CAR-CAR-CAR-GCN-
CAR-CAR, GCN-CAR-CAR-CAR-CAR-GCN-CAR, GCN-CAR-CAR-
CAR-CAR-CAR-GCN, CAR-GCN-GCN-CAR-CAR-CAR-CAR, CAR-
GCN-CAR-GCN-CAR-CAR-CAR, CAR-GCN-CAR-CAR-GCN-CAR-
CAR, CAR-GCN-CAR-CAR-CAR-GCN-CAR, CAR-GCN-CAR-CAR-
CAR-CAR-GCN, CAR-CAR-GCN-GCN-CAR-CAR-CAR, CAR-CAR- TABLE 7-continued (SEQ ID NOS: 2482-4747, respectively, in order of appearance)

GCN-CAR-GCN-CAR-CAR, CAR-CAR-GCN-CAR-CAR-GCN-CAR, CAR-CAR-GCN-CAR-CAR-CAR-GCN, CAR-CAR-CAR-GCN-GCN-CAR-CAR, CAR-CAR-CAR-GCN-CAR-GCN-CAR, CAR-CAR-CAR-GCN-CAR-CAR-GCN, CAR-CAR-CAR-CAR-GCN-GCN-CAR, CAR-CAR-CAR-CAR-GCN-CAR-GCN-CAR-CAR-CAR-CAR-CAR-CAR-GCN,

GCN-CAR-CAR-CAR-CAR-CAR-CAR, CAR-GCN-CAR-CAR-CAR-CAR-CAR, CAR-CAR-GCN-CAR-CAR-CAR-CAR, CAR-CAR-CAR-GCN-CAR-CAR-CAR, CAR-CAR-CAR-CAR-GCN-CAR-CAR, CAR-CAR-CAR-CAR-CAR-GCN-CAR

Oligonucleotides of peptide motifs containing 3-7 amino acide residues with Q(Glutamine) as the major constituent and S(Serine) as the minor constituent CAR-CAR-AGY, AGY-CAR-CAR, CAR-AGY-CAR, CAR-CAR-CAR-AGY, AGY-CAR-CAR-CAR, CAR-AGY-CAR-CAR, CAR-CAR-AGY-CAR, CAR-CAR-CAR-CAR-AGY, AGY-CAR-CAR-CAR-CAR, CAR-AGY-CAR-CAR-CAR, CAR-CAR-AGY-CAR-CAR, CAR-CAR-CAR-AGY-CAR, CAR-CAR-CAR-AGY-AGY, AGY-AGY-CAR-CAR-CAR, AGY-CAR-AGY-CAR-CAR, AGY-CAR-CAR-AGY-CAR, AGY-CAR-CAR-CAR-AGY, CAR-AGY-AGY-CAR-CAR, CAR-AGY-CAR-AGY-CAR, CAR-AGY-CAR-CAR-AGY, CAR-CAR-AGY-AGY-CAR, CAR-CAR-AGY-CAR-AGY, CAR-CAR-CAR-CAR-CAR-AGY, AGY-CAR-CAR-CAR-CAR-CAR, CAR-AGY-CAR-CAR-CAR-CAR, CAR-CAR-AGY-CAR-CAR-CAR, CAR-CAR-CAR-AGY-CAR-CAR, CAR-CAR-CAR-CAR-AGY-CAR, CAR-CAR-CAR-CAR-AGY-AGY, AGY-AGY-CAR-CAR-CAR-CAR, AGY-CAR-AGY-CAR-CAR-CAR, AGY-CAR-CAR-AGY-CAR-CAR, AGY-CAR-CAR-CAR-AGY-CAR, AGY-CAR-CAR-CAR-CAR-AGY, CAR-AGY-AGY-CAR-CAR-CAR, CAR-AGY-CAR-AGY-CAR-CAR, CAR-AGY-CAR-CAR-AGY-CAR, CAR-AGY-CAR-CAR-CAR-AGY, CAR-CAR-AGY-AGY-CAR-CAR, CAR-CAR-AGY-CAR-AGY-CAR, CAR-CAR-AGY-CAR-CAR-AGY, CAR-CAR-CAR-AGY-AGY-CAR, CAR-CAR-CAR-AGY-CAR-AGY, CAR-CAR-CAR-AGY-AGY-AGY, AGY-AGY-AGY-CAR-CAR-CAR-CAR, AGY-CAR-AGY-AGY-CAR-CAR-CAR, AGY-CAR-AGY-CAR-AGY-CAR-CAR, AGY-CAR-AGY-CAR-CAR-AGY-CAR, AGY-CAR-AGY-CAR-CAR-CAR-AGY, AGY-CAR-CAR-AGY-AGY-CAR-CAR, AGY-CAR-CAR-AGY-CAR-AGY-CAR, AGY-CAR-CAR-AGY-CAR-CAR-AGY, AGY-CAR-CAR-CAR-AGY-CAR-AGY, AGY-CAR-CAR-CAR-AGY-AGY-CAR, AGY-CAR-CAR-CAR-CAR-AGY-AGY, AGY-AGY-CAR-AGY-CAR-CAR-CAR, AGY-AGY-CAR-CAR-AGY-CAR-CAR, AGY-AGY-CAR-CAR-CAR-AGY-CAR, AGY-AGY-CAR-CAR-CAR-CAR-AGY, CAR-AGY-AGY-AGY-CAR-CAR-CAR, CAR-AGY-AGY-CAR-AGY-CAR-CAR, CAR-AGY-AGY-CAR-CAR-AGY-CAR, CAR-AGY-AGY-CAR-CAR-CAR-AGY, CAR-AGY-CAR-AGY-AGY-CAR-CAR, CAR-AGY-CAR-CAR-AGY-AGY-CAR, CAR-AGY-CAR-CAR-AGY-AGY, CAR-AGY-CAR-AGY-CAR-AGY-CAR, CAR-AGY-CAR-AGY-CAR-CAR-AGY, CAR-AGY-CAR-CAR-AGY-CAR-AGY, CAR-CAR-AGY-AGY-AGY-CAR-CAR, CAR-CAR-AGY-AGY-CAR-AGY-CAR, CAR-CAR-AGY-AGY-CAR-CAR-AGY, CAR-CAR-AGY-CAR-AGY-AGY-CAR, CAR-CAR-AGY-CAR-AGY-CAR-AGY, CAR-CAR-AGY-CAR-CAR-AGY-AGY, CAR-CAR-CAR-AGY-AGY-AGY-CAR, CAR-CAR-CAR-AGY-AGY-CAR-AGY, CAR-CAR-CAR-AGY-CAR-AGY-AGY, CAR-CAR-CAR-CAR-CAR-AGY-AGY, AGY-AGY-CAR-CAR-CAR-CAR-CAR, AGY-CAR-AGY-CAR-CAR-CAR-CAR, AGY-CAR-CAR-AGY-CAR-CAR-CAR, AGY-CAR-CAR-CAR-AGY-CAR-CAR, AGY-CAR-CAR-CAR-CAR-AGY-CAR, AGY-CAR-CAR-CAR-CAR-CAR-AGY, CAR-AGY-AGY-CAR-CAR-CAR-CAR, CAR-AGY-CAR-AGY-CAR-CAR-CAR, CAR-AGY-CAR-CAR-AGY-CAR-CAR, CAR-AGY-CAR-CAR-CAR-AGY-CAR, CAR-AGY-CAR-CAR-CAR-CAR-AGY, CAR-CAR-AGY-AGY-CAR-CAR-CAR, CAR-CAR-AGY-CAR-AGY-CAR-CAR, CAR-CAR-AGY-CAR-CAR-AGY-CAR, CAR-CAR-AGY-CAR-CAR-CAR-AGY, CAR-CAR-CAR-AGY-AGY-CAR-CAR, CAR-CAR-CAR-AGY-CAR-AGY-CAR, CAR-CAR-CAR-AGY-CAR-CAR-AGY, CAR-CAR-CAR-CAR-AGY-AGY-CAR, CAR-CAR-CAR-CAR-AGY-CAR-AGY-CAR-CAR-CAR-CAR-CAR-CAR-AGY, AGY-CAR-CAR-CAR-CAR-CAR-CAR, CAR-AGY-CAR-CAR-CAR-CAR-CAR, CAR-CAR-AGY-CAR-CAR-CAR-CAR, CAR-CAR-CAR-AGY-CAR-CAR-CAR, CAR-CAR-CAR-CAR-AGY-CAR-CAR, CAR-CAR-CAR-CAR-CAR-AGY-CAR Oligonucleotides of peptide motifs containing 3-7 amino acide residues with Q(Glutamine) as the major constituent and E(Glutamic Acid) as the minor constituent CAR-CAR-GAR, GAR-CAR-CAR, CAR-GAR-CAR, CAR-CAR-CAR-GAR, GAR-CAR-CAR-CAR, CAR-GAR-CAR-CAR, CAR-CAR-GAR-CAR, CAR-CAR-CAR-CAR-GAR, GAR-CAR-CAR-CAR-CAR, CAR-GAR-CAR-CAR-CAR, CAR-CAR-GAR-CAR-CAR, CAR-CAR-CAR-GAR-CAR, CAR-CAR-CAR-GAR-GAR, GAR-GAR-CAR-CAR-CAR, GAR-CAR-GAR-CAR-CAR, GAR-CAR-CAR-GAR-CAR, GAR-CAR- TABLE 7-continued (SEQ ID NOS: 2482-4747, respectively, in order of appearance)

CAR-CAR-GAR, CAR-GAR-GAR-CAR-CAR, CAR-GAR-CAR-GAR-CAR, CAR-GAR-CAR-CAR-GAR, CAR-CAR-GAR-GAR-CAR, CAR-CAR-GAR-CAR-GAR, CAR-CAR-CAR-CAR-CAR-GAR, GAR-CAR-CAR-CAR-CAR-CAR, CAR-GAR-CAR-CAR-CAR-CAR, CAR-CAR-GAR-CAR-CAR-CAR, CAR-CAR-CAR-GAR-CAR-CAR, CAR-CAR-CAR-CAR-GAR-CAR, CAR-CAR-CAR-CAR-GAR-GAR, GAR-GAR-CAR-CAR-CAR-CAR, GAR-CAR-GAR-CAR-CAR-CAR, GAR-CAR-CAR-GAR-CAR-CAR, GAR-CAR-CAR-CAR-GAR-CAR, GAR-CAR-CAR-CAR-CAR-GAR, CAR-GAR-GAR-CAR-CAR-CAR, CAR-GAR-CAR-GAR-CAR-CAR, CAR-GAR-CAR-CAR-GAR-CAR, CAR-GAR-CAR-CAR-CAR-GAR, CAR-CAR-GAR-GAR-CAR-CAR, CAR-CAR-GAR-CAR-GAR-CAR, CAR-CAR-GAR-CAR-CAR-GAR, CAR-CAR-CAR-GAR-GAR-CAR, CAR-CAR-CAR-GAR-CAR-GAR, CAR-CAR-CAR-CAR-GAR-GAR-GAR, GAR-GAR-GAR-CAR-CAR-CAR-CAR, GAR-CAR-GAR-GAR-CAR-CAR-CAR, GAR-CAR-GAR-CAR-GAR-CAR-CAR, GAR-CAR-GAR-CAR-CAR-GAR-CAR, GAR-CAR-GAR-CAR-CAR-CAR-GAR, GAR-CAR-CAR-GAR-GAR-CAR-CAR, GAR-CAR-CAR-GAR-CAR-GAR-CAR, GAR-CAR-CAR-GAR-CAR-CAR-GAR, GAR-CAR-CAR-CAR-GAR-CAR-GAR, GAR-CAR-CAR-CAR-GAR-GAR-CAR, GAR-CAR-CAR-CAR-CAR-GAR-GAR, GAR-GAR-CAR-GAR-CAR-CAR-CAR, GAR-GAR-CAR-CAR-GAR-CAR-CAR, GAR-GAR-CAR-CAR-CAR-GAR-CAR, GAR-GAR-CAR-CAR-CAR-CAR-GAR, CAR-GAR-GAR-GAR-CAR-CAR-CAR, CAR-GAR-GAR-CAR-GAR-CAR-CAR, CAR-GAR-GAR-CAR-CAR-GAR-CAR, CAR-GAR-GAR-CAR-CAR-CAR-GAR, CAR-GAR-CAR-GAR-GAR-CAR-CAR, CAR-GAR-CAR-CAR-GAR-GAR-CAR, CAR-GAR-CAR-CAR-CAR-GAR-GAR, CAR-GAR-CAR-GAR-CAR-GAR-CAR, CAR-GAR-CAR-GAR-CAR-CAR-GAR, CAR-GAR-CAR-CAR-GAR-CAR-GAR, CAR-CAR-GAR-GAR-GAR-CAR-CAR, CAR-CAR-GAR-GAR-CAR-GAR-CAR, CAR-CAR-GAR-GAR-CAR-CAR-GAR, CAR-CAR-GAR-CAR-GAR-GAR-CAR, CAR-CAR-GAR-CAR-GAR-CAR-GAR, CAR-CAR-GAR-CAR-CAR-GAR-GAR, CAR-CAR-CAR-GAR-GAR-GAR-CAR, CAR-CAR-CAR-GAR-GAR-CAR-GAR, CAR-CAR-CAR-GAR-CAR-GAR-GAR, CAR-CAR-CAR-CAR-CAR-GAR-GAR, GAR-GAR-CAR-CAR-CAR-CAR-CAR, GAR-CAR-GAR-CAR-CAR-CAR-CAR, GAR-CAR-CAR-GAR-CAR-CAR-CAR, GAR-CAR-CAR-CAR-GAR-CAR-CAR, GAR-CAR-CAR-CAR-CAR-GAR-CAR, GAR-CAR-CAR-CAR-CAR-CAR-GAR, CAR-GAR-GAR-CAR-CAR-CAR-CAR, CAR-GAR-GAR-CAR-CAR-CAR-GAR-CAR, CAR-GAR-CAR-GAR-CAR-CAR-CAR, CAR-GAR-CAR-CAR-GAR-CAR-CAR, CAR-GAR-CAR-CAR-CAR-GAR-CAR, CAR-GAR-CAR-CAR-CAR-CAR-GAR, CAR-CAR-GAR-GAR-CAR-CAR-CAR, CAR-CAR-GAR-CAR-GAR-CAR-CAR, CAR-CAR-GAR-CAR-CAR-GAR-CAR, CAR-CAR-GAR-CAR-CAR-CAR-GAR, CAR-CAR-CAR-GAR-GAR-CAR-CAR, CAR-CAR-CAR-GAR-CAR-GAR-CAR, CAR-CAR-CAR-GAR-CAR-CAR-GAR, CAR-CAR-CAR-CAR-GAR-GAR-CAR, CAR-CAR-CAR-CAR-GAR-CAR-GAR, CAR-CAR-CAR-CAR-CAR-GAR-GAR,

GAR-CAR-CAR-CAR-CAR-CAR-CAR, CAR-GAR-CAR-CAR-CAR-CAR-CAR, CAR-CAR-GAR-CAR-CAR-CAR-CAR, CAR-CAR-CAR-GAR-CAR-CAR-CAR, CAR-CAR-CAR-CAR-GAR-CAR-CAR, CAR-CAR-CAR-CAR-CAR-GAR-CAR

Oligonucleotides of peptide motifs containing 3-7 amino acide residues with Q(Glutamine) as the major constituent and H(Histidine) as the minor constituent CAR-CAR-CAY, CAY-CAR-CAR, CAR-CAY-CAR, CAR-CAR-CAR-CAY, CAY-CAR-CAR-CAR, CAR-CAY-CAR-CAR, CAR-CAR-CAY-CAR, CAR-CAR-CAR-CAR-CAY, CAY-CAR-CAR-CAR-CAR, CAR-CAY-CAR-CAR-CAR, CAR-CAR-CAY-CAR-CAR, CAR-CAR-CAR-CAY-CAR, CAR-CAR-CAR-CAY-CAY, CAY-CAY-CAR-CAR-CAR, CAY-CAR-CAY-CAR-CAR, CAY-CAR-CAR-CAY-CAR, CAY-CAR-CAR-CAR-CAY, CAR-CAY-CAY-CAR-CAR, CAR-CAY-CAR-CAY-CAR, CAR-CAY-CAR-CAR-CAY, CAR-CAR-CAY-CAY-CAR, CAR-CAR-CAY-CAR-CAY, CAR-CAR-CAR-CAR-CAR-CAY, CAY-CAR-CAR-CAR-CAR-CAR, CAR-CAY-CAR-CAR-CAR-CAR, CAR-CAR-CAY-CAR-CAR-CAR, CAR-CAR-CAR-CAY-CAR-CAR, CAR-CAR-CAR-CAR-CAY-CAR, CAR-CAR-CAR-CAR-CAY-CAY, CAY-CAY-CAR-CAR-CAR-CAR, CAY-CAR-CAY-CAR-CAR-CAR, CAY-CAR-CAR-CAY-CAR-CAR, CAY-CAR-CAR-CAR-CAY-CAR, CAY-CAR-CAR-CAR-CAR-CAY, CAR-CAY-CAY-CAR-CAR-CAR, CAR-CAY-CAR-CAY-CAR-CAR, CAR-CAY-CAR-CAR-CAY-CAR, CAR-CAY-CAR-CAR-CAR-CAY, CAR-CAR-CAY-CAY-CAR-CAR, CAR-CAR-CAY-CAR-CAY-CAR, CAR-CAR-CAY-CAR-CAR-CAY, CAR-CAR-CAR-CAY-CAY-CAR, CAR-CAR-CAR-CAY-CAR-CAY, CAR-CAR-CAR-CAR-CAY-CAY-CAY, CAY-CAY-CAY-CAR-CAR-CAR-CAR, CAY-CAR-CAY-CAY-CAR-CAR-CAR, CAY-CAR-CAY-CAR-CAY-CAR-CAR, CAY-CAR-CAY-CAR-CAR-CAY-CAR, CAY-CAR-CAY-CAR-CAR-CAR-CAY, CAY-CAR-CAR-CAY-CAY-CAR-CAR, CAY- TABLE 7-continued (SEQ ID NOS: 2482-4747, respectively, in order of appearance)

CAR-CAR-CAY-CAR-CAY-CAR, CAY-CAR-CAR-CAY-CAR-CAR-CAY, CAY-CAR-CAR-CAR-CAY-CAR-CAY, CAY-CAR-CAR-CAY-CAY-CAR, CAY-CAR-CAR-CAR-CAR-CAY-CAY, CAY-CAY-CAR-CAY-CAR-CAR-CAR, CAY-CAY-CAR-CAR-CAY-CAR-CAR, CAY-CAY-CAR-CAR-CAR-CAY-CAR, CAY-CAY-CAR-CAR-CAR-CAY, CAR-CAY-CAY-CAY-CAR-CAR-CAR, CAR-CAY-CAY-CAR-CAY-CAR-CAR, CAR-CAY-CAY-CAR-CAR-CAY-CAR, CAR-CAY-CAY-CAR-CAR-CAR-CAY, CAR-CAY-CAR-CAY-CAY-CAR-CAR, CAR-CAY-CAR-CAR-CAY-CAY-CAR, CAR-CAY-CAR-CAR-CAY-CAY, CAR-CAY-CAR-CAY-CAR-CAY-CAR, CAR-CAY-CAR-CAY-CAR-CAR-CAY, CAR-CAY-CAR-CAR-CAY-CAR-CAY, CAR-CAR-CAY-CAY-CAY-CAR-CAR, CAR-CAR-CAY-CAY-CAR-CAY-CAR, CAR-CAR-CAY-CAY-CAR-CAR-CAY, CAR-CAR-CAY-CAR-CAY-CAY-CAR, CAR-CAR-CAY-CAR-CAY-CAR-CAY, CAR-CAR-CAY-CAR-CAR-CAY-CAY, CAR-CAR-CAR-CAY-CAY-CAY-CAR, CAR-CAR-CAR-CAY-CAY-CAR-CAY, CAR-CAR-CAY-CAR-CAY-CAY, CAR-CAR-CAR-CAR-CAR-CAY-CAY, CAY-CAY-CAR-CAR-CAR-CAR-CAR, CAY-CAR-CAY-CAR-CAR-CAR-CAR, CAY-CAR-CAR-CAY-CAR-CAR-CAR, CAY-CAR-CAR-CAR-CAY-CAR-CAR, CAY-CAR-CAR-CAR-CAR-CAY-CAR, CAY-CAR-CAR-CAR-CAR-CAR-CAY, CAR-CAY-CAY-CAR-CAR-CAR-CAR, CAR-CAY-CAR-CAY-CAR-CAR-CAR, CAR-CAY-CAR-CAR-CAY-CAR-CAR, CAR-CAY-CAR-CAR-CAR-CAY-CAR, CAR-CAY-CAR-CAR-CAR-CAR-CAY, CAR-CAR-CAY-CAY-CAR-CAR-CAR, CAR-CAR-CAY-CAR-CAY-CAR-CAR, CAR-CAR-CAY-CAR-CAR-CAY-CAR, CAR-CAR-CAY-CAR-CAR-CAR-CAY, CAR-CAR-CAR-CAY-CAY-CAR-CAR, CAR-CAR-CAR-CAY-CAR-CAY-CAR, CAR-CAR-CAR-CAY-CAR-CAR-CAY, CAR-CAR-CAR-CAR-CAY-CAY-CAR, CAR-CAR-CAR-CAR-CAY-CAR-CAY-CAR-CAR-CAR-CAR-CAR-CAR-CAY,
CAY-CAR-CAR-CAR-CAR-CAR-CAR, CAR-CAY-CAR-CAR-CAR-CAR-CAR, CAR-CAR-CAY-CAR-CAR-CAR-CAR, CAR-CAR-CAR-CAY-CAR-CAR-CAR, CAR-CAR-CAR-CAR-CAY-CAR-CAR, CAR-CAR-CAR-CAR-CAR-CAY-CAR

Oligonucleotides of peptide motifs containing 3-7 amino acide residues with Q(Glutamine) as the major constituent and N(Asparagine) as the minor constituent CAR-CAR-AAY, AAY-CAR-CAR, CAR-AAY-CAR, CAR-CAR-CAR-AAY, AAY-CAR-CAR-CAR, CAR-AAY-CAR-CAR, CAR-CAR-AAY-CAR, CAR-CAR-CAR-CAR-AAY, AAY-CAR-CAR-CAR-CAR, CAR-AAY-CAR-CAR-CAR, CAR-CAR-AAY-CAR-CAR, CAR-CAR-CAR-AAY-CAR, CAR-CAR-CAR-AAY-AAY, AAY-AAY-CAR-CAR-CAR, AAY-CAR-AAY-CAR-CAR, AAY-CAR-CAR-AAY-CAR, AAY-CAR-CAR-CAR-AAY, CAR-AAY-AAY-CAR-CAR, CAR-AAY-CAR-AAY-CAR, CAR-AAY-CAR-CAR-AAY, CAR-CAR-AAY-AAY-CAR, CAR-CAR-AAY-CAR-AAY, CAR-CAR-CAR-CAR-CAR-AAY, AAY-CAR-CAR-CAR-CAR-CAR, CAR-AAY-CAR-CAR-CAR-CAR, CAR-CAR-AAY-CAR-CAR-CAR, CAR-CAR-CAR-AAY-CAR-CAR, CAR-CAR-CAR-CAR-AAY-CAR, CAR-CAR-CAR-CAR-AAY-AAY, AAY-AAY-CAR-CAR-CAR-CAR, AAY-CAR-AAY-CAR-CAR-CAR, AAY-CAR-CAR-AAY-CAR-CAR, AAY-CAR-CAR-CAR-AAY-CAR, AAY-CAR-CAR-CAR-CAR-AAY, CAR-AAY-AAY-CAR-CAR-CAR, CAR-AAY-CAR-AAY-CAR-CAR, CAR-AAY-CAR-CAR-AAY-CAR, CAR-AAY-CAR-CAR-CAR-AAY, CAR-CAR-AAY-AAY-CAR-CAR, CAR-CAR-AAY-CAR-AAY-CAR, CAR-CAR-AAY-CAR-CAR-AAY, CAR-CAR-CAR-AAY-AAY-CAR, CAR-CAR-CAR-AAY-CAR-AAY, CAR-CAR-CAR-CAR-AAY-AAY-AAY, AAY-AAY-AAY-CAR-CAR-CAR-CAR, AAY-CAR-AAY-AAY-CAR-CAR-CAR, AAY-CAR-AAY-CAR-AAY-CAR-CAR, AAY-CAR-AAY-CAR-CAR-AAY-CAR, AAY-CAR-AAY-CAR-CAR-CAR-AAY, AAY-CAR-CAR-AAY-AAY-CAR-CAR, AAY-CAR-CAR-AAY-CAR-AAY-CAR, AAY-CAR-CAR-AAY-CAR-CAR-AAY, AAY-CAR-CAR-CAR-AAY-CAR-AAY, AAY-CAR-CAR-CAR-AAY-AAY-CAR, AAY-CAR-CAR-CAR-CAR-AAY-AAY, AAY-AAY-CAR-AAY-CAR-CAR-CAR, AAY-AAY-CAR-CAR-AAY-CAR-CAR, AAY-AAY-CAR-CAR-CAR-AAY-CAR, AAY-AAY-CAR-CAR-CAR-CAR-AAY, CAR-AAY-AAY-AAY-CAR-CAR-CAR, CAR-AAY-AAY-CAR-AAY-CAR-CAR, CAR-AAY-AAY-CAR-CAR-AAY-CAR, CAR-AAY-AAY-CAR-CAR-CAR-AAY, CAR-AAY-CAR-AAY-AAY-CAR-CAR, CAR-AAY-CAR-CAR-AAY-AAY-CAR, CAR-AAY-CAR-CAR-CAR-AAY-AAY, CAR-AAY-CAR-AAY-CAR-AAY-CAR, CAR-AAY-CAR-AAY-CAR-CAR-AAY, CAR-AAY-CAR-CAR-AAY-CAR-AAY, CAR-CAR-AAY-AAY-AAY-CAR-CAR, CAR-CAR-AAY-AAY-CAR-AAY-CAR, CAR-CAR-AAY-AAY-CAR-CAR-AAY, CAR-CAR-AAY-CAR-AAY-AAY-CAR, CAR-CAR-AAY-CAR-AAY-CAR-AAY, CAR-CAR-AAY-CAR-CAR-AAY-AAY, CAR-CAR-CAR-AAY-AAY-AAY-CAR, CAR-CAR-CAR-AAY-AAY-CAR-AAY, CAR-CAR-CAR-AAY-CAR-AAY-AAY, CAR-CAR-CAR-CAR-CAR-AAY-AAY, AAY-AAY-CAR-CAR-CAR-CAR-CAR, AAY-CAR-AAY-CAR-CAR-CAR-CAR, TABLE 7-continued (SEQ ID NOS: 2482-4747, respectively, in order of appearance)

AAY-CAR-CAR-AAY-CAR-CAR-CAR, AAY-CAR-CAR-CAR-AAY-CAR-CAR, AAY-CAR-CAR-CAR-CAR-AAY-CAR, AAY-CAR-CAR-CAR-CAR-CAR-AAY, CAR-AAY-AAY-CAR-CAR-CAR-CAR, CAR-AAY-CAR-AAY-CAR-CAR-CAR, CAR-AAY-CAR-CAR-AAY-CAR-CAR, CAR-AAY-CAR-CAR-CAR-AAY-CAR, CAR-AAY-CAR-CAR-CAR-CAR-AAY, CAR-CAR-AAY-AAY-CAR-CAR-CAR, CAR-CAR-AAY-CAR-AAY-CAR-CAR, CAR-CAR-AAY-CAR-CAR-AAY-CAR, CAR-CAR-AAY-CAR-CAR-CAR-AAY, CAR-CAR-CAR-AAY-AAY-CAR-CAR, CAR-CAR-CAR-AAY-CAR-AAY-CAR, CAR-CAR-CAR-AAY-CAR-CAR-AAY, CAR-CAR-CAR-CAR-AAY-AAY-CAR, CAR-CAR-CAR-CAR-AAY-CAR-AAY-CAR-CAR-CAR-CAR-CAR-CAR-AAY,

AAY-CAR-CAR-CAR-CAR-CAR-CAR, CAR-AAY-CAR-CAR-CAR-CAR-CAR, CAR-CAR-AAY-CAR-CAR-CAR-CAR, CAR-CAR-CAR-AAY-CAR-CAR-CAR, CAR-CAR-CAR-CAR-AAY-CAR-CAR, CAR-CAR-CAR-CAR-CAR-AAY-CAR

Oligonucleotides of peptide motifs containing 3-7 amino acide residues with Q(Glutamine) as the major constituent and D(Aspartic Acid) as the minor constituent CAR-CAR-GAY, GAY-CAR-CAR, CAR-GAY-CAR, CAR-CAR-CAR-GAY, GAY-CAR-CAR-CAR, CAR-GAY-CAR-CAR, CAR-CAR-GAY-CAR, CAR-CAR-CAR-CAR-GAY, GAY-CAR-CAR-CAR-CAR, CAR-GAY-CAR-CAR-CAR, CAR-CAR-GAY-CAR-CAR, CAR-CAR-CAR-GAY-CAR, CAR-CAR-CAR-GAY-GAY, GAY-GAY-CAR-CAR-CAR, GAY-CAR-GAY-CAR-CAR, GAY-CAR-CAR-GAY-CAR, GAY-CAR-CAR-CAR-GAY, CAR-GAY-GAY-CAR-CAR, CAR-GAY-CAR-GAY-CAR, CAR-GAY-CAR-CAR-GAY, CAR-CAR-GAY-GAY-CAR, CAR-CAR-GAY-CAR-GAY, CAR-CAR-CAR-CAR-CAR-GAY, GAY-CAR-CAR-CAR-CAR-CAR, CAR-GAY-CAR-CAR-CAR-CAR, CAR-CAR-GAY-CAR-CAR-CAR, CAR-CAR-CAR-GAY-CAR-CAR, CAR-CAR-CAR-CAR-GAY-CAR, CAR-CAR-CAR-CAR-GAY-GAY, GAY-GAY-CAR-CAR-CAR-CAR, GAY-CAR-GAY-CAR-CAR-CAR, GAY-CAR-CAR-GAY-CAR-CAR, GAY-CAR-CAR-CAR-GAY-CAR, GAY-CAR-CAR-CAR-CAR-GAY, CAR-GAY-GAY-CAR-CAR-CAR, CAR-GAY-CAR-GAY-CAR-CAR, CAR-GAY-CAR-CAR-GAY-CAR, CAR-GAY-CAR-CAR-CAR-GAY, CAR-CAR-GAY-GAY-CAR-CAR, CAR-CAR-GAY-CAR-GAY-CAR, CAR-CAR-GAY-CAR-CAR-GAY, CAR-CAR-CAR-GAY-GAY-CAR, CAR-CAR-CAR-GAY-CAR-GAY, CAR-CAR-CAR-CAR-GAY-GAY-GAY, GAY-GAY-GAY-CAR-CAR-CAR-CAR, TABLE 7-continued (SEQ ID NOS: 2482-4747, respectively, in order of appearance)

GAY-CAR-GAY-GAY-CAR-CAR-CAR, GAY-CAR-GAY-CAR-GAY-CAR-CAR, GAY-CAR-GAY-CAR-CAR-GAY-CAR, GAY-CAR-GAY-CAR-CAR-CAR-GAY, GAY-CAR-CAR-GAY-GAY-CAR-CAR, GAY-CAR-CAR-GAY-CAR-GAY-CAR, GAY-CAR-CAR-GAY-CAR-CAR-GAY, GAY-CAR-CAR-CAR-GAY-CAR-GAY, GAY-CAR-CAR-GAY-GAY-CAR, GAY-CAR-CAR-CAR-CAR-GAY-GAY, GAY-GAY-CAR-GAY-CAR-CAR-CAR, GAY-GAY-CAR-CAR-GAY-CAR-CAR, GAY-GAY-CAR-CAR-CAR-GAY-CAR, GAY-GAY-CAR-CAR-CAR-CAR-GAY, CAR-GAY-GAY-GAY-CAR-CAR-CAR, CAR-GAY-GAY-CAR-GAY-CAR-CAR, CAR-GAY-GAY-CAR-CAR-GAY-CAR, CAR-GAY-GAY-CAR-CAR-CAR-GAY, CAR-GAY-CAR-GAY-GAY-CAR-CAR, CAR-GAY-CAR-CAR-GAY-GAY-CAR, CAR-GAY-CAR-CAR-CAR-GAY-GAY, CAR-GAY-CAR-GAY-CAR-GAY-CAR, CAR-GAY-CAR-GAY-CAR-CAR-GAY, CAR-GAY-CAR-CAR-GAY-CAR-GAY, CAR-CAR-GAY-GAY-GAY-CAR-CAR, CAR-CAR-GAY-GAY-CAR-GAY-CAR, CAR-CAR-GAY-GAY-CAR-CAR-GAY, CAR-CAR-GAY-CAR-GAY-GAY-CAR, CAR-CAR-GAY-CAR-GAY-CAR-GAY, CAR-CAR-GAY-CAR-CAR-GAY-GAY, CAR-CAR-CAR-GAY-GAY-GAY-CAR, CAR-CAR-CAR-GAY-GAY-CAR-GAY, CAR-CAR-CAR-GAY-CAR-GAY-GAY, CAR-CAR-CAR-CAR-CAR-GAY-GAY, GAY-GAY-CAR-CAR-CAR-CAR-CAR, GAY-CAR-GAY-CAR-CAR-CAR-CAR, GAY-CAR-CAR-GAY-CAR-CAR-CAR, GAY-CAR-CAR-CAR-GAY-CAR-CAR, GAY-CAR-CAR-CAR-CAR-GAY-CAR, GAY-CAR-CAR-CAR-CAR-CAR-GAY, CAR-GAY-GAY-CAR-CAR-CAR-CAR, CAR-GAY-CAR-GAY-CAR-CAR-CAR, CAR-GAY-CAR-CAR-GAY-CAR-CAR, CAR-GAY-CAR-CAR-CAR-GAY-CAR, CAR-GAY-CAR-CAR-CAR-CAR-GAY, CAR-CAR-GAY-GAY-CAR-CAR-CAR, CAR-CAR-GAY-CAR-GAY-CAR-CAR, CAR-CAR-GAY-CAR-CAR-GAY-CAR, CAR-CAR-GAY-CAR-CAR-CAR-GAY, CAR-CAR-CAR-GAY-GAY-CAR-CAR, CAR-CAR-CAR-GAY-CAR-GAY-CAR, CAR-CAR-CAR-GAY-CAR-CAR-GAY, CAR-CAR-CAR-CAR-GAY-GAY-CAR, CAR-CAR-CAR-GAY-CAR-GAY-CAR-CAR-CAR-CAR-CAR-CAR-GAY,

GAY-CAR-CAR-CAR-CAR-CAR-CAR, CAR-GAY-CAR-CAR-CAR-CAR-CAR, CAR-CAR-GAY-CAR-CAR-CAR-CAR, CAR-CAR-CAR-GAY-CAR-CAR-CAR, CAR-CAR-CAR-CAR-GAY-CAR-CAR, CAR-CAR-CAR-CAR-CAR-GAY-CAR

TABLE 8

| Symbol | | Origin of designation |
|---|---|---|
| a | a | adenine |
| g | g | guanine |
| c | c | cytosine |
| t | t | thymine |
| u | u | uracil |
| r | g or a | purine |
| y | t/u or c | pyrimidine |
| m | a or c | amino |
| k | g or t/u | keto |
| s | g or c | strong interactions 3H-bonds |
| w | a or t/u | weak interactions 2H-bonds |
| b | g or c or t/u | not a |
| d | a or g or t/u | not c |
| h | a or c or t/u | not g |
| v | a or g or c | not t, not u |
| n | a or g or c or t/u, unknown, or other | any |

TABLE 9

(NNT155 disclosed as SEQ ID NO: 2)

| Code Construct | Admin Dose° µg/kg | $AUC_\infty$ ng*h/mL | T last h | AUC/D h*kg*ng/mL/µg | $t_{1/2}$ h | Cl mL/h/kg | $V_{ss}$ mL/kg | $MRT_\infty$ h | Dose normalized $AUC_\infty^{\S}$ ng*h/mL |
|---|---|---|---|---|---|---|---|---|---|
| NNT155 | 2.6 | 274.5 | 24 | 105.6 | 6.2 | 9.5 | 78.2 | 8.2 | 316.7 |
| C-GSF Control (A) | 3.2 | 20.91 | 8 | 6.53 | 1.53 | 153.0 | 160.1 | 1.0 | 19.60 |
| NEUPOGEN ®[30] | 3.0 | 47.01 | 8 | 15.7 | 1.13 | 63.8 | 77.0 | 1.2 | 47.01 |
| NEULASTA | 6.0 | 116.4 | 24 | 19.4 | 3.04 | 51.5 | 266.1 | 5.2 | 58.20 |

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08748577B2). An electronic copy of the "Sequence Listing" will also be available from the USPTO upon request and payment of the fee set forth in 37 CFR 1.19(b)(3).

The invention claimed is:

1. A biologically active protein conjugate comprising a biologically active polypeptide coupled via a peptide bond to an amino acid extension comprising from 2 to 75 repeating units of a peptide motif, wherein said peptide motif consists of two residues Asn (N) and one residue of an amino acid selected from the group consisting of Ser (S) and Thr (T), wherein the biologically active polypeptide is human growth hormone SEQ ID NO:2472, granulocyte macrophage colony stimulating factor (GM-CSF; SEQ ID NO:2462), granulocyte colony stimulating factor (G-CSF), macrophage colony stimulating factor (M-CSF; SEQ ID NOs:2454, 2456, 2458, or 2460), colony stimulating factor (CSF), platelet derived growth factor (PDGF), tumor necrosis factor (TNF), epidermal growth factor (EGF), vascular endothelial growth factor (VEGF), fibroblast growth factor, (FGF), nerve growth factor (NGF), erythropoietin (EPO; SEQ ID NOs:2452, 2480, or 2481), interferon, interferon gamma inducing factor I (IGIF), transforming growth factor beta (TGF-β), RANTES (regulated upon activation, normal T-cell expressed and presumably secreted), macrophage inflammatory protein-1-alpha (MIP-1-α), macrophage inflammatory protein-1-β (MIP-1-β), Leishmania elongation initiating factor (LEIF), brain derived neurotrophic factor (BDNF), neurotrophin-2 (NT-2), neurotrophin-3 (NT-3), neurotrophin-4 (NT-4), neurotrophin-5 (NT-5), glial cell line-derived neurotrophic factor (GDNF), ciliary neurotrophic factor (CNTF), a soluble tumor necrosis factor (TNF) type II receptor, a soluble tumor necrosis factor (TNF) type I receptor, a soluble IL-1 receptor type II, a soluble IL-4 receptor, a soluble gp120 glycoprotein, a soluble gp160 glycoprotein, an IL-1 receptor antagonist, a coagulation factor, insulin, activated protein C, Factor VII, collagenase, agalsidase-beta, dornase-alpha, alteplase, pegylated-asparaginase, asparaginase, or imiglucerase, and wherein said biologically active protein conjugate has an increased plasma half-life compared to the plasma half-life of the unmodified biologically active polypeptide.

2. The biologically active protein conjugate of claim 1, wherein said peptide motif has an amino acid sequence selected from the group consisting of SNN, NSN, NNS, TNN, NTN, and NNT.

3. The biologically active protein conjugate of claim 1, wherein said amino acid extension is situated at the N-terminus with respect to said biologically active polypeptide, is situated at the C-terminus with respect to said biologically active polypeptide, or is situated at both the N- and C-termini with respect to said biologically active polypeptide.

4. The biologically active protein conjugate of claim 1, wherein said interferon is selected from the group consisting of a beta-interferon (SEQ ID NO:2468) and a gamma-interferon (SEQ ID NO:2470).

5. The biologically active protein conjugate of claim 1, wherein said biologically protein conjugate further comprises a leader sequence.

6. The biologically active protein conjugate of claim 5, wherein the leader sequence is the *Schizosaccharomyces pome* acid phosphatase (PHO) leader sequence (amino acid residues 1 to 18 of SEQ ID NO:2450).

7. The biologically active protein conjugate of claim 1, wherein said biologically active protein conjugate further comprises a linker.

8. A composition comprising the biologically active protein conjugate of claim 1 and a pharmaceutically effective carrier.

* * * * *

UNITED STATES PATENT AND TRADEMARK OFFICE

CERTIFICATE OF CORRECTION

PATENT NO. : 8,748,577 B2
APPLICATION NO. : 13/363278
DATED : June 10, 2014
INVENTOR(S) : Besman et al.

It is certified that error appears in the above-identified patent and that said Letters Patent is hereby corrected as shown below:

In the Claims

| COLUMN | LINE | |
|---|---|---|
| 115<br>Claim 1 | 58 | after "fibroblast growth factor" delete "," |
| 117<br>Claim 5 | 2 | delete "biologically protein conjugate" and insert<br>--biologically active protein conjugate-- |

Signed and Sealed this
Fourth Day of November, 2014

Michelle K. Lee

Michelle K. Lee
*Deputy Director of the United States Patent and Trademark Office*